US010774149B2

(12) United States Patent
Stone et al.

(10) Patent No.: US 10,774,149 B2
(45) Date of Patent: *Sep. 15, 2020

(54) COMPOSITION COMPRISED OF ANTIGEN LINKED TO A TNF SUPERFAMILY LIGAND

(71) Applicants: Geoffrey W. Stone, San Francisco, CA (US); Richard S. Kornbluth, La Jolla, CA (US)

(72) Inventors: Geoffrey W. Stone, San Francisco, CA (US); Richard S. Kornbluth, La Jolla, CA (US)

(73) Assignee: UNIVERSITY OF MIAMI, Miami, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/053,767

(22) Filed: Aug. 2, 2018

(65) Prior Publication Data

US 2019/0010240 A1 Jan. 10, 2019

Related U.S. Application Data

(62) Division of application No. 14/776,609, filed as application No. PCT/US2014/030099 on Mar. 16, 2014, now Pat. No. 10,072,064.

(60) Provisional application No. 61/903,378, filed on Nov. 12, 2013, provisional application No. 61/794,520, filed on Mar. 15, 2013.

(51) Int. Cl.
| *A61K 39/00* | (2006.01) |
| *A61K 39/21* | (2006.01) |
| *C07K 14/005* | (2006.01) |
| *C07K 16/28* | (2006.01) |
| *C07K 14/705* | (2006.01) |
| *C07K 14/785* | (2006.01) |
| *C12N 7/00* | (2006.01) |
| *A61P 31/18* | (2006.01) |
| *A61P 35/00* | (2006.01) |
| *A61K 38/00* | (2006.01) |

(52) U.S. Cl.
CPC .......... *C07K 16/2878* (2013.01); *A61K 39/00* (2013.01); *A61K 39/0011* (2013.01); *A61K 39/21* (2013.01); *A61P 31/18* (2018.01); *A61P 35/00* (2018.01); *C07K 14/005* (2013.01); *C07K 14/705* (2013.01); *C07K 14/70575* (2013.01); *C07K 14/785* (2013.01); *C12N 7/00* (2013.01); *A61K 38/00* (2013.01); *A61K 2039/5154* (2013.01); *A61K 2039/53* (2013.01); *A61K 2039/55516* (2013.01); *A61K 2039/572* (2013.01); *A61K 2039/645* (2013.01); *C07K 2317/622* (2013.01); *C07K 2319/30* (2013.01); *C07K 2319/33* (2013.01); *C07K 2319/40* (2013.01); *C12N 2740/16034* (2013.01); *C12N 2740/16234* (2013.01)

(58) Field of Classification Search
None
See application file for complete search history.

(56) References Cited

U.S. PATENT DOCUMENTS

| 6,190,886 B1 | 2/2001 | Hoppe et al. |
| 6,482,411 B1 | 11/2002 | Ahuja et al. |
| 6,923,958 B2 | 8/2005 | Xiang et al. |
| 7,279,464 B2 | 10/2007 | Xiang et al. |
| 7,300,774 B1 | 11/2007 | Kornbluth |
| 7,332,298 B2 | 11/2008 | Kornbluth |
| 7,959,925 B2 | 6/2011 | Weinberg et al. |
| 2009/0081157 A1* | 3/2009 | Kornbluth .............. A61K 39/21 424/85.2 |

FOREIGN PATENT DOCUMENTS

| EP | 1 246 925 B1 | 5/2008 |
| WO | WO 0142298 | 6/2001 |
| WO | WO 2007067681 | 6/2007 |
| WO | WO 2011108937 | 9/2011 |

OTHER PUBLICATIONS

Melchers et al. A stabilized HIV-1 envelope glycoprotein trimer fused to CD40 ligand targets and activates dendritic cells. Retrovirology 2011, 8:48.*
Ahmad et al., "scFv Antibody: Principles and Clinical Application" Clin. Dev. Immunol. 2012; 2012:980250. PMCID: 3312285.
Ahmadi et al., "CD40 Ligand-activated, antigen-specific B cells . . . " Immunology, 2008;124(1):129-40.
Bajorath et al., "Analysis of gp39/CD40 interactions using molecular models and site-directed mutagenesis" Biochemistry, 1995;34(31):9884-92.
Barr et al., "A potent adjuvant effect of CD40 antibody attached to antigen" Immunology, 2003;109(1):87-92.
Barth et al., "A Randomized Trial of Ex vivo CD4OL Activation of a Dendritic Cell Vaccine . . . " Clinical Cancer Research, 2010;16(22):5548-56.

(Continued)

*Primary Examiner* — Nianxiang Zou
(74) *Attorney, Agent, or Firm* — Stacey J. Farmer, Esq.; Alan Heimlich, Esq.

(57) ABSTRACT

The invention provides fusion proteins comprising antigens of infectious disease agents and cancer cells linked to multiple-trimer forms of TNF SuperFamily (TNFSF) ligands. The TNFSFs serve as vaccine adjuvants for increasing the immune response to the antigens. In particular, a fusion polypeptide strand that self-assembles inside cells into a multiple-trimer form of CD40 ligand (CD40L, TNFSF5) is provided. Other similar fusion proteins are also disclosed. The fusion proteins can be delivered to a host as isolated proteins, as nucleic acids used directly in DNA vaccination or carried and expressed by a viral vector such as adenovirus. In addition to use as a vaccine to prevent or ameliorate disease caused by an infectious agent, compositions of the invention may be used for the treatment of ongoing infection or for cancer immunotherapy.

19 Claims, 17 Drawing Sheets

Specification includes a Sequence Listing.

(56) References Cited

OTHER PUBLICATIONS

Bonifaz et al., "In vivo targeting of antigens to maturing dendritic cells via the DEC-205 receptor improves T cell vaccination" J Exp Med. 2004;199(6):815-24.
Bonifaz et al.,"Efficient targeting of protein antigen to the dendritic cell receptor DEC-205 . . . " J. Exp. Med. 2002;196(12)1627-38. PMCID: 2196060.
Brossart et al. "Induction of cytotoxic T-lymphocyte responses in vivo after vaccinations with peptide-pulsed dendritic cells", Blood, 96:9, pp. 3102-3108 (Nov. 1, 2000).
Bulliard et al. "Activating Fc γ receptors contribute to the antitumor activities of immunoregulatory receptor-targeting antibodies" J Exp Med. 2013;210(9):1685-93.
Castle et al., "Exploiting the mutanome for tumor vaccination" Cancer Res. 2012;72(5)1081-91.
Chaise et al., "DNA vaccination induces WT1-specific T-cell responses with potential clinical relevance" Blood, 2008;112(7):2956-64.
Chatterjee et al., "Internalization and endosomal degradation of receptor-bound antigens . . . " Blood, 2012;120(10):2011-20.
Cheever et al. "The Prioritization of Cancer Antigens: A National Cancer Institute Pilot Project . . . " Clin Cancer Res 15, 5323-5337, 2009.
Cohn et al., "Antigen delivery to early endosomes eliminates the superiority of human blood BDCA3+ dendritic cells . . . " J Exp Med. 2013;210(5):1049-63. PMCID: 3646496.
Crouch et al., "Molecular structure of pulmonary surfactant protein D (SP-D)" J Biol Chem. 1994;269(25):17311-9.
Delamarre et al., "Presentation of Exogenous Antigens on Major Histocompatibility Complex (MHC) Class I and MHC Class II . . . " J Exp Med. 2003;198(1):111-122.
Dunn et al., "Cancer immunoediting: from immunosurveillance to tumor escape" 2002;3(11):991-8.
Epstein et al., "Live Attenuated Malaria Vaccine Designed to Protect Through Hepatic CD8+T Cell Immunity" Science, 2011;334(6055):475-80.
Gervais et al. "Ex vivo expansion of antitumor cytotoxic lymphocytes . . . ", Cancer Res. & Treatment, vol. 25, No. 3B, pp. 2177-2185.
Gold et al., "A Single Heteroclitic Epitope Determines Cancer Immunity After Xenogeneic DNA Immunization . . . " J Immunol. 2003;170(10):5188-94.
Groeper et al., "Cancer/testis antigen expression and specific cytotoxic T lymphocyte responses in non small cell lung cancer" Int J Cancer. 2007; 120(2):337-43.
Gupta et al. "Vaccination with a fusion protein that introduces HIV-1 gag antigen into a multitrimer CD4OL construct . . . " J. of Virology, 88:3, pp. 1492-1501.
Hailemichael et al., "Persistent antigen at vaccination sites induces tumor-specific CD8• T cell sequestration . . . " Nat. Med. 2013;19(4):465-72. PMCID: 3618499.
Hansen et al., "Profound early control of highly pathogenic SIV by an effector memory T-cell vaccine" Nature. 2011;473(7348):523-7. PMCID: 3102768.
Haswell et al., "Analysis of the oligomeric requirement for signaling by CD40 using soluble multimeric forms of its ligand, CD154" Eur J Immunol. 2001;31(10):3094-3100.
Holler et al. "Two adjacent trimeric Fas ligands are required for Fas signaling and formation of a death-inducing signaling complex" Mol Cell Biol. 2003;23(4)1 428-40.
Inaba et al., "Tissue distribution of the DEC-205 protein that is detected by the monoclonal antibody NLDC-145 . . . " Cellular immunology. 1995;163(1):148-56.
Kamath et al. "Synchronization of dendritic cell activation and antigen exposure is required for the induction of Th1/Th17 responses" J Immunol. 2012;188(10):4828-37.
Kanagavelu et al., "Soluble multi-trimeric TNF superfamily ligand adjuvants enhance immune responses . . . " Vaccine. 2012;30(4)691-702. PMCID: 3253891.
Kornbluth et al., "Design of CD40 agonists and their use in growing B cells for cancer immunotherapy" International Reviews of Immunology. 2012;31(4):279-88.
Kurokawa T. et al. "Induction and clonal expansion of tumor-specific cytotoxic T lymphocytes from renal cell carcinoma patients . . . " IJC, vol. 91, No. 6, pp. 749-756 (2001).
Kvistborg et al. "Human cancer regression antigens" Curr. Opinion Immunol. 25:284-290, 2013.
Li et al., "Inhibitory Fcγ receptor engagement drives adjuvant and anti-tumor activities of agonistic CD40 antibodies" Science. 2011;333(6045)1030-4. PMCID: 3164589.
Maurais et al., "Human immunodeficiency virus type 1-anchored CD40 ligand induces secretion of the chemokine interleukin-8 . . . " Virology, 2009;385(1):227-32.
Meyer et al. "Reduced antibody response to streptavidin through site-directed mutagenesis" Protein Science 2001;10(3):491-503.
Miconnet et al., "A soluble hexameric form of CD40 ligand activates human dendritic cells and augments memory T cell response" Vaccine. 2008;26(32):4006-14.
Oelke M. et al., "Generation and purification of CD8+ melan-A-specific cytotoxic T lymphocytes for adoptive transfer . . . ", Clin. Can. Res, AACR, vol. 6, No. 5, pp. 1997-2005.
Qiu et al. "Evaluation of novel human immunodeficiency virus type 1 Gag DNA vaccines for protein expression . . . " J Virol. 1999;73(11):9145-52.
Restifo et al., "Adoptive immunotherapy for cancer: harnessing the T cell response" Nature Reviews Immunology. 2012;12(4):269-81.
Sanchez et al., "An alternative signal 3: CD8• T cell memory independent of IL-12 and type I IFN is dependent on CD27/OX40 signaling" Vaccine. 2012;30(6):1154-61.
Schabosky et al., "ProtEx technology for the generation of novel therapeutic cancer vaccines" Exp Mol Pathol. 86:198-207 (2009).
Sedegah et al., "Boosting with recombinant vaccinia increases immunogenicity and protective efficacy of malaria DNA vaccine" Proc Natl Acad Sci USA 1998;95(13):7648-53.
Segal et al., "Epitope landscape in breast and colorectal cancer" Cancer Res. 2008;68(3):889-92.
Siegel et al., "A domain in TNF receptors that mediates ligand-independent receptor assembly and signaling" Science. 2000;288(5475):2351-4.
Slutter et al., "Cutting edge: rapid boosting of cross-reactive memory CD8 T cells broadens the protective capacity of the Flumist vaccine" J Immunol. 2013;190(8):3854-8.
Smulski et al., "Cysteine-rich domain 1 of CD40 mediates receptor self-assembly" J Biol Chem. 2013.
Stone et al., "Macaque Multimeric Soluble CD40 Ligand and GITR Ligand Constructs Are Immunostimulatory Molecules in Vitro" Clin Vaccine Immunol. 2006;13(11):1223-30.
Stone et al., "Multimeric soluble CD40 ligand and GITR ligand as adjuvants for human immunodeficiency virus DNA vaccines" J Virol. 2006;80(4):1762-72.
Vonderheide et al., "Clinical activity and immune modulation in cancer patients treated with CP-870,893 . . . " J. Clin. Oncol. 2007;25(7):876-83.
White et al., "Interaction with FcγRIIB is critical for the agonistic activity of anti-CD40 monoclonal antibody" J Immunol. 2011;187(4):1754-63.
Wilson et al., "An Fcγ Receptor-Dependent Mechanism Drives Antibody-Mediated Target-Receptor Signaling in Cancer Cells" Cancer Cell. 2011;19(1):101-13.
Xiang et al. "A dual-function DNA vaccine encoding carcinoembryonic antigen and CD40 ligand trimer . . . " J. Immunol. 2001;167(8):4560-5.
Yee Cassian et al., "Adoptive therapy using antigen-specific T-cell clones", Cancer Journal, vol. 16, No. 4, pp. 367-373 (2010).
Yumura et al., "Mutations for decreasing the immunogenicity and maintaining the function of core streptavidin" Protein Science 2013;22(2):213-21.
Zhou et al., "Human glucocorticoid-induced TNF receptor ligand regulates its signaling activity through multiple oligomerization states" PNAS USA, 2008;105(14):5465-70.

(56) References Cited

OTHER PUBLICATIONS

Kanagavelu et al: "Soluble multi-trimeric TNF superfamily ligand adjuvants enhance immune responses to a HIV-1 Gag DNA vaccine". Vaccine. Elsevier Ltd. GB. vol. 30. No. 4. Nov. 22, 2011 (Nov. 22, 2011). pp. 691-702.

Mosby's Medical Dictionary, 9th: edition. (c) 2009, Elsevier., http://medical-dictionary.thefreedictionary.com/xenogeneic.

\* cited by examiner

COMPOSITION COMPRISED OF ANTIGEN LINKED TO A TNF SUPERFAMILY LIGAND

RELATED APPLICATION

The present application for patent claims priority to U.S. patent application Ser. No. 14/776,609 titled "COMPOSITION COMPRISED OF ANTIGEN LINKED TO A TNF SUPERFAMILY LIGAND" filed 2015 Sep. 14, pending, and which is hereby incorporated herein by reference. The present application for patent claims priority to PCT/US2014/030099 titled "COMPOSITION COMPRISED OF ANTIGEN LINKED TO A TNF SUPERFAMILY LIGAND" filed 2014 Mar. 16, pending, which was published in English under PCT Article 21(2) and which is hereby incorporated herein by reference. The present application for patent claims priority to U.S. Patent Application No. 61/794,520 titled "METHOD TO LINK AN ANTIGEN TO A TNF SUPERFAMILY LIGAND" filed 2013 Mar. 15, and which is hereby incorporated herein by reference. The present application for patent claims priority to U.S. Patent Application No. 61/903,378 titled "COMPOSITION COMPRISED OF ANTIGEN LINKED TO A TNF SUPERFAMILY LIGAND" filed 2013 Nov. 12, and which is hereby incorporated herein by reference. PCT/US2014/030099 titled "COMPOSITION COMPRISED OF ANTIGEN LINKED TO A TNF SUPERFAMILY LIGAND" filed 2014 Mar. 16, pending claims priority to U.S. Patent Application No. 61/794,520 titled "METHOD TO LINK AN ANTIGEN TO A TNF SUPERFAMILY LIGAND" filed 2013 Mar. 15, and to U.S. Patent Application No. 61/903,378 titled "COMPOSITION COMPRISED OF ANTIGEN LINKED TO A TNF SUPERFAMILY LIGAND" filed 2013 Nov. 12.

STATEMENT REGARDING FEDERALLY SPONSORED RESEARCH OR DEVELOPMENT

This invention was made with government support under Grant No. AI068489 awarded by the National Institutes of Health (NIH) of the United States of America. The government has certain rights in this invention.

FIELD OF THE INVENTION

The present invention generally relates to compositions useful for generating or enhancing an immune response against an antigen, to methods for using the compositions, and to modified immune cells useful in such methods.

BACKGROUND OF THE INVENTION

Industrial applications of vaccines: Vaccines are considered to be among the most cost-effective and health-preserving medical inventions ever developed. The rationale for vaccination is that pre-exposure of the host to a vaccine against a given infectious agent can ameliorate or prevent disease should the vaccinated individual become exposed to that agent at a later time. The gap in time between vaccination and possible exposure requires "memory" on the part of the immune system. This memory is embodied in the persistence of immune cells for years or even decades after vaccination. Creating vaccines that induce strong and lasting protection is a difficult task, given our incomplete knowledge of the immune system. Nevertheless, continuing advances in our understanding make possible new approaches to vaccine design.

Vaccines against infectious agents: For microbial agents, many vaccines in use are comprised of live attenuated or non-virulent strains of the disease-causing microorganisms. Other vaccines are comprised of killed or otherwise inactivated microorganisms. Yet other vaccines utilize purified components of pathogen lysates, such as surface carbohydrates or recombinant pathogen-derived proteins. Vaccines that utilize live attenuated or inactivated pathogens typically yield a vigorous immune response, but their use has limitations. For example, live vaccine strains can sometimes mutate back into disease-causing variants, especially when administered to immunocompromised recipients. Moreover, many pathogens, particularly viruses, undergo continuous rapid mutations in their genome, which allow them to escape immune responses to antigenically distinct vaccine strains.

Vaccines for the prevention or treatment of cancer: As the understanding of immunity has developed, it became clear that the immune system also controls or attempts to control the development of malignancies (Dunn et al., 2002; 3(11):991-8). As a result, immunotherapy is now being used to eradicate or control certain human cancers. Some of the technology and concepts of vaccines against infectious agents also apply to using the immune system to fight cancers, both solid tumors and blood cancers such as leukemia. Patients at risk for cancer, such as those infected by cancer-associated viruses like human papilloma virus (HPV), can be protected from developing the particular cancer in question as exemplified by Gardasil® vaccination against human papilloma virus (HPV), which causes cervical cancer. Patients who already have cancer, such as prostate cancer, can also be helped by vaccination, as exemplified by the Provenge® vaccine which is an immunotherapy for prostate cancer.

CD8+ T cells can recognize conserved antigens in many infectious agents and prevent disease: While these have been successful vaccines, there have been major problems constructing vaccines against antigens from rapidly mutating infectious agents such as influenza, HIV, and *Plasmodium falciparum* (a cause of malaria). In these cases and others, the infectious agent has surface protein(s) that can rapidly mutate to evade otherwise protective antibodies. Nevertheless, these agents also have relatively conserved and unchanging internal components as exemplified by nucleoprotein (NP) of influenza, Gag and Pol for HIV, and circumsporozoite surface protein (CSP) for *Plasmodium falciparum*. In these cases, antibodies (which can only bind to the surface of pathogens) are unable to bind to these more conserved and internal antigens. Instead, there is a well-established role for CD8+ T cells in controlling or clearing such infectious agents—provided that a strong enough CD8+ T cell response can be generated. To cite just three examples: (1) Protection from disease caused by influenza can be achieved by high levels of CD8+ T cells against the conserved nucleoprotein (NP) viral protein (Webster et al., Eur J Immunol. 1980; 10(5):396-401; Slutter et al., J Immunol. 2013; 190(8):3854-8. PMCID: 3622175.). (2) Strong CD8+ T cell responses against the Gag and Pol proteins of simian immunodeficiency virus (SIV, a non-human primate model for HIV infection) can protect macaques from developing AIDS after challenge with SIV (Hansen et al., Nature. 2011; 473(7348):523-7. PMCID: 3102768). (3) CD8+ T cells against *Plasmodium falciparum* antigens can protect humans from malaria (Epstein et al., Science. 2011; 334 (6055):475-80). Thus, there is an urgent and largely unmet need to develop better ways of eliciting strong CD8+ T cells to protect against infection.

CD8+ T cells can recognize cancer antigens and cure malignancy: Similar to the situation with infectious agents, CD8+ T cells can also be generated against tumor cell antigens. As exemplified by Tumor-Infiltrating Lymphocytes (TILs), the passive administration of anti-tumor CD8+ T cells can be sufficient to cure patients of advanced cancers in a small percentage of cases (Restifo et al., Nature Reviews Immunology. 2012; 12(4):269-81). These CD8+ T cells recognize peptides termed "tumor antigens" where the tumor contains antigens either not found in normal tissue or present at much lower levels. As noted above, some tumor antigens are derived from tumorigenic viruses such as the E6 and E7 antigens in HPV-related cervical cancer. Other tumor antigens are derived from mutations in germline proteins such as the V600E mutation in the BRAF protein. Yet other tumor antigens are normal proteins such as HER-2/neu which is overexpressed in breast cancer, where the breast is a non-essential "disposable" tissue that can be sacrificed by an immune attack on breast-derived tissues. Here again, there is an urgent and largely unmet need to develop better ways of eliciting strong CD8+ T cell responses to protect against cancer or treat patients with already established malignant disease.

Numerous licensed vaccines are live, attenuated viruses (LAV): As noted above, there is a major problem in the art which is that it has been difficult to develop industrial applicable vaccines that are able to generate antigen-specific CD8+ T cells. For viral infections, one of the best ways is to generate anti-viral CD8+ T cells is to vaccinate with a live, attenuated virus (LAV) vaccine. Familiar examples of LAV vaccines are the Measles/Mumps/Rubella (MMR) vaccine, Sabin poliovirus vaccine, FluMist® influenza vaccine, Yellow Fever Virus 17D vaccine, and Vaccinia smallpox vaccine. But it has been difficult to produce LAV vaccines against viral infections for a variety of reasons that include inefficient manufacturing process, a need for repeated vaccination with follow-up "booster" vaccination many years later, and the generally poor quality and low level of the CD8+ T cell response to many vaccine candidates.

CD8+ T cells can cure cancer in humans but are difficult to generate: For cancers not associated with viruses, there is no possibility of developing an LAV type vaccine. Instead, tumor antigens must be identified or otherwise isolated or predicted and used for vaccination. To be curative for cancer, a substantial CD8+ T cell response is needed. This has been shown for regimens that isolate and expand tumor-infiltrating lymphocytes (TIL) which are CD8+ T cells grown ex vivo and then administered back to the patients. In these studies, a relatively high number of TIL CD8+ T cells is required to successfully eradicate and cure metastatic melanoma (Restifo et al., Nature Reviews Immunology. 2012; 12(4):269-81). Many seemingly auspicious cancer vaccines and immunotherapies turn out to be too weak to cure cancer when tested in vivo. For example, simply vaccinating with a tumor antigen peptide emulsified in Montanide lipid as an immunostimulant fails to cure cancer because the resulting CD8+ T cells do not enter the circulation and go to the tumors (Hailemichael et al., Nat Med. 2013; 19(4):465-72. PMCID: 3618499).

CD8+ T cells are stimulated by antigen peptides presented on MHC Class I (MHC-I): In order to understand the process for generating CD8+ T cells, it is helpful to review how they arise during a normal immune response. CD8+ T cells are named because they have the CD8 protein on their surface. CD8 works as a "co-receptor" along with the T cell receptor (TCR) to recognize peptide antigens (typically 7-11 amino acids in length) that are processed inside of cells by the cleavage of the intact proteins and then displayed on the surface of infected cells by major histocompatibility complex (MHC) Class I (MHC-I) molecules. These MHC-I molecules hold the peptide antigen in a "groove" and the CD8+ T cell then recognizes the peptide-MHC-I (pMHC-I) complex and becomes activated. CD8+ T cells that kill the infected cell are termed "cytotoxic" but they can also interfere with infectious agents by producing cytokines such as interferon-gamma (IFN-g).

Considering the foregoing, it is highly desirable to find an industrially applicable means for producing vaccines that are highly effective for eliciting strong CD8+ T cells, CD4+ T cells, and antibody responses against infectious agents and tumor antigens.

Need for antigen-presenting cells (APC) to generate antigen-specific CD8+ T cells: With this as an introduction, it can be appreciated that a key event in the generation of CD8+ T cells is to develop a cell type called an "antigen-presenting cell" (APC) that can present pMHC-I to uneducated or naïve CD8+ T cell precursors to induce them to divide, expand in numbers, and persist for prolonged periods as highly active "memory" CD8+ T cells. To be effective at generating CD8+ T cells, an APC must both express peptide antigen on MHC-I (pMHC-I) that is recognized by the TCR (called "Signal 1") and also co-stimulate the responding cells through additional receptor (called "Signal 2") and even other receptors (called "Signal 3"). TCR stimulation by pMHC-I provides Signal 1 and generally stimulation of the CD28 receptor on CD8+ T cells provides Signal 2. Signal 3 can be provided in a non-redundant fashion either by soluble proteins such as interferon-alpha (Type I interferon) and/or interleukin-12 (IL-12) and/or cell surface molecules such as CD27 ligand (CD27L, also called CD70 or TNFSF7), 4-1BBL (also called CD137L or TNFSF9), and/or OX40L (also called CD134L or TNFSF4) (Sanchez and Kedl, Vaccine. 2012; 30(6):1154-61. PMCID: 3269501). What is needed is a vaccine approach that can activate an APC to provide all of these signals. This requires a good dendritic cell stimulus, also called an "immune adjuvant" or "adjuvant."

APC cross-presentation of extracellular antigens: The first requirement for an APC is to express peptide antigen on MHC-I (pMHC-I). The prototypic APC is the dendritic cell which takes up protein antigens from its environment, degrades these proteins into peptides, loads the resulting peptides onto MHC-I, and then presents the pMHC-I on their surface to provide the TCR stimulus that is Signal 1. This process is very different from cells infected by a microbial pathogen or tumor cells. In those cases, the protein antigen is produced within the cell itself—not taken up from the extracellular space—and then protein degradation products (which are peptides) are loaded onto MHC-I and exported to the cell surface as pMHC-I to provide Signal 1. What makes dendritic cells and other APCs special is that they can form pMHC-I from proteins in their environment, a phenomenon termed "cross-presentation." For dendritic cells to do this, they must take up the protein antigen from their environment using one of a few very specialized receptors, including DEC205, CD11c, BDCA1, BDCA3, and/or CD40. After taking up protein antigen from the extracellular space, these receptors direct the delivery of the protein antigen into membrane-limited intracellular compartments ("endosomes") where the protein can be digested into peptides and then transferred into compartments where MHC-I is being assembled. Of special important to the instant invention is that the best receptor on dendritic cells for processing protein antigen into pMHC-I (i.e., crosspresentation) is the CD40 receptor (Chatterjee et al., Blood. 2012; 120(10):2011-20; Cohn et al., J Exp Med. 2013; 210(5):1049-63. PMCID: 3646496). Therefore, it is highly desirable for a vaccine to include a protein antigen that is targeted toward the CD40 receptor on dendritic cells.

Activation of the APC stimulates crosspresentation: A second requirement for an APC to crosspresent an exogenous protein antigen is for the APC to be "activated." For dendritic cells, such activation is ideally provided by an effective stimulus through the CD40 receptor, which promotes crosspresentation and the formation of the pMHC-I Signal 1 (Delamarre et al., J Exp Med. 2003; 198(1):111-22) Similarly, B cells, which are another type of APC, can be activated by a CD40 receptor stimulus to crosspresent soluble protein antigens (Ahmadi et al., Immunology. 2008; 124(1):129-40).

Crosspresentation of antigen by dendritic cells in the absence of CD40 stimulation leads to CD8+ T cell tolerance: DEC-205 is a receptor on dendritic cells and B cells recognized on mouse cells by the NLDC-145 monoclonal antibody (Inaba et al., Cellular immunology. 1995; 163(1):148-56). Bonifaz et al. showed that the binding portion of an anti-DEC205 antibody can be genetically fused to a model antigen, chicken ovalbumin (OVA). The injection of anti-DEC205/OVA fusion protein directs the OVA antigen to dendritic cells and leads to crosspresentation of OVA peptide antigen on MHC-I. However, while this treatment induces anti-OVA CD8+ T cells to divide and proliferate, these cells soon die off and are deleted. This results in specific tolerance for OVA that cannot be overcome by subsequent vaccination with OVA plus Complete Freund's Adjuvant (CFA), which is usually considered to be a gold standard for vaccination (although CFA is far too inflammatory to be used in humans). However, if anti-DEC205/OVA fusion protein is combined with a stimulus for the CD40 receptor, then very strong anti-OVA CD8+ T cell responses result (Bonifaz et al., J Exp Med. 2002; 196(12):1627-38. PMCID: 2196060). This indicates that simply targeting antigens to dendritic cells alone (e.g., using a fusion protein of anti-DEC205 and antigen) does not succeed in eliciting high levels of efficacious and persisting antigen-specific CD8+ T cells. In fact, it shows that allowing antigen to be taken up by unactivated dendritic cells should be avoided because it will work against the goal of creating strong antigen-specific CD8+ T cell responses.

Generating CD8+ T cell responses is best when antigen is delivered to dendritic cells in conjunction with an adjuvant: Although they did not use a CD40 stimulus, Kamath et al. 0 Immunol. 2012; 188(10):4828-37) developed a vaccine system for delivering an antigen either directly attached to an antigen or co-delivered with a separate, unattached antigen. When antigen was delivered to DCs in the absence of adjuvant, antigen-specific T cells were induced to proliferate but did not subsequently differentiate into effector cells. Instead, effective immunity was only induced when the test vaccine provided antigen and adjuvant to the same individual DCs within a short window of time. These parameters are fulfilled when the antigen and adjuvant are linked in time and space as parts of the very same molecule, as provided by the instant invention.

To fulfill the need for a vaccine that induces a strong CD8+ T cell responses, the instant invention provides for a composition that contains, for example, CD40 ligand (CD40L, TNFSF5, which is an agonist of the CD40 receptor) physically linked to a multimerization domain that organizes it into a highly active many-trimer structure in addition to being physically linked to an antigen. In this way, antigen can be targeted to dendritic cells via binding to the CD40 receptor on their surface and activates the dendritic cell simultaneously. This arrangement can thus avoid delivery of antigen to dendritic cells that do not become activated and which instead would induce antigen-specific CD8+ T cell tolerance. As a result, the compositions of the instant invention provide for a unusually high level of activity in inducing strong CD8+ T cell responses, where the TCRs of elicited CD8+ T cells show an exceptionally high level of avidity for pMHC-I and where a vaccine of the invention confers surprisingly profound protection from challenge by an infectious agent (Vaccinia encoding HIV-1 Gag as a model antigen). Variations on these compositions are expected to elicit very strong CD4+ T cells and B cell antibody responses in a similar fashion.

SUMMARY OF THE INVENTION

The invention provides fusion proteins comprising antigens of infectious disease agents and cancer cells linked to many-trimer forms of TNF SuperFamily (TNFSF) ligands. The TNFSFs serve as vaccine adjuvants for increasing the immune response to the antigens. In particular, a fusion polypeptide strand that self-assembles inside cells into a many-trimer form of CD40 ligand (CD40L, TNFSF5) was shown to elicit surprisingly strong responses against an infectious disease agent and a tumor antigen. Other similar fusion proteins are contemplated and their construction provided for in the application. The fusion proteins can be delivered to a host either as nucleic acids used directly in DNA vaccination or carried and expressed by a viral vector such as adenovirus. It is contemplated that isolated fusion proteins could be also be administered with good effect. In addition to use as a vaccine to prevent or ameliorate disease caused by an infectious agent, compositions of the invention may be used for the treatment of ongoing infection or for cancer immunotherapy.

To create a vaccine that effectively elicits strong CD8+ T cell responses, highly active forms of TNF Superfamily ligands (TNFSFs) were constructed as fusion proteins with test antigens from infectious disease agents and tumors. Using CD40 ligand (CD40L, also called TNFSF5) as an exemplary TNFSF, the resulting fusion proteins were given to mice in the form of a DNA vaccine (by injection of plasmid DNA into muscle) as a means to deliver antigen to dendritic cells and activate these cells through their CD40 receptor at the same time. This approach minimizes the separate delivery of antigen to dendritic cells that have not been activated by adjuvant, which would otherwise result in CD8+ T cell tolerance as shown by Bonifaz et al. 0 Exp Med. 2002; 196(12):1627-38. PMCID: 2196060) and Kamath et al. (J Immunol. 2012; 188(10):4828-37). In the exemplary case, this invention combines one of the best vaccine adjuvants for dendritic cell activation (i.e., CD40L) along with targeting the antigen to dendritic cells by virtue of the antigen being operatively linked to CD40L (the ligand for the CD40 receptor) which binds to CD40 and delivers the antigen to dendritic cells for cross-presentation as pMHC-I. Previous attempts to link CD40L with antigen were flawed by defective molecular design and did not result in such a powerful vaccine. Instead, the approach of the instant invention provides a combination in such a way as to provide a surprisingly strong CD8+ T cell response that is highly protective. By selecting the appropriate antigen(s) and TNFSFs and an appropriate delivery method, applications include vaccines against infectious agents and malignant cells. Using fusion proteins directly or as their encoding nucleic acid sequences delivered by a DNA or RNA vaccine or by a viral vector such as adenovirus, the invention has substantial industrial application.

CD40L plasmid on day 3, 10, and 17. GVAX, B16F10 tumor cells expressing GM-CSF, were irradiated at 5,000 rad and 1×10 E6 cells injected subcutaneously on day 3, 6, and 9. Panel B: Tumor growth analysis. Each point represents the mean tumor volume in each group (n=5). We did not observe a statistical difference in tumor sizes between no treatment (PBS) and SPD-gp100-CD40L vaccination groups. Panel C: Survival analysis based on the date of death or when tumor size reached >1500 cm2. No statistical differences in survival were observed between groups.

Figure 16:
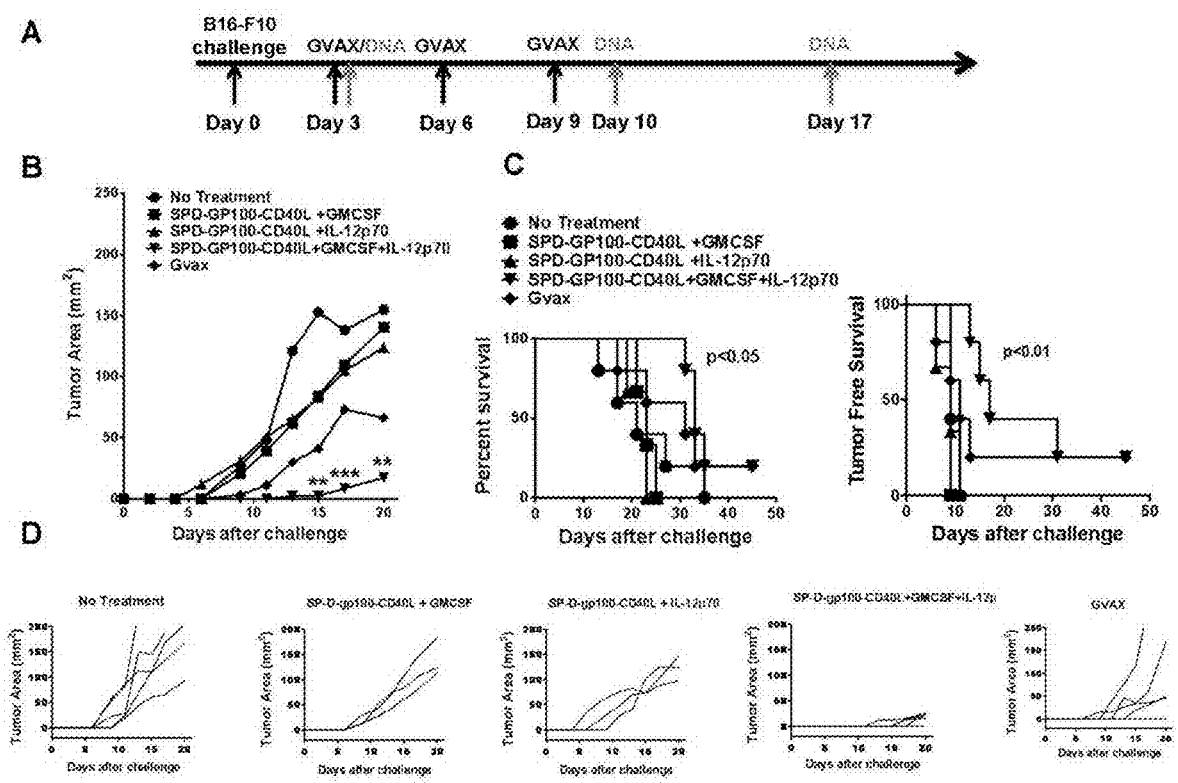

FIG. 16: Immunotherapy of established B16F10 melanoma tumors by DNA vaccination with a combination of pSPD-gp100-CD40L, pIL-12p70 and pGM-CSF. Panel A: Immunization schedule for B16F10 tumor challenge and DNA/GVAX vaccination, as indicated by arrows. B16F10 cells (50,000) were injected i.d. into the left flank of the mice on day 0. Mice were immunized i.m. with PBS, pSPD-gp100-CD40L pIL-12, pSPD-gp100-CD40L pGM-CSF, or pSPD-gp100-CD40L pIL-12 pGM-CSF on day 3, 10, and 17. For GVAX therapy B16-F10 tumor cells expressing GM-CSF (GVAX), were irradiated at 5,000 rad and 1×106 cells were injected subcutaneously on day 3, 6, and 9. Panel B: Tumor growth analysis. Each point represents the mean tumor volume of animals in each group (n=5). There was a significant reduction in tumor growth kinetics for SPD-gp100-CD40L+pIL-12 GM-CSF vaccinated mice compared to other groups. ( $p<0.01$; * $p<0.001$ compared to PBS or SPD-gp100-CD40L+pIL-12 or SPD-gp100-CD40L GM-CSF vaccination groups). Panel C: Survival analysis of mice. We observed a significant increase in survival and tumor free survival (date of tumor appearance) for pSPD-gp100-CD40L pIL-12 pGM-CSF vaccinated mice as compared to other groups ( $p<0.01$; * $p<0.001$ compared to PBS, pSPD-gp100-CD40L pIL-12, or pSPD-gp100-CD40L pGM-CSF vaccination groups). Panel D: Tumor growth kinetics of individual mice from each treatment group.

Figure 17:
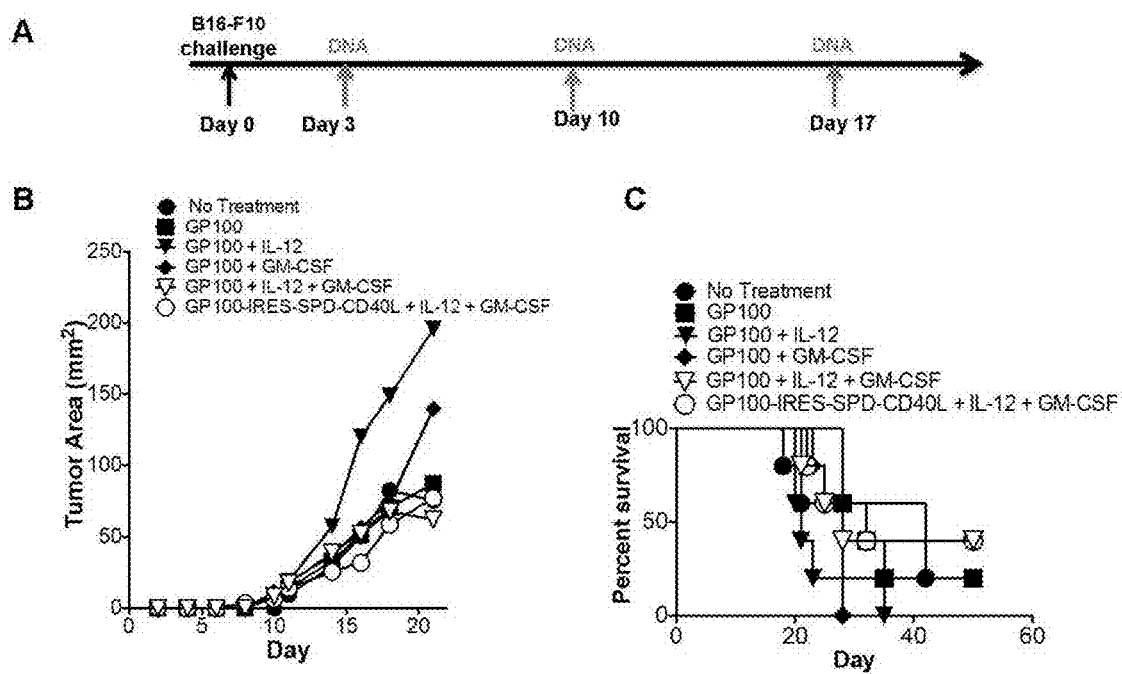

FIG. 17: Separate expression of gp100 and SPD-CD40L proteins fails to induce anti-tumor activity. As a control for pSPD-gp100-CD40L, several other anti-tumor treatment approaches were tested and found to be inferior. Panel A: Immunization schedule for B16F10 tumor challenge and DNA vaccination, as indicated by arrows. B16-F10 cells (50,000) were injected into the left flank of the mice on day 0. Mice were immunized i.m. with PBS, pgp100, pgp100 pIL-12, pgp100 pGM-CSF, pgp100 pIL-12 pGM-CSF, or pgp100-IRES-SPD-CD40L pIL-12 pGM-CSF on day 3, 10, and 17. Panel B: Tumor growth analysis. Each point represents the mean tumor volume of animals in each group (n=5). We did not observe any statistical difference in tumor size between vaccination groups. Panel C: Survival analysis. We did not observe any statistical difference in survival of mice between groups.

BRIEF DESCRIPTION OF THE SEQUENCES

SEQ ID NO 1: DNA sequence for muSP-D-Gag-muSP-D-muCD40L. This is the DNA sequence of a fusion protein using the murine sequences for SPD and CD40L. Due to minor differences between species, it is preferable to use a murine sequence for administration to mice, a macaque sequence for administration in monkeys (Stone et al., Clin Vaccine Immunol. 2006; 13(11):1223-30), a human sequence for administration to humans, and so. This minimizes the possibility of antibodies forming against a xenogeneic protein, other than the antigen contained in the construct. In this example, what is shown is the nucleic acid sequence used for the experiments shown in FIGS. 6-12. (Note that surfactant protein D is variously abbreviated as either 'SPD' or 'SP-D'. The location of the Gag antigen insert is shown in non-italicized type face.

SEQ ID NO 2: Protein sequence for muSP-D-Gag-muSP-D-muCD40L. This is the translation of SEQ ID NO 1.

SEQ ID NO 3: DNA sequence for tpa-muACRP30-gp120-muACRP30-muBAFF. This is a DNA sequence of a fusion protein using the previously described 2-trimer form of Acrp30-BAFF into which has been inserted a DNA sequence of HIV-1 gp120 envelope as an antigen. It is contemplated that the 2-trimer fusion protein encoded by this nucleic acid sequence will activate the Env gp120-binding B cell receptor (BCR) on B cells and simultaneously engage receptors for BAFF on these B cells that synergize with BCR engagement to stimulate the B cell to produce anti-Env antibodies.

SEQ ID NO 4: Protein sequence for tpa-muACRP30-gp120-muACRP30-muBAFF. This is the translation of SEQ ID NO 3.

SEQ ID NO 5: DNA sequence for muSP-D-gp100-muSP-D-muCD40L. This is the DNA sequence of a fusion protein using the murine sequences for SPD and CD40L. The inserted antigen (non-italicized sequence) is encoded by the nucleotide sequence for human gp100, a xenogenic antigen that has been found to be useful in melanoma studies in mice (Gold et al., J Immunol. 2003; 170(10):5188-94).

SEQ ID NO 6: Protein sequence for muSP-D-gp100-muSP-D-muCD40L. This is the translation of SEQ ID NO 5.

SEQ ID NO 7: DNA sequence for tpa-huIgG1Fc-gp120-GCN4-huAPRIL. This is a DNA sequence encoding a human t-PA signal sequence for protein secretion joined in-frame with the human IgG1 Fc region joined in-frame with HIV-1 Env gp120 joined in-frame with the GCN4 trimerization motif joined in-frame with the extracellular domain of human APRIL. It is contemplated that the 2-trimer fusion protein encoded by this nucleic acid sequence will activate the Env gp120-binding B cell receptor (BCR) on B cells and simultaneously engage receptors for APRIL on these B cells that synergize with BCR engagement to stimulate the B cell to produce anti-Env antibodies.

SEQ ID NO 8: Protein sequence for tpa-huIgG1Fc-gp120-GCN4-huAPRIL. This is the translation of SEQ ID NO 7.

SEQ ID NO 9: DNA sequence for huSP-D-NP-huSP-D-huCD40L-NST. It was previously found that some embodiments of SPD-CD40L can be equally or more active when the extracellular "stalk" region of CD40L is deleted. This stalk links the CD40L trimeric extracellular domain (ECD) with the transmembrane region that holds CD40L in the membrane. The SPD-CD40L-NST construct is disclosed in US 2009/0081157 A1 (see especially FIG. 21, Examples 1, 11, and 13) which is incorporated by reference. The instant sequence comprises an insertion of coding sequences for the nucleoprotein (NP) antigen from influenza A. It is contemplated that the 4-trimer fusion protein encoded by this nucleic acid sequence will elicit strong CD8+ T responses against this conserved influenza antigen.

SEQ ID NO 10: Protein sequence for huSP-D-NP-huSP-D-huCD40L-NST. This is the translation of SEQ ID NO 9.

SEQ ID NO 11: DNA sequence for tpa-muACRP30-CSP1-muACRP30-muCD40L. This is a DNA sequence encoding a human t-PA signal sequence for protein secretion joined in-frame with a portion of the murine Acrp30 sequence joined in-frame with codons for the circumsporozoite protein-1 (CSP-1) of *Plasmodium yoelii* joined in-frame with a portion of the murine Acrp30 sequence joined in-frame with the extracellular domain of murine CD40L. *Plasmodium yoelii* is used for malaria vaccine studies because it causes a malaria-like disease in mice. CD8+ T cells directed against the CSP-1 antigen of this agent can provide immunity to malaria (Sedegah et al., Proc Natl Acad Sci USA. 1998; 95(13):7648-53). It is contemplated that mice vaccinated with this construct will be resistant to disease caused by intravenous challenge with *Plasmodium yoelii*-infected red blood cells.

SEQ ID NO 12: Protein sequence for tpa-muACRP30-CSP1-muACRP30-muCD40L. This is the translation of SEQ ID NO 11.

SEQ ID NO 13: DNA sequence for muSP-D-Gag-muSP-D-muRANKL. This is a DNA sequence encoding a portion of the murine SPD sequence joined in-frame with codons for HIV-1 Gag antigen joined in-frame with a portion of the murine Acrp30 sequence joined in-frame with the extracellular domain of murine RANKL. Of special note is the difference of position in placing the antigen within the sequence of the SPD "arms," in this case shifted toward the 5' end (or N-terminal end in the protein) the equivalent of 10 codons in the SPD sequence. It is contemplated that this construct used as a vaccine will elicit strong immune responses in mice.

SEQ ID NO 14: Protein sequence for muSP-D-Gag-muSP-D-muRANKL. This is the translation of SEQ ID NO 13.

SEQ ID NO 15: DNA sequence of huSP-D-WT1-huSP-D-huCD40L. This is a DNA sequence encoding a portion of the human SPD sequence joined in-frame with codons for the human WT1 protein joined in-frame with a portion of the human SPD sequence joined in-frame with the extracellular domain of human CD40L. WT1 is a tumor antigen present in many types of human cancer (Chaise et al., Blood. 2008; 112(7):2956-64). It is contemplated that this construct used as a vaccine will elicit strong immune responses in humans against cancer cells expressing the WT1 tumor antigen.

SEQ ID NO 16: Protein sequence for huSP-D-WT1-huSP-D-huCD40L. This is the translation of SEQ ID NO 15.

SEQ ID NO 17: DNA sequence of muSP-D-MAGE-A3-muSP-D-muBAFF. This is a contemplated DNA sequence encoding a portion of the murine SPD sequence joined in-frame with codons for the human MAGE-A3 tumor antigen (Groeper et al., Int J Cancer. 2007; 120(2):337-43) joined in-frame with a portion of the murine SPD sequence joined in-frame with the extracellular domain of murine BAFF. Of note is that codons for 20 amino acids (PPGLPGIPGPMGARASVLSG) in the N-terminal half of the SPD arm have been deleted. This exemplifies how the SPD "arms" can be shortened N-terminal to the insertion site of the antigen sequence. Similar deletions in the C-terminal half of the SPD arm are also contemplated, as are deletions in both sides of the SPD arms that flank the antigen sequence insertion site.

SEQ ID NO 18: Protein sequence of muSP-D-MAGE-A3-muSP-D-muBAFF. This is the translation of SEQ ID NO 17.

Definitions

This disclosure uses art-recognized concepts and methods. The skilled artisan will be familiar with resources including the following: "Janeway's Immunology" by Kenneth Murphy, Garland Science Press, 2011; "Fundamental Immunology" by William E. Paul, Lippincott Williams & Wilkins, 2008; "Cellular and Molecular Immunology, 7th Edition" by Abul K. Abbas, Andrew H. H. Lichtman, and Shiv Pillai, Elsevier Press, 2011; "Current Protocols in Immunology," Wiley Press, 2012; and "Current Protocols in Molecular Biology," Wiley Press, 2012. In addition, the following patents and applications are incorporated by reference: U.S. Pat. No. 7,300,774B1; U.S. Pat. No. 7,332,298 B2; US 2009/0081157 A1.

Unless otherwise explained, all technical and scientific terms used herein have the same meaning as commonly understood by one of ordinary skill in the art to which this disclosure belongs. Definitions of common terms in molecular biology can be found in Benjamin Lewin, Genes V, published by Oxford University Press, 1994 (ISBN 0-19-854287-9); Kendrew et al. (eds.), The Encyclopedia of Molecular Biology, published by Blackwell Science Ltd., 1994 (ISBN 0-632-02182-9); and Robert A. Meyers (ed.), Molecular Biology and Biotechnology: a Comprehensive Desk Reference, published by VCR Publishers, Inc., 1995 (ISBN 1-56081-569-8).

In order to facilitate review of the various embodiments of this disclosure, the following explanations of specific terms are provided:

The singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of this disclosure, suitable methods and materials are described below. The term "comprises" means "includes." The abbreviation, "e.g." is derived from the Latin exempli gratia, and is used herein to indicate a non-limiting example. Thus, the abbreviation "e.g." is synonymous with the term "for example."

"C1q family protein" refers to a member of the C1q family. Exemplary C1q family proteins include, but are not limited to, C11, Acrp30, and HIB27. Preference is given to Acrp30. Like the collectins, C1q family members have 2 or more trimeric, collagen-like "arms" that provide the multivalent structures of these molecules. The instant invention utilized C1q family proteins as a multimerization scaffold by replacing their normal C-terminal "C1q" domains with a TNFSF receptor binding such as the ECD of a TNFSF ligand.

"Collectin" refers to a member of the collectin family. See URL http://en.wikipedia.org/wild/Collectin for a listing of collectins and their gene names. They include pulmonary surfactant A, pulmonary surfactant D, conglutinin, collectin-43, mannose-binding protein MBL1 or MBL2, and others. Preference is given to surfactant protein D (abbreviated alternatively as SP-D or SPD). All collectins have two or more trimeric collagen-like "arms" joined in the center at a "hub" and radiating outward to display their C-terminal ends. Each collectin has a C-terminal domain that typically binds to carbohydrate. When used as a multimerization scaffold in the instant invention, each collectin is made without the natural C-terminal end and a TNFSF ECD receptor binding domain is placed there instead. Preference is given to surfactant protein D which has four trimeric arms ending C-terminally.

"Complete TNFSF receptor" is a term used herein in marked distinction to a single polypeptide chain often referred to as a TNFSF receptor protein (see URL http://www.genenames.org/genefamilies/TNFRSF for a listing of TNFSF receptors (also called TNFRSFs) and their gene names. The nucleotide and peptide sequences of single TNFSF receptor polypeptide chains are listed in GenBank, SwissProt, and other databases. However, in actuality, single TNFSF receptor polypeptide chains are not found in isolation on the surface of cells. Instead, two or more TNFSF receptor chains are co-localized or linked. As an example, the Fas receptor (CD95) for Fas ligand (FasL) is held together in the absence of FasL by their N-terminal "pre-ligand association domains" or PLAD (Siegel et al., Science. 2000; 288(5475):2351-4). Similarly, there is a domain in the extracellular region of CD40 that holds this receptor together as 2 or more chains (Smulski et al., J Biol Chem. 2013). Consequently, stimulation of TNFSF receptors generally does not involve simple bringing together of 2 or more receptor chains. When the ligand does bind to the receptor, computer modeling suggests that a ligand trimer engages three receptor chains (Bajorath et al., Biochemistry. 1995; 34(31):9884-92). Thus, this application uses the term "complete TNFSF receptor" to indicate that binding to a TNFSF receptor involves binding to 2 or preferably 3 receptor protein chains.

"Immune system" refers to T cells, B cells, NK cells, dendritic cells, monocytes, and macrophages and the specialized tissues that contain them. The lymph nodes, lymphatics, and spleen are physical structures that housing many of the cells of the immune system. In addition, other immune system cells are found in non-lymphoid tissues and in blood. A characteristic of the immune system is that it responses to a first exposure to an antigen (primary response) in a set fashion but then responds more strongly and more quickly to a second exposure of an antigen (secondary response), which is a manifestation of immunological memory. The immune system responds to infectious agents and cancer by producing cells and effector molecules that kill the offending infectious agent or cancer cells. Among the cells that kill the attackers are T cells including CD4+ and CD8+ T cells. B cells make antibodies that can neutralize the infectivity of many infectious agents. T cells, monocytes, macrophages, and dendritic cells can make interferons that interfere with the replication of certain viruses.

"Multimerization scaffold" refers to a molecular structure that confers upon the molecule into which it is incorporated an overall structure that is operatively linked to two or more TNFSF receptor binding domains, such that contact with the multimerized molecule leads to clustering of the complete TNFSF receptor in the membrane of a responding cell and thereby activates some or all of the functional potential of the responding cell. A key concept of the instant invention is that a many-trimer form a TNFSF ligand is needed to stimulate a receptor-bearing responding cell. For example, structural studies of the GITRL/GITR interaction indicate that two closely localized trimers of GITRL are needed to bring together or "cluster" two complete GITR receptor (3 chains of GITR each) (Zhou et al., Proc Natl Acad Sci USA. 2008; 105(14):5465-70). A multimerization scaffold is a molecular structure that provides for this close localization of 2 or more TNFSF receptor binding, typically 2 or more TNFSF ligand extracellular domains (ECD). In the instant invention, portions of collectins such as SPD or portions of C1q family members such as Acrp30 are used to make single polypeptide chains that self-assemble into multimerization scaffolds. Preference is shown for multimerization scaffolds that have "arms" capable of being operatively linked to TNFSF ECD trimers. Alternative embodiments are contemplated, such as multimerization scaffold that is operatively linked to single-chain antibodies that bind to a TNFSF receptor.

"Operatively linked" refers to a method for joining two molecules. For polypeptides, this is preferably by a peptide bond, typically achieved by constructing a DNA or RNA template encoding the operatively linked fusion protein and then expressing the DNA or RNA in a cell or by an in vitro method. In some case, chemical crosslinkers can be used to construct multimeric forms of TNFSF receptor binding agents as described in U.S. Pat. No. 6,482,411 B1 which is incorporated by reference.

"TNFSF" refers to a ligand in the Tumor Necrosis Factor (TNF) SuperFamily. See URL http://www.genenames.org/genefamilies/TNFSF for a listing of TNFSFs and their gene names. The TNFSFs are produced as trimeric Type II membrane molecules meaning that their N-terminus points inside the cell and their C-terminal end is extracellular, which is the reverse of most cell surface proteins. This makes these proteins very challenging to engineer using traditional fusion protein strategies.

"TNFSF receptor binder" refers to a molecular fragment that binds to a TNFSF receptor. Exemplary TNFSF receptor binders (or binding domains) include the extracellular domain (ECD) of a TNFSF trimeric molecule or the receptor-binding portion of an antibody recognizing a TNFSF receptor. For a receptor-binding portion of an antibody, preference is give to single-chain antibody constructs (Ahmad et al., Clin Dev Immunol. 2012; 2012:980250. PMCID: 3312285). Exemplary TNFSF members whose extracellular domains can be used as TNFSF receptor binders include CD40L (TNFSF5), CD27L (TNFSF7), CD137L (TNFSF9), OX40L (TNFSF4), GITRL, 4-1BBL, RANKL, LIGHT, CD70, and BAFF.

"Tumor antigens" refers to proteins, carbohydrates, or lipids found on tumor cells against which the immune system can launch an attack. For a discussion of tumor antigens, see Kvistborg et al. (Curr. Opinion Immunol. 25:284-290, 2013) and Cheever et al. (Clin Cancer Res 15, 5323-5337, 2009). Also contemplated as tumor antigens are antigenic peptides deduced from next-generation sequencing from the RNA or DNA of tumors, including exome sequencing (Segal et al., Cancer Res. 2008; 68(3):889-92; Castle et al., Cancer Res. 2012; 72(5):1081-91).

DETAILED DESCRIPTION OF THE INVENTION

This invention describes, inter alia, molecules comprising fusion proteins and the nucleic acids that encode them in which the following protein coding domains are operably linked in the following order: a scaffold comprised of a portion of a collectin or C1q family protein or combinations of dimerizing/trimerizing motifs, an antigen (either following the scaffold or contained within the scaffold), and the extracellular domain of a TNF superfamily ligand. An exemplary fusion protein or nucleic acid that encodes it comprises the antigen, surfactant protein D (SPD) without its carbohydrate receptor domain, and the extracellular domain of CD40 ligand. Alternatives to surfactant protein D can also be used, including using immunoglobin (Ig), Acrp30, a GCN4 multimerization motif, or similar proteins as scaffolds for CD40 ligand, other members of the TNF superfamily ligands, or other ligands or receptors, including gp96 or MHC molecules. In one embodiment, the molecules, compositions and/or fusion proteins of the invention do not contain portions of avidin or streptavidin.

These fusion proteins are designed to allow the targeting of dendritic cells, macrophages, B cells or other antigen presenting cells with the antigen as well as providing necessary activation signals to induce maturation of the targeted dendritic cell, macrophage, B cell or other antigen presenting cell. This results in the optimal presentation of the antigen to the immune system, and a potent immune response in the treated individual, either T cell mediated or antibody mediated.

In more detail, the instant invention provides a solution for the problem of vaccinating against infectious agents and for cancer immunotherapy. It provides a way to link an adjuvant in the TNF SuperFamily (TNFSF) to an antigen such that the TNFSF adjuvant and antigen arrive at the same cell at the same time. In the case of CD8+ T cell responses, it is important to provide antigen to dendritic cells (DCs) and other antigen-presenting cells such that the protein antigen is processed by cleavage into peptides and loaded onto MHC-I for cross-presentation on the cell surface as pMHC-I complexes which in turn stimulates the T cell receptor (Signal 1). It is preferable to target the antigen to the CD40 receptor on DCs since this results in superior cross-presentation by a larger number of DC subtypes (Chatterjee et al., Blood. 2012; 120(10):2011-20). In addition, it is important to activate the DC that is presenting antigen in order that the DCs present the antigen-specific T cell with accessory signals (Signal 2 and Signal 3). If the DCs display only pMHC-I and are not activated to present other signals, then the resulting antigen-specific CD8+ T cell becomes tolerant and lacks protective effective functions (Bonifaz et al., J Exp Med. 2002; 196(12):1627-38. PMCID: 2196060). Stimulation of the CD40 receptor on DCs activates the DCs to provide these other signals and leads to profound CD8+ T cell responses (Bonifaz et al., J Exp Med. 2004; 199(6):815-24). Thus, the instant invention provides a strong vaccine for CD8+ T cells by fusing antigen to previously described multimeric forms of CD40L comprised of the extracellular domain (ECD) of CD40L fused to multimerization scaffolds employing portions of surfactant protein D (SPD) or Acrp30.

Figure 1:
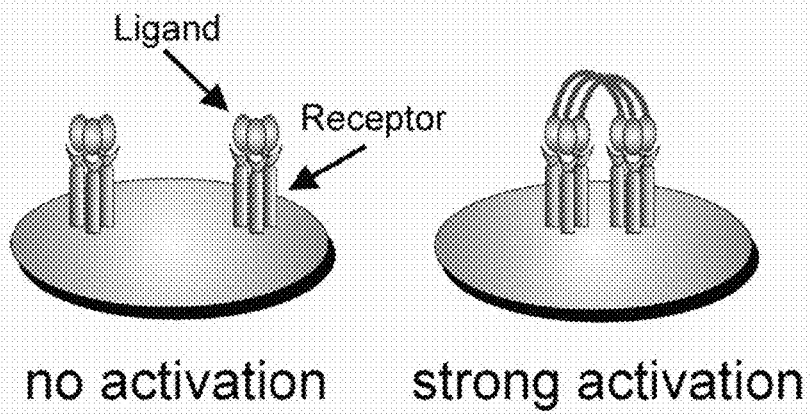
FIG. 1: Schematic drawing illustrating the need to cluster a TNFSF receptor such as the CD40 receptor on dendritic cells and other APCs in order to provide a strong cell stimulus. This requirement for clustering affects the design of an effective form of TNFSF ligand or an anti-TNFSF receptor-binding antibody.

Activation of DCs and other APCs is best performed by a many-trimer form of CD40L where 2 or more trimers are needed to cluster and thereby activate the CD40 receptors on DCs, as depicted in FIG. 1.

Figure 2:
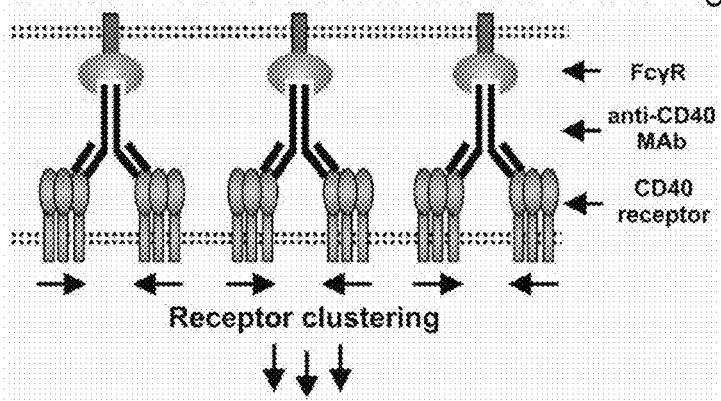
FIG. 2: Agonistic anti-CD40 antibodies can cluster CD40 receptors so long as they bind to and are "mounted" on a nearby cell that expresses receptors for the Fc tail of the antibody molecule. Abbreviations: FcγR—the receptor for the Fc portion of immunoglobulin G (IgG). Anti-CD40 MAb—a monoclonal antibody that binds to CD40.

The new understanding of agonistic anti-TNFSF receptor antibodies is shown in FIG. 2. In this case, the antibody is first bound to an adjacent cell via its Fc portion which binds to the Fc receptors on the adjacent cell type (Li and Ravetch, Science. 2011; 333(6045):1030-4. PMCID: 3164589; Wilson et al., Cancer Cell. 2011; 19(1):101-13; White et al., J Immunol. 2011; 187(4):1754-63). This leads to two problems: (1) DCs and other APCs that are not adjacent to an FcR-bearing cell cannot be stimulated; and (2) if the antibody binds to certain FcRs, then it is possible that the adjacent cell will kill the DC by antibody-dependent cellular cytotoxicity (ADCC) or phagocytose the DC and eliminate it (Bulliard et al., J Exp Med. 2013; 210(9):1685-93. PMCID: 3754864). The later phenomenon may explain the severe depletion of CD40 B cells when an antibody against CD40 was tested in humans with cancer (Vonderheide et al., J Clin Oncol. 2007; 25(7):876-83). These considerations set the stage for a new and better way to provide both antigen and CD40 stimulation to DCs and other APCs.

Another approach was taken by Xiang et al. (J Immunol. 2001; 167(8):4560-5) who made a fusion protein of tumor antigen (CEA) joined to the C-terminal end of CD40L (U.S. Pat. No. 7,279,464 B2; U.S. Pat. No. 6,923,958 B2). However, because the CD40L moiety is not located on the end of the protein, it could conceivably have impaired binding of the ligand to the CD40 receptor. No data were presented to rule out this concern, but the vaccine's effectiveness was modest.

In a related approach, Zhang et al. (Proc Natl Acad Sci USA. 2003; 100(25):15101-6) fused a tumor antigen onto the N-terminus of the CD40L extracellular domain and delivered this construct using an adenovirus vector. In this case, the molecular design allowed for CD40L to bind unimpaired to its receptor. Even so, the effectiveness of this vaccine was relatively modest. This is expected when a 1-trimer form of CD40L is used rather than a receptor-clustering multi-trimer construct such as SPD-Gag-CD40L.

Another approach was taken by Shirwan et al. who produced a fusion protein between the "core" region of bacterial streptavidin protein (CSA) and the extracellular domain of CD40L or 4-1BBL, as disclosed in U.S. Pat. No. 8,017,582 B2 and in Schabowsky et al., Exp Mol Pathol. 86:198-207, 2009. In this case, the N-terminal half of the fusion proteins consisted of CSA where streptavidin naturally assembles into a 4-chain molecule. This multimerism pulls together the covalently linked ECDs for CD40L or 4-1BBL. Since streptavidin binds to biotin and since proteins can be easily biotinylated, it was possible to biotinylate antigens such as chicken ovalbumin (OVA) or the tumor antigens E7 from HPV which allows them to bind non-covalently to CSA-CD40L or CSA-4-1BBL. However, in order to be active, CD40L must be used in a multi-trimer form that clusters together two or more CD40 receptors, as depicted in FIG. 1 of the instant application. The relative inactivity of a single trimer form of CD40L was demonstrated by Haswell et al. (Eur J Immunol. 31:3094-3100, 2001; see FIG. 3). In contrast, the CSA-CD40L forms a single trimer of CD40L, as depicted in FIG. 1B of Schabowsky et al., which is not desirable from the perspective of efficient receptor stimulation. Furthermore, the biotin-streptavidin interaction in the design of Shirwan et al. is non-covalent. The antigen has been biotinylated which then allows it to bind to the streptavidin moiety in the CSA-CD40L complex. However, in vivo, there is free biotin present in biological fluids that can interfere with the formation of the CSA-CD40L/biotin-antigen complex or induce its dissociation. In contrast, the instant invention utilizes antigen that has been covalently joined to CD40L by virtue of the peptide bonds that make up the SPD-antigen-CD40L fusion protein and thus the protein is not susceptible to dissociation in the presence of free biotin. Another important difference is that CSA is a xenogenic protein from bacteria that is highly antigenic in humans and other vertebrates (Meyer et al. Protein Science 2001; 10(3):491-503; Yumura et al., Protein Science 2013; 22(2):213-21). In contrast, the fusion proteins of the instant invention can be constructed with primarily non-xenogenic proteins sequences such that the only major foreign protein component is the antigen selected for immunization. Therefore, in one embodiment of the present invention, the multimerization scaffold and the plurality of TNFSF receptor binder do not contain any xenogenic portions.

Another system for producing many-trimer forms of OX40L was described by Weinberg et al. in U.S. Pat. No. 7,959,925 B2, which is incorporated by reference. In this system, fusion proteins are made by using an N-terminal immunoglobulin Fc domain which naturally dimerizes via interchain disulfide bonds. When this is joined to a trimerizing domain which is then joined to a TNFSF extracellular domain, it results in what is described as a hexamer or "dimer of trimers". In the instant invention, SEQ ID NO:7 and SEQ ID NO:8 disclose a fusion protein that provides for a 2-trimer form of APRIL fused to the HIV-1 Env protein which is expected to elicit a strong antibody response to HIV-1. The skilled artisan will easily see how the extracellular domain of APRIL could be replaced by the extracellular domain of any other TNFSF ligand, and also how the HIV-1 Env antigen could be replaced by other antigens of interest. Such antigen-multimeric TNFSF fusion proteins are claimed by the instant invention. In addition, the skilled artisan could envision other dimerizing domains (such as that from CD4 or CD8) or other trimerizing domains (such as those from GCN4, TRAF2, thrombospondin 1, Matrilin-4, CMP (Matrilin-I), HSFI, or cubulin, as described in U.S. Pat. No. 7,959,925 B2) or the trimerizing domain from the SPD "neck" region in U.S. Pat. No. 6,190,886, which is incorporated by reference.

Figure 3:
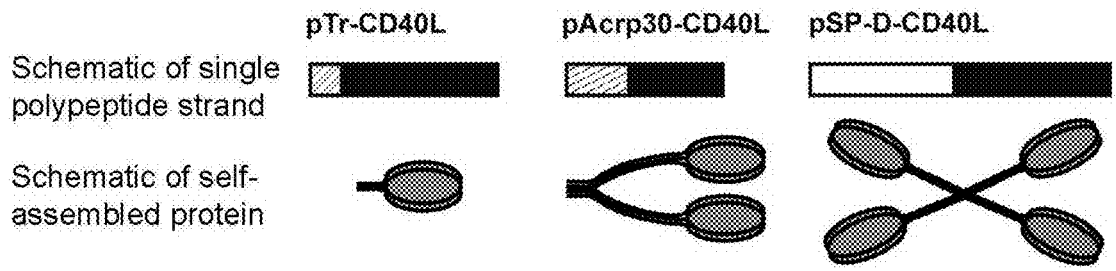
FIG. 3: Molecular design of fusion proteins that create many-trimer forms of soluble CD40L. On the left is a schematic for a 1-trimer form of CD40L that cannot cluster the CD40 receptor and as a result is inactive, as shown by Haswell et al. (Eur J Immunol. 2001; 31(10):3094-100) and Holler et al. (Mol Cell Biol. 2003; 23(4):1428-40) and described in EP 1246925 B1. As previously described (Stone et al., J Virol. 2006; 80(4):1762-72) and presented in U.S. Pat. No. 7,300,774 B1 and U.S. Pat. No. 7,332,298 B2, and also in EP 1246925 B1, the extracellular domain (ECD) of CD40L can be genetically fused to scaffold-forming proteins such as Acrp30 (middle) or surfactant protein D (SPD) (right). The 2-trimer Acrp30-CD40L protein is also called MegaCD40L™ or CD40L hexamer, whereas the 4-trimer SP-D-CD40L protein is also called UltraCD40L™. These many-trimer forms of CD40L can cluster the CD40 receptor and act as a vaccine adjuvant. This occurs in part by activating dendritic cells (Miconnet and Pantaleo, Vaccine. 2008; 26(32):4006-14).
Figure 4:
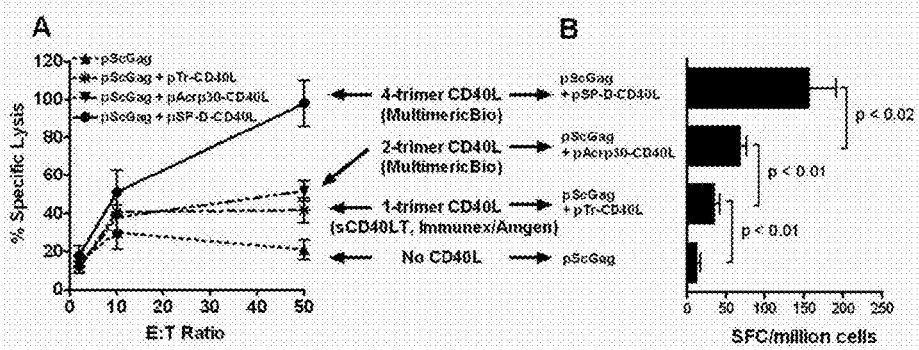
FIG. 4: Two- and four-trimer CD40L fusion proteins are vaccine adjuvants for CD8+ T cell responses. Mice were vaccinated by injecting "naked" plasmid DNA into muscle in order to test different forms of CD40L as an adjuvant for the HIV-1 Gag antigen. In Panel A, CD8+ T cell responses were detected as killing of P815 target cells pulsed with Gag peptide. In Panel B, CD8+ T cell responses were detected by measuring the number of individual interferon-gamma secreting cells in response to Gag peptide antigen using an ELISPOT assay. There was a distinct improvement in CD8+ T cell responses using a 2-trimer form of CD40L (Acrp30-CD40L) and more preferably a 4-trimer form of CD40L (SPD-CD40L) (Stone et al., J Virol. 2006; 80(4):1762-72). To show the general applicability of this approach, a similar vaccine assay system was used to show that other TNFSF ligands could be multimerized as 4-trimer proteins and used as vaccine adjuvants, including GITRL, 4-1BBL, OX40L, RANKL, LIGHT, CD70, and BAFF (Kanagavelu et al., Vaccine. 2012; 30(4):691-702. PMCID: 3253891).
Figure 5:
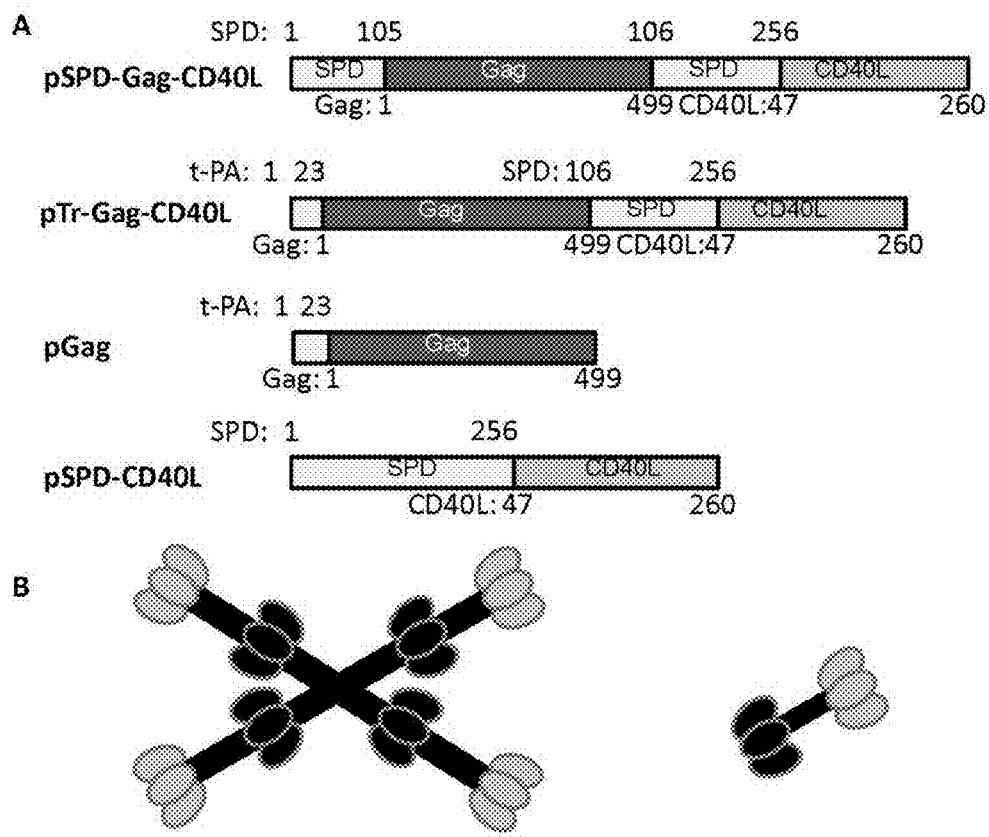
FIG. 5: Molecular design of multimeric CD40L fusion proteins containing an in-frame insertion encoding HIV-1 Gag as a model antigen. Top: pSPD-Gag-CD40L is a plasmid containing an antigen inserted into the protein strand that results in a 4-trimer form of CD40L. At the nucleic acid level, the codons for a model antigen, HIV-1 Gag, were positioned into the coding sequence of the SPD-CD40L construct. In the resulting translated protein, the N-terminus is comprised of a secretion signal peptide from SPD followed by an N-terminal sequence of SPD termed the "hub" which contains 2 cysteines in each strand, thereby producing disulfide bonds that (a) covalently couple three individual polypeptide strands together to form an "arm" and (b) covalently couple 4 trimeric arms into the final 12-chain, 4-arm structure shown in the bottom left of the figure (where the inserted Gag antigen is shown as a solid bulge in each arm of the protein). Note that the Gag antigen sequence was positioned between the 105 and 106 amino acids of murine SPD protein, while retaining the previously constructed CD40L domain at the C-terminal end. Like the parent SPD-CD40L molecule, this protein strand of SPD-Gag-CD40L spontaneously self-assembles inside cells into a multimeric, many-trimer form of CD40L that is then secreted into the extracellular space. 2nd from Top: pTrimer-Gag-CD40L (labeled pTr-Gag-CD40L) is a plasmid constructed by deleting codons for amino acids 24-105 of murine SPD. This removes the hub region containing the 2-cysteines. Also included is the t-PA signal peptide sequence for secretion. This results in the production of a single-trimer, 1 "arm" form of the Gag antigen-CD40L protein, as shown in the bottom right of the figure (where the Gag antigen is shown as a solid bulge in this 1-trimer form of CD40L). 3rd from Top: pGag is the plasmid encoding amino acids for the p55 Gag antigen preceded by the t-PA signal sequence for secretion, as described by Qiu et al. (J Virol. 1999; 73(11):9145-52). This is a control antigen construct that has no CD40L adjuvant. 4th from Top: pSPD-CD40L is the plasmid encoding a 4-trimer form of CD40L previously described by Stone et al. (J Virol. 2006; 80(4): 1762-72) and in U.S. Pat. No. 7,300,774 B1 and U.S. Pat. No. 7,332,298 B2. This is an adjuvant-only protein that does not contain an antigen. It can, however, be co-administered with an antigen plasmid such as pGag, as shown in FIG. 4.
Figure 6:
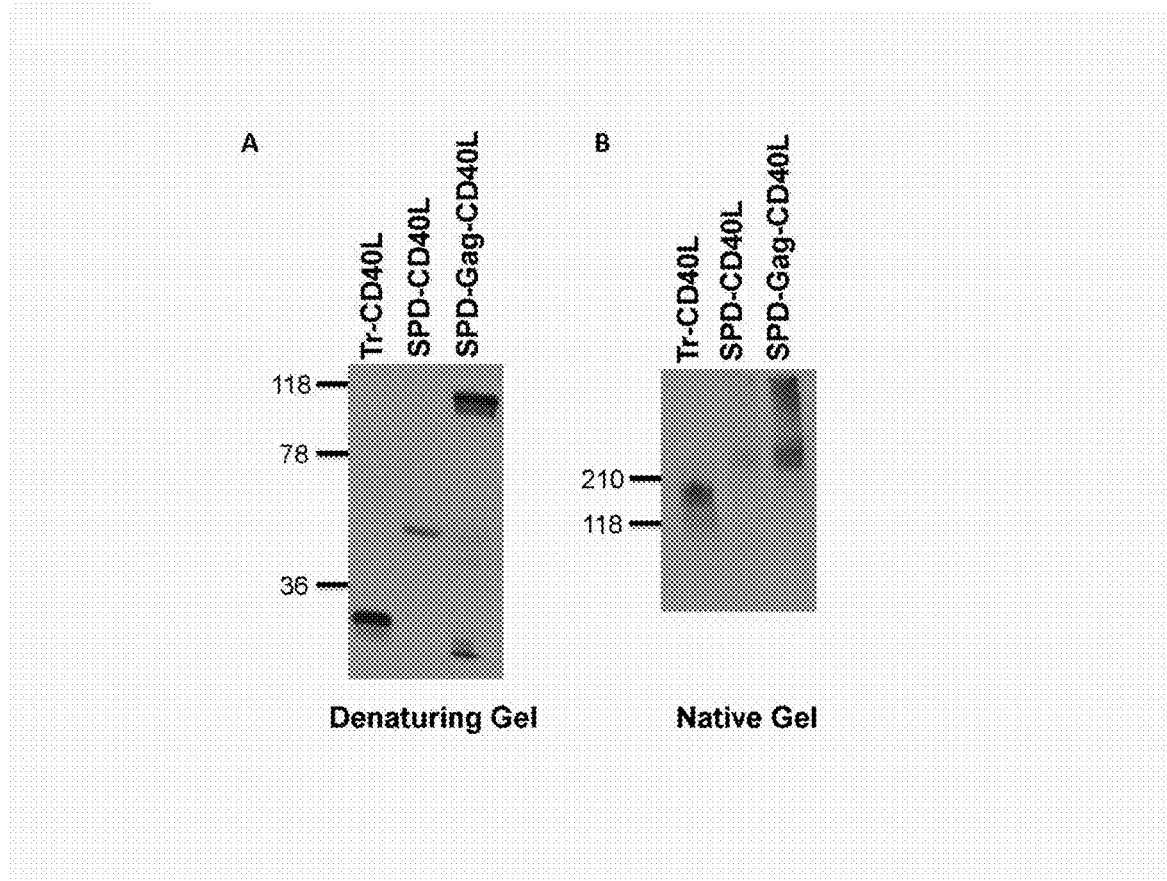
FIG. 6: pSPD-Gag-CD40L encodes a secreted protein. Panel A shows a Western blot of a reducing SDS-PAGE gel analysis of the culture media of 293T cells were transiently transfected with DNA for the plasmids shown. An antibody for murine CD40L was used to reveal the protein bands. As shown, pSPD-Gag-CD40L encodes a single protein of the expected size of 105 kDa. A single 105 kDa band was also observed using antibody to the p24 portion of Gag (not shown). Panel B shows a similar analysis using non-denaturing PAGE in the absence of a reducing agent. Multiple bands were observed at >200 kDa molecular weight, demonstrating the formation of large multimeric complexes. As is commonly observed in such analyses of collagen-like proteins, partial denaturation during processing can result in an unwinding of some of the collagen triple helix, which could thus lead to a less compact protein that moves more slowly through the gel during the electrophoretic process.

As described in the instant application, a surprisingly active vaccine can be made by incorporating an antigen with the arms of SPD in the 4-trimer SPD-CD40L construct that was previously developed by the inventors and shown in FIGS. 3 and 4. For demonstration purposes, the HIV-1 Gag antigen was inserted into the coding region for the SPD collagen-like arm as shown in SEQ ID NO:1 and SEQ ID NO:2 and depicted in FIG. 5. This fusion protein uses the natural SPD "arm" which has been shown to be 46 nm long in shadow electronmicroscopic studies. The collagen-like triple helical structure and results from the class Gly-Xaa-Yaa collagen-like repeats in the protein which number 59 repeats in the arm. For the instant invention, the length of this arm can be varied in two ways: (1) Amino acid deletions can be introduced that truncate one Gly-Xaa-Yaa motif; and (2) the antigen can be inserted variably along the length of the arm. Considering the 177 amino acids in the 59 collagen-like repeats, the antigen domain can be positioned from 10 to 177 amino acids more C-terminal from the hub, or preferably from 20 to 140 amino acids more C-terminal from the hub, or more preferably from 40 to 120 amino acids more C-terminal from the hub. Likewise, the antigen domain can placed closer or further from the TNFSF extracellular domain (ECD). For example, the antigen domain could be from 0 to 167 amino acids more N-terminal from the TNFSF ECD, or more preferably from 40 to 120 amino acids more N-terminal from the ECD. As non-limiting examples, SEQ ID 13 and SEQ ID 14 show a fusion protein where the antigen domain was shifted by 10 amino acid positions within the arm of SPD. Likewise, SEQ ID NO 17 and SEQ ID NO 18 show a fusion protein in which 20 amino acids have been removed from the SPD arm. With this as a guide, the skilled artisan will know that it is not critical exactly where in the SPD arm the antigen domain should be positioned.

As previously described by the inventors, 2-trimer forms of TNFSF ligands can be made using Acrp30. FIGS. 3 and 4 show the design and vaccine adjuvant efficacy of an Acrp30-CD40L fusion protein. This molecule has two collagen-like arms. Accordingly, it is contemplated to place an antigen domain within the arms of Acrp30 as shown in SEQ ID 3 and SEQ ID 4 which place the HIV-1 Env antigen within the arms of an Acrp30-BAFF fusion protein. Analogous fusion proteins could be made from other collectin fusion proteins besides SPD-TNFSFs and from other C1q family molecules besides Acrp3-TNFSFs.

A feature of these fusion proteins is that they can readily be made using the natural collectin or C1q family sequences and TNFSF sequences from a variety of organisms. It is preferable to use the murine coding sequences for studies in mice, the macaque coding sequences for studies in macaques, the human coding sequences for use in humans, etc. As non-limiting examples, the sequences shown provide fusion protein made using either murine or human sequences. Thus, animal vaccine uses are specifically contemplated as one use of the instant invention.

In these cases, antigen was introduced into many-trimer forms of TNFSFs by standard genetic engineering methods familiar to the skilled artisan. Such fusion proteins can be made by ligating together segments of genes or, more preferably, by ordering a custom synthesis from a commercial supplier (e.g. DNA2.0, Genset, Genewiz, and other suppliers). In other cases, it is possible to prepare antigenic peptides and TNFSF trimers separately and then link them together by chemical methods. The linking reagents and synthesis strategies that can be used are described in U.S. Pat. No. 6,482,411 B1, which is incorporated by reference.

There is a wide choice of antigens from infectious disease antigens, depending on the species in need of vaccination. Without limitation, these can be selected from the following list of disease-causing pathogens:

Viruses such as influenza A and B, parainfluenza, poxviruses, ebola virus, hepadnavirus, filoform viruses such as marburg virus, dengue fever virus, influenza A and B, respiratory syncytial virus, measles (rubeola virus), human immunodeficiency virus (HIV), human papillomavirus (HPV), varicella-zoster, herpes simplex I and 2, cytomegalovirus, Epstein-Barr virus, JC virus, rhabdovirus, rotavirus, rhinovirus, adenovirus, orthomyxovirus, papillomavirus, parvovirus, picornavirus, poliovirus, mumps, rabies, reovirus, rubella, togavirus, retrovirus, coxsackieviruses, equine encephalitis, Japanese encephalitis, yellow fever, Rift Valley fever virus, hepatitis A, B, C, D, and E virus, hantavirus, coronavirus (including SARS and MERS), and the like;

Microbial agents such as *Borrelia* species, *Bacillus anthracis, Borrelia burgdorferi, Bordetella pertussis, Camphylobacter jejuni, Chlamydia* species, *Chlamydial psittaci, Chlamydial trachomatis, Clostridium* species, *Clostridium tetani, Clostridium botulinum, Clostridium perfringens, Corynebacterium diphtheriae, Coxiella* species, an *Enterococcus* species, *Erlichia* species *Escherichia coli, Francisella tularensis, Haemophilus* species, *Haemophilus injiuenzae, Haemophilus parainjiuenzae, Lactobacillus* species, a *Legionella* species, *Legionella pneumophila, Leptospirosis interrogans, Listeria* species, *Listeria monocytogenes, Mycobacterium* species, *Mycobacterium tuberculosis, Mycobacterium leprae, Mycoplasma* species, *Mycoplasma pneumoniae, Neisseria* species, *Neisseria meningitidis, Neisseria gonorrhoeae, Pneumococcus* species, *Pseudomonas* species, *Pseudomonas aeruginosa, Salmonella* species, *Salmonella typhi, Salmonella enterica, Rickettsia* species, *Rickettsia ricketsii, Rickettsia typhi, Shigella* species, *Staphylococcus* species, *Staphylococcus aureus, Streptococcus* species, *Streptococccus pnuemoniae, Streptococcus pyrogenes, Streptococcus mutans, Treponema* species, *Treponema pallidum*, a *Vibrio* species, *Vibrio cholerae, Yersinia pestis*, and the like.

Fungal, protozoan, and parasitic agents such as *Aspergillus* species, *Candida* species, *Candida albicans, Candida tropicalis, Cryptococcus* species, *Cryptococcus neoformans, Entamoeba histolytica, Histoplasma capsulatum, Coccidioides immitis, Leishmania* species, *Nocardia asteroides, Plasmodium falciparum, Plasmodium vivax, Toxoplasma gondii, Trichomonas vaginalis, Toxoplasma* species, *Trypanosoma brucei, Schistosoma mansoni, Pneumocystis jiroveci*, and the like.

There is a wide choice of tumor antigens, depending on the species in need of cancer immunotherapy. Without limitation, these can be selected from the following list of cancer-associated antigens:

gp100; WT1; Melan-A; tyrosinase; PSMA; HER-2/neu; MUC-1; PRAME; topoisomerase; BRAF V600E; bcr-Abl; sialyl-Tn; carcinoembryonic antigen; ErbB-3-binding protein-I; alpha-fetoprotein; and the cancer testis antigens MAGE-AI, MAGEA4, and NY-ESO-1; MART-1, Dipeptidyl peptidase IV (DPPIV), adenosine deaminase binding protein (ADAbp), cyclophilin b, Colorectal associated antigen (CRC)-COI7-1 AlGA 733, Carcinoembryonic Antigen (CEA) and its immunogenic epitopes CAP-1 and CAP-2, etv6, amll, Prostate Specific Antigen (PSA) and its immunogenic epitopes PSA-1, PSA-2, and PSA-3, prostate specific membrane antigen (PSMA), MAGE-family of tumor antigens (e.g., MAGEAI, MAGE-A2, MAGE-A3, MAGE-A4, MAGE-A5, MAGE-A6, MAGE-A7, MAGE-AS, MAGE-A9, MAGE, MAGE-Xp2 (MAGE-B2), MAGE-Xp3 (MAGE-B3), MAGE-Xp4 (MAGE-B4), MAGE-C1, MAGE-C2, MAGE-C3, MAGE-C4, MAGEC5), GAGE-family of tumor antigens (e.g., GAGE-I, GAGEIn 2, GAGE-3, GAGE-4, GAGE-5, GAGE-6, GAGE-7, GAGES, GAGE-9), BAGE, RAGE, LAGE-1, NAG, GnT, MUM-1, CDK4, tyrosinase, p53, MUC family, HER2/neu, p21ras, RCASl, a-fetoprotein, E-cadherin, alpha-catenin, beta-catenin and gamma-catenin, p 120ctn, brain glycogen phosphorylase, SSX-1, SSX-2 (HOM-MEL), EGFRviii, SSX-1, SSX-4, SSX-5, SCP-1, CT-7, cdc27, adenomatous polyposis coli protein (APC), fodrin, PI A, Counexin 37, Ig-idiotype, p15, gp75, GM2 and GD2 gangliosides, viral products such as human papilloma virus proteins, Smad family of tumor antigens, LMP-1, LMP-2, EBV-encoded nuclear antigen (EBNA)-1, or c-erbB-2, and the like.

Figure 12:
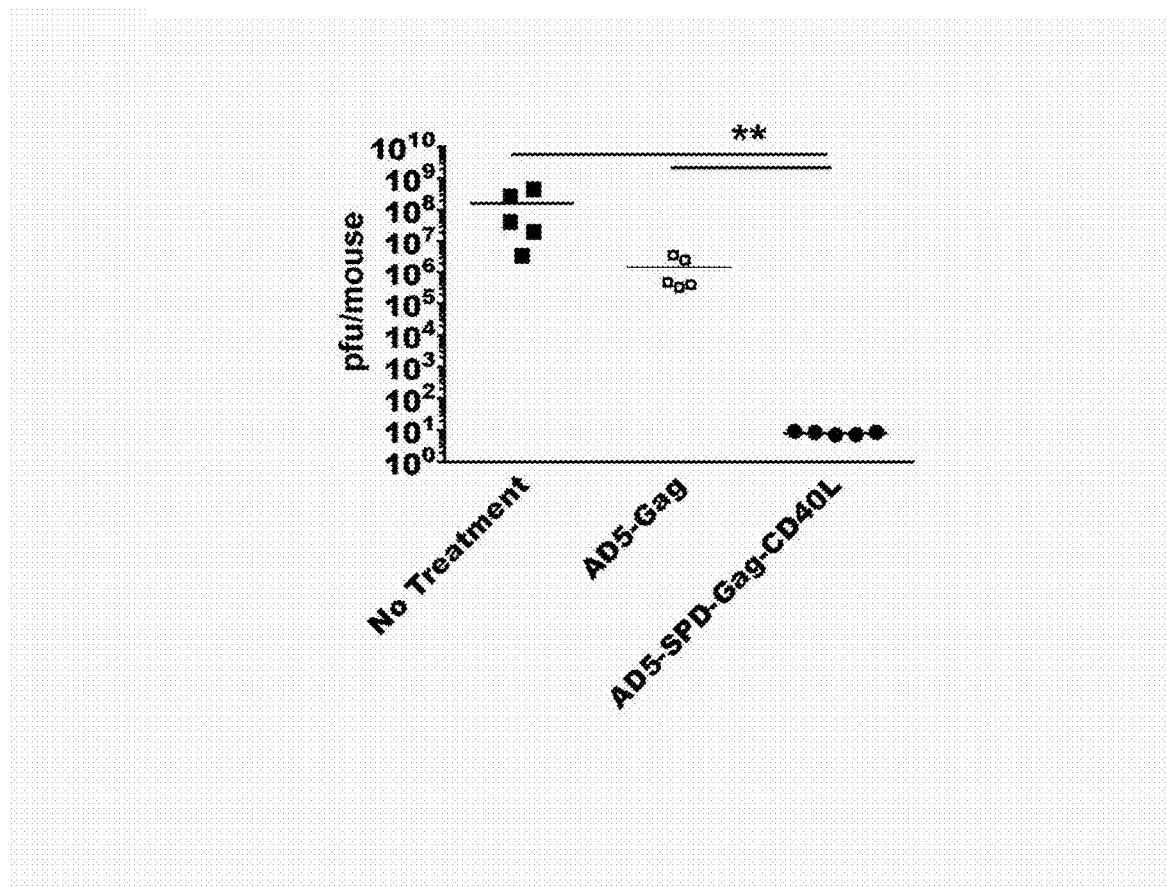
FIG. 12: Adenoviral vector delivery of SPD-Gag-CD40L is surprisingly protective against virus challenge. BALB/c female mice were immunized intramuscularly on days 0 and 14 with adenovirus 5 (Ad5) expressing the HIV-1 Gag antigen (Ad5-Gag) or the SPD-Gag-CD40L construct (Ad5-SPD-Gag-CD40L). Two weeks following the final vaccination, mice were challenged intraperitoneally with vaccinia-Gag virus (10E7 PFU). Mice were sacrificed 5 days later and ovaries were harvested for vaccinia PFU determinations. Surprisingly, Ad5-SPD-Gag-CD40L vaccination reduced viral load by ~7 logs following vaccinia-Gag challenge. No detectable virus could be found in the mice that had received this vaccine, indicating complete protection (sterilizing immunity).
Figure 13:
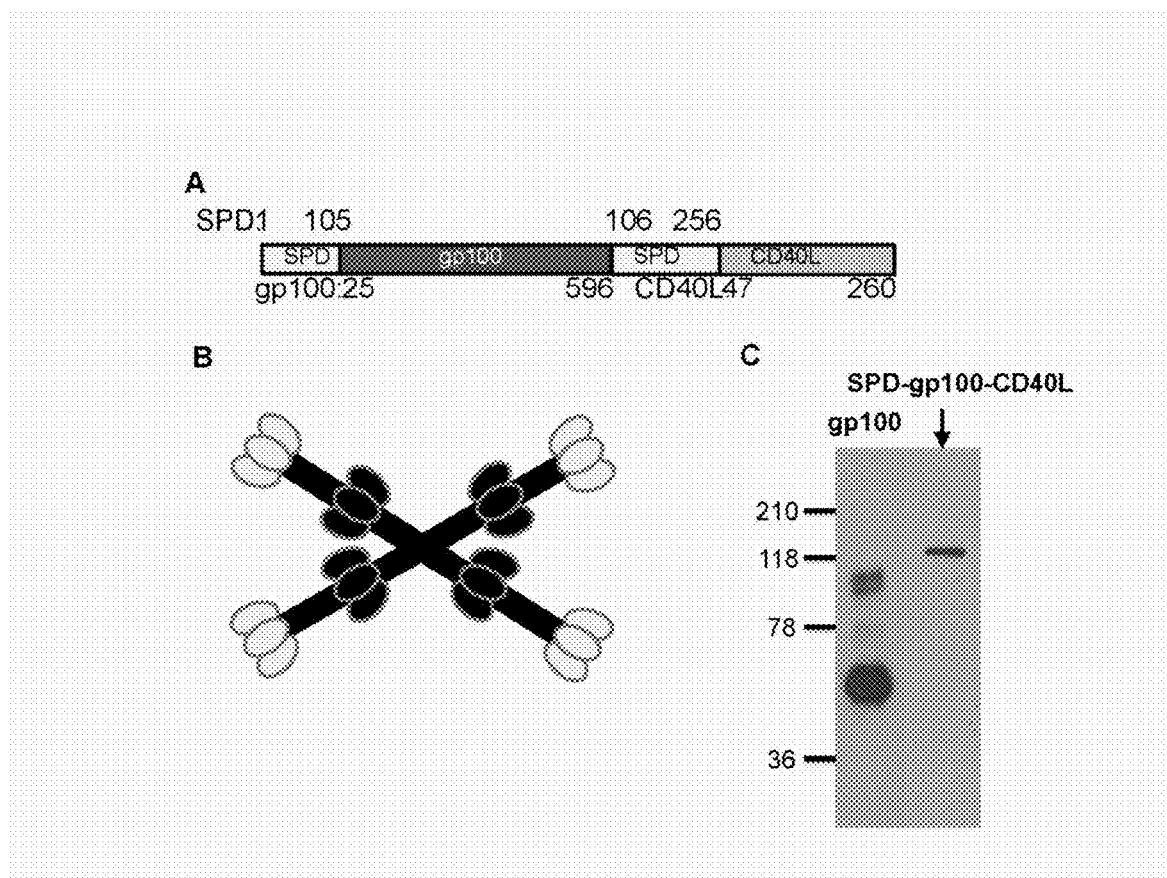
FIG. 13: Construction and Western blot of SPD-gp100-CD40L. Panel A: Model of SPD-gp100-CD40L fusion Amino acids 25 to 596 (sequence KVPRNQD to EAGL-GQV) of human gp100 was inserted between amino acids 105 and 106 of murine SPD within the SPD-CD40L fusion construct. Panel B: Schematic diagram of expected SPD-gp100-CD40L 4-trimer structure. Panel C: Western blot analysis. 293T cells were transfected with DNA plasmid encoding gp100 or the SPD-gp100-CD40L fusion protein. After 48-hour culture, supernatant was collected and run on an SDS-PAGE gel in the presence of reducing agent. Western blot was performed using a polyclonal antibody to gp100.

There is a wide choice of delivery methods for the vaccines of the instant invention. Where the vaccine is comprised of a nucleic acid sequence, it can be delivered using a DNA or RNA vectors. Without limitation, these can be selected from the following list: Adenovirus (as shown in FIG. 12 for example), poxvirus including Modified Vaccinia Ankara, Herpesviruses, retroviruses, lentiviruses, Newcastle Disease Virus, Mumps Virus, Measles Virus, Vesicular Stomatitis Virus, rhabdovirus, Para-influenza Virus, Sendai virus, Influenza Virus, Reovirus, and a Seneca Valley virus, alphavirus, Sindbis virus, Venezuealan Equine Envephalitis (VEE), Coxsackie virus, myxoma virus, viral organisms include those that are dsDNA viruses, ssDNA viruses, dsRNA viruses, (+) ssRNA viruses (−) sRNA viruses, ssRNA-RT viruses, and dsDNA-RT viruses, and the like.

Vaccines of the present invention can also be delivered as plasmid DNAs that include a promoter (e.g., CMV promoter) and a transcription termination and polyadenylation sequence. Such plasmids also include genes needed for growth in bacteria, but fragments of DNA can also be prepared by in vitro enzymatic synthesis. An exemplary plasmid used in the experiments in FIGS. 4 and 6-17 is pcDNA3.1 (Life Technologies, Inc., Carlsbad, Calif.) but other choices are available. The DNA can be delivered directly by injection into muscle ("naked" DNA vaccination) as shown in FIGS. 8-11 and 15-17. It can also be delivered by a number of means including electroporation, microinjection, gene gun delivery, lipofection, polymer-mediated delivery, and the like. The same methods can be used for RNA vaccination. In addition, for bacteria that enter cells such as *Salmonella* or *Listeria*, plasmid DNA can be introduced into these bacteria which then carry that DNA into the eukaryotic host cell, a process called "bactofection."

Figure 7:
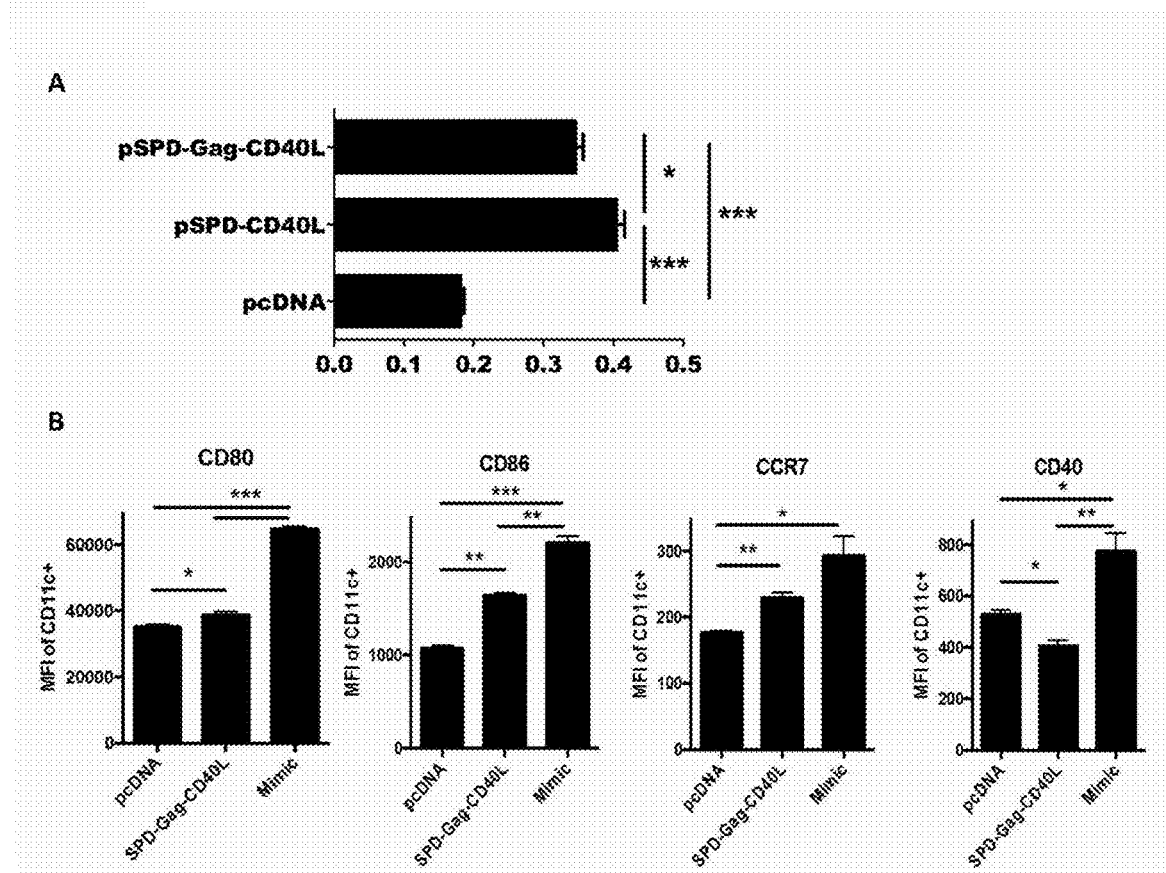
FIG. 7: Qualifying assay for the biological activity of SPD-Gag-CD40L in vitro. Panel A: In vitro activity using a CD40 receptor NF-κB indicator cell line. To produce soluble protein, 293T cells were transiently transfected with plasmids for pcDNA3.1 (empty vector control), pSPD-CD40L, or pSPD-Gag-CD40L and the protein-containing supernatants were collected 48 hours later. To determine the activity of the CD40L in these proteins, the culture media as added to cultures of 293 reporter cells containing an NF-κB-driven gene for secreted alkaline phosphatase (SEAP) and expressing the CD40 receptor (CD40-293-SEAP reporter cells). If the CD40 receptor is activated by CD40L, then NF-κB-driven SEAP production results in the secretion of SEAP which can be measured by a colorimetric enzyme assay at OD650 (Maurais et al., Virology. 2009; 385(1):227-32). In this assay, a single trimer of CD40L (R&D Systems, Inc., Minneapolis, Minn.) was entirely inactive and did not induce SEAP production (not shown), indicating the strict requirement for a many-trimer form of CD40L for activity in this assay. In contrast, both the pSPD-CD40L adjuvant protein and the new SPD-Gag-CD40L protein of the instant invention were active as CD40 receptor activators. Panel B: Stimulating activity on mouse bone marrow-derived dendritic cells (BMDDC). As in Panel A, culture supernatants from 293T cells transfected with pcDNA3.1 or pSPD-Gag-CD40L were incubated with BMDDC for 18 hours. Cells were washed, stained with fluorochrome-conjugated antibodies, and assayed by flow cytometry for the expression of activation and maturation markers. The SPD-Gag-CD40L protein upregulated CD80 and especially CD86 and CCR7, indicating that this fusion protein was fully capable of activating normal dendritic cells. As expected, the CD40 receptor was downregulated by exposure to SPD-Gag-CD40L. A cytokine mix was used as a positive control ("Mimic," consisting of 10 ng/ml of rhTNF-alpha, 10 ng/ml of rhIL-1beta, 1000 U/ml of rhIL-6 and 1 μg/ml of PGE2; Sato et al., Cancer Sci. 2003; 94(12):1091-8). * $p<0.05$,  $p<0.01$, and * $p<0.001$ compared to pcDNA3.1 supernatant. Data represents independent wells in the same experiment.
Figure 8:
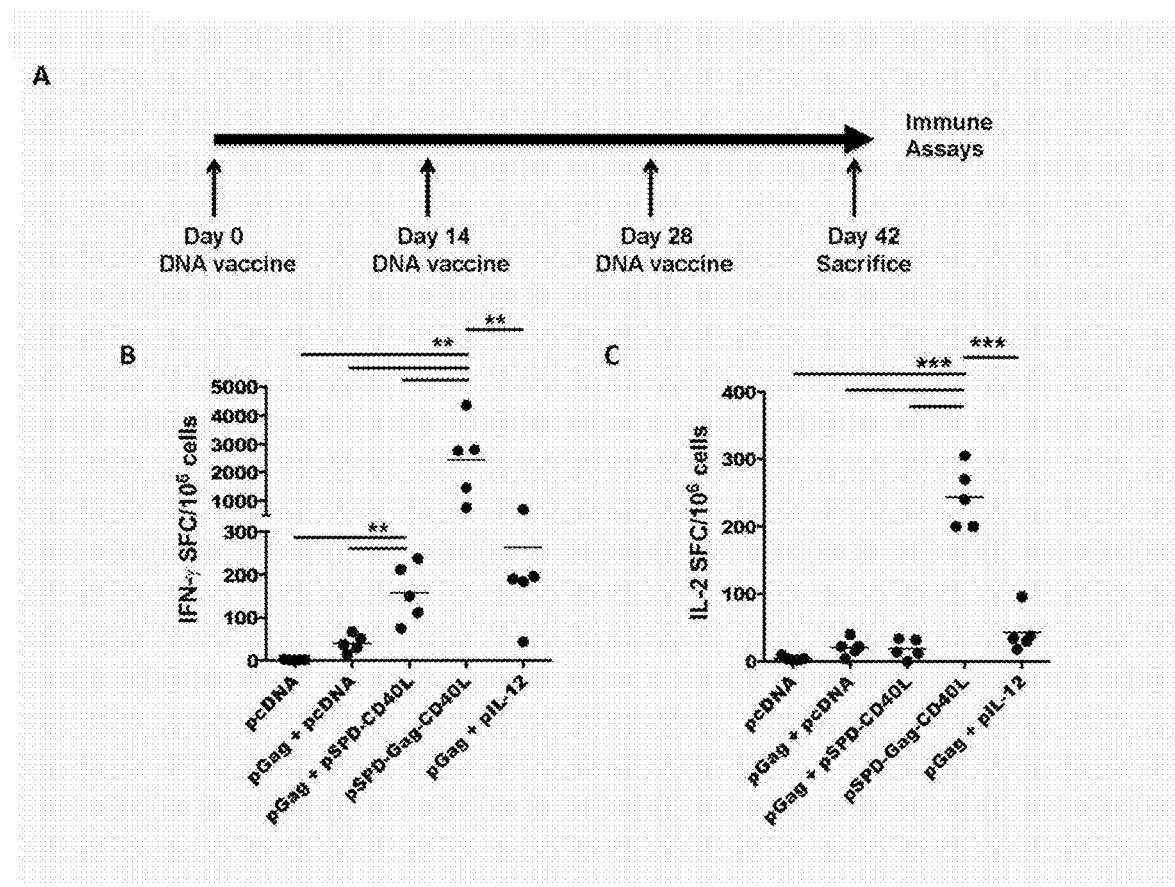
FIG. 8: DNA vaccination with pSPD-Gag-CD40L demonstrates a surprisingly high level of CD8+ T cell responses. Panel A: DNA vaccination schedule. Mice were vaccinated three times at two-week intervals with an intramuscular injection of 100 μg of plasmid DNAs. Panels B and C: CD8+ ELISPOT assay. To measure the Gag-specific CD8+ T cell response, spleen cells were collected 14 days after the last vaccination and tested by ELISPOT assays. Panel B shows cells producing interferon-gamma and Panel C shows cells producing IL-2. The control vaccination is pGag+pcDNA where empty pcDNA3.1 (pcDNA) was used to keep the total amount of DNA constant. The previously reported mix of antigen and 4-trimer CD40L adjuvant plasmid is pGag+pSPD-CD40L which consists of separate plasmids for antigen and adjuvant, i.e., not present in the same secreted molecule. Surprisingly, pSPD-Gag-CD40L, the subject of the instant invention, resulted in a massive antigen-specific CD8+ T cell response (note that a broken Y-axis is needed to keep the results visible in the graph). In contrast, pGag+pIL-12 gave more modest CD8+ T cell responses, even though a pIL-12 plasmid is currently being evaluated in human vaccine trials. Panel C shows the same analysis using IL-2 ELISPOT assay and showed the surprising strength of pSPD-Gag-CD40L, the subject of the instant invention.
Figure 9:
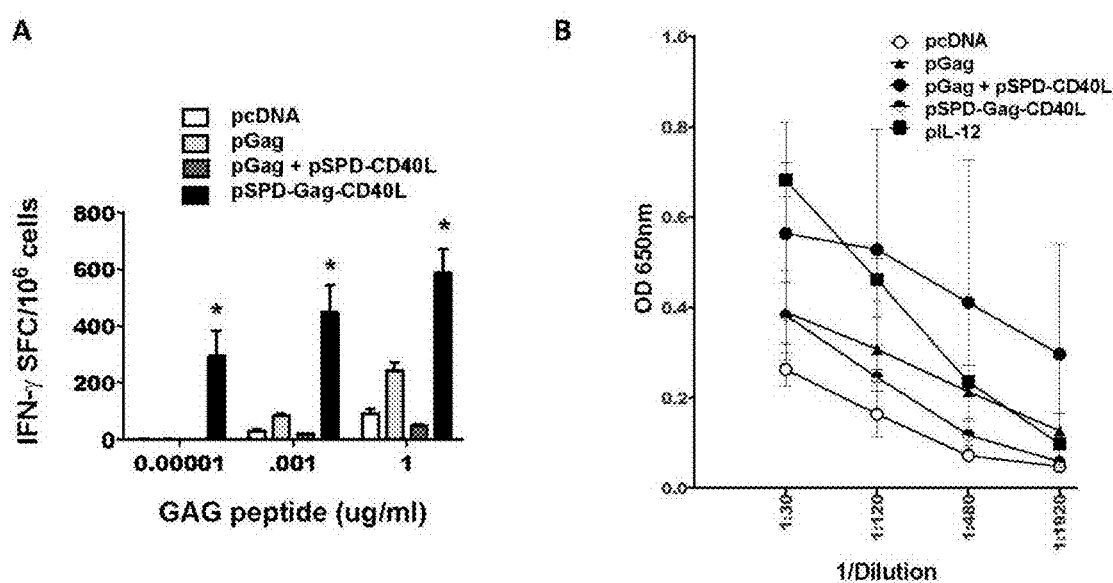
FIG. 9: DNA vaccination with pSPD-Gag-CD40L demonstrates a surprising improvement in CD8+ T cell quality. Panel A: T cell receptor avidity for peptide antigen/MHC-I measured by ELISPOT assay. Splenocytes were cultured with serial dilutions of CD8+ T cell specific peptide AMQMLKFTI for 18 hours. Splenocytes from mice vaccinated with pSPD-Gag-CD40L induced a significant increase in IFN-γ ELISPOTs following stimulation with Gag peptide AMQMLKFTI at a concentration of 1 ng/ml and 10 pg/ml whereas there was essentially no activity at these doses using splenocytes from mice vaccinated with pGag antigen alone or a mixture of separate plasmids for pGag and pSPD-CD40L adjuvant. * $p<0.05$;  $p<0.01$; * $p<0.001$ compared to pGag alone or pGag SPD-CD40L vaccination. Panel B: IgG antibody responses against Gag antigen. Total IgG specific for Gag was measured by ELISA assay from mouse serum collected on day 42. Consistent with a previous study (Stone et al., J Virol. 2006; 80(4):1762-72), CD40L adjuvant used in this format is not an adjuvant for antibody responses.
Figure 10:
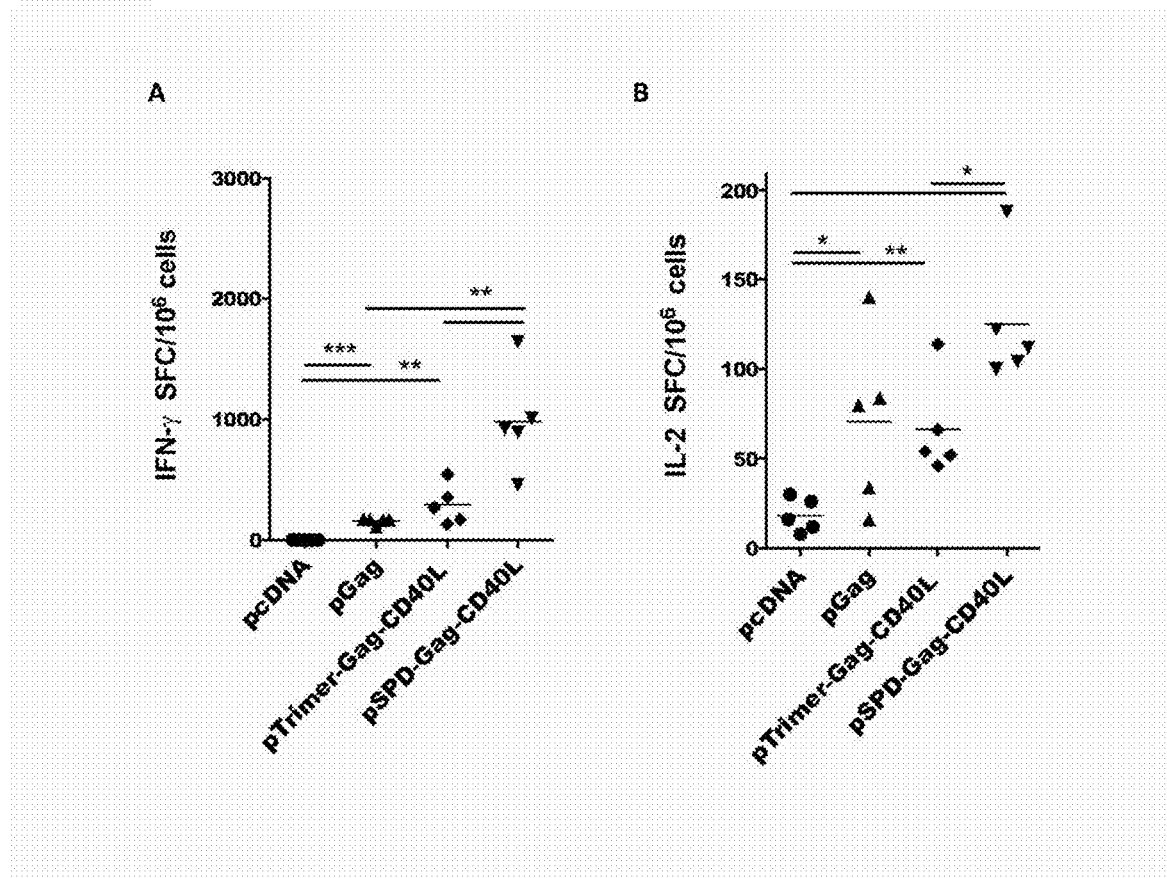
FIG. 10: The multi-trimer structure of SPD-Gag-CD40L is necessary for the improved vaccine effect. In Panels A and B, pTrimer-Gag-CD40L was used as 1-trimer control for 4-trimer pSPD-Gag-CD40L. As shown, the many-trimer structure was necessary for the strong adjuvant effect.
Figure 11:
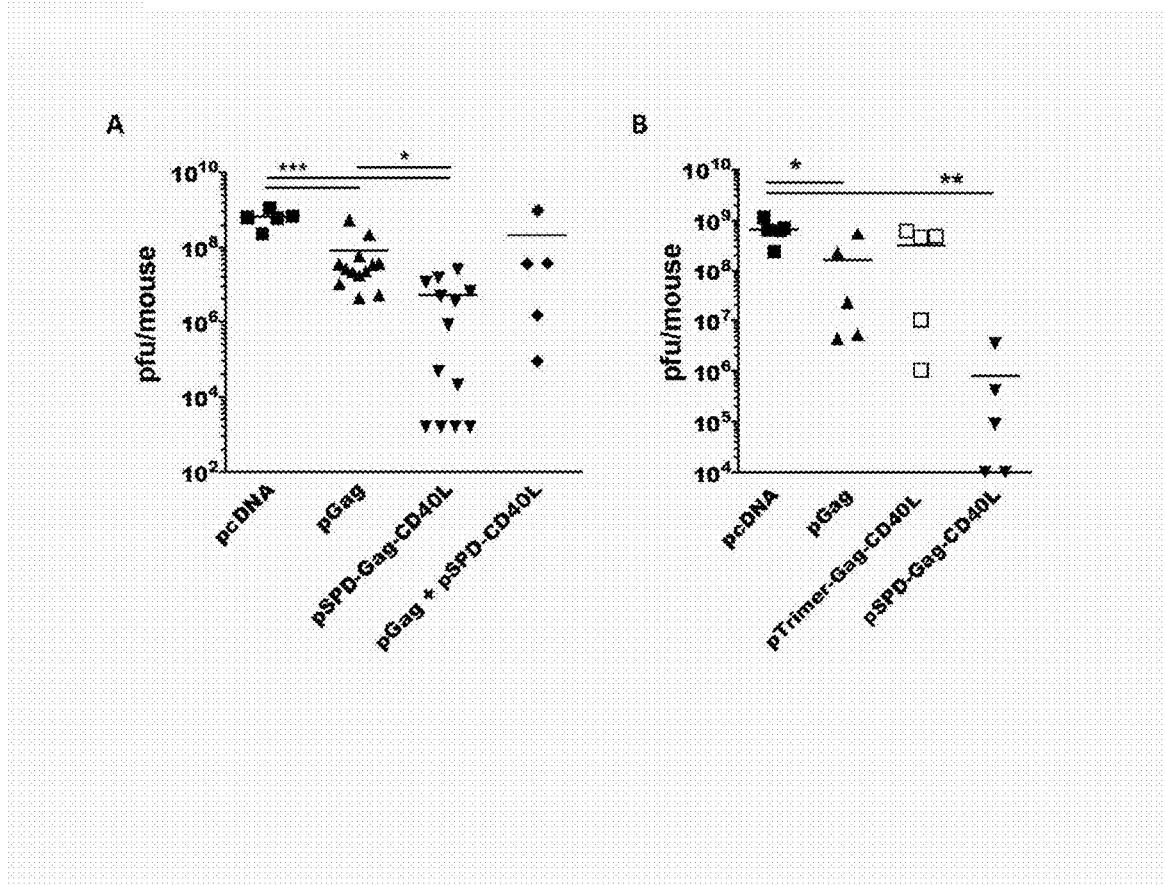
FIG. 11: Protective effects of pSPD-Gag-CD40L vaccination measured by vaccinia-Gag viral challenge. BALB/c female mice were immunized intramuscularly with the plasmids shown on days 0, 14, and 28. Two weeks following the final vaccination, the mice were challenged intraperitoneally with 10E7 plaque-forming units (PFU) of vaccinia-Gag. Mice were sacrificed 5 days after viral challenge and the ovaries were harvested and analyzed for PFU. Panel A: Intramuscular DNA vaccination with pSPD-Gag-CD40L resulted in significantly greater protection from viral challenge. In contrast, DNA vaccination with a mixture of pGag antigen plus pSPD-CD40L adjuvant as separate plasmids only induced a modest reduction in viral loads that was not significantly reduced compared to pGag antigen alone. * $p<0.05$;  $p<0.01$; * $p<0.001$. Panel B: Evaluation of a single trimer pTrimer-Gag-CD40L construct. As shown before, the multi-trimer structure of SPD-Gag-CD40L is necessary for the improved vaccine effect.
Figure 14:
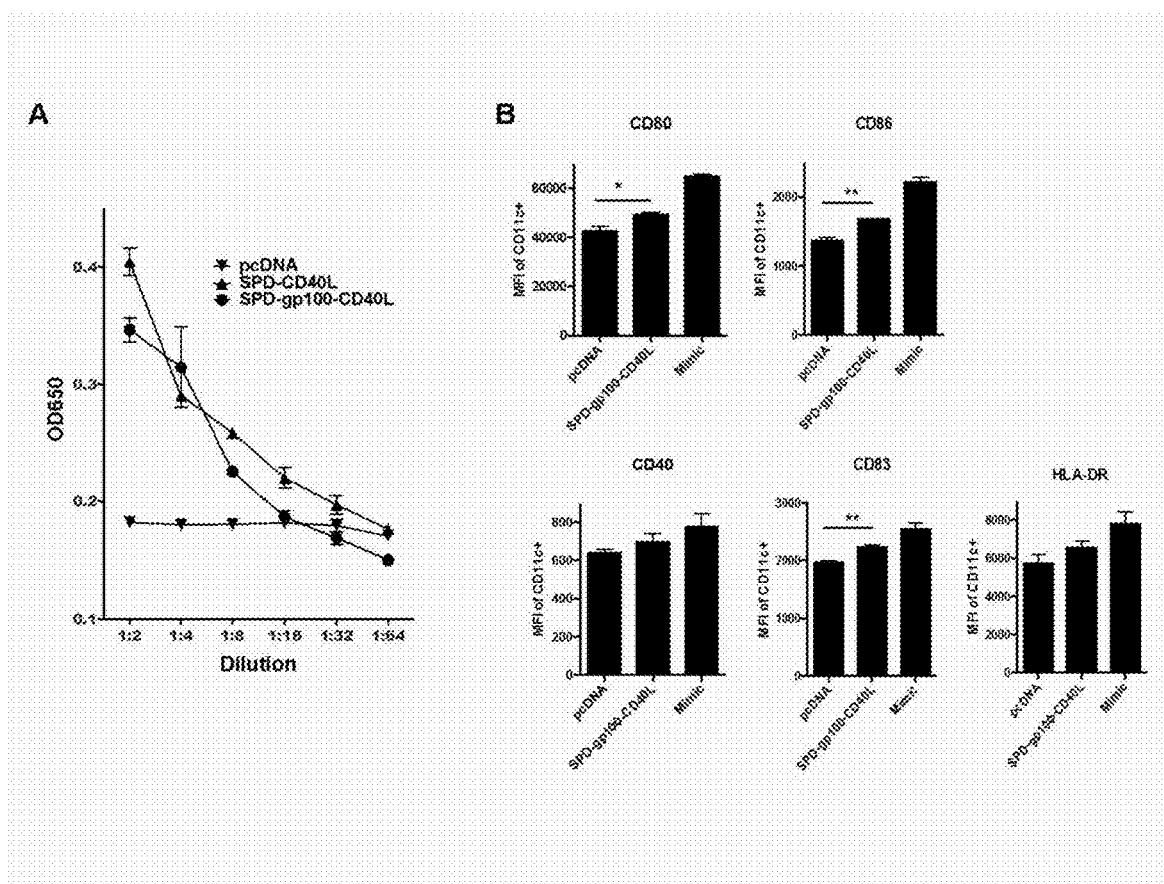
FIG. 14: Biological activity of SPD-gp100-CD40L. Panel A: In vitro activity of SPD-CD40L and SPD-gp100-CD40L was determined using a cell-based CD40 NF-kB enzymatic reporter system. An equivalent amount of 293T supernatant from pcDNA3.1, pSPD-CD40L or pSPD-gp100-CD40L transfected cells was incubated with 293-CD40-SEAP NF-kB reporter cells. Panel B: In vitro activity of SPD-gp100-CD40L was evaluated on mouse bone marrow derived mouse DC and compared to empty vector or Mimic cytokine positive control. * $p<0.05$, ** $p<0.01$ by Student's t test compared to pcDNA3.1 supernatant.

As another use of the instant invention, fusion proteins comprised of an antigen linked to a many-trimer TNFSF can be administered to APCs like dendritic cells ex vivo, as shown in FIGS. 7 and 14. Once the antigen has been delivered and the APCs activated, these DCs can then be delivered to a host as a cellular form of vaccination (Barth et al., 2010; 16(22):5548-56. PMCID: 2994719).

Without limitation, the following examples of invention are disclosed:

Example 1: Vaccination to Elicit CD8+ T Cells Against HIV-1 Gag Antigen

CD40 ligand (CD40L, CD154) is a membrane protein that is important for the activation of dendritic cells (DCs) and DC-induced CD8+ T cell responses. To be active, CD40L must cluster CD40 receptors on responding cells. To produce a soluble form of CD40L that clusters CD40 receptors necessitates the use of a multi-trimer construct. With this in mind, a tripartite fusion protein was made from surfactant protein D (SPD), HIV-1 Gag as a test antigen, and CD40L, where SPD serves as a scaffold for the multi-trimer protein complex. This SPD-Gag-CD40L protein activated CD40-bearing cells and bone marrow-derived DCs in vitro. Compared to a plasmid for Gag antigen alone (pGag), DNA vaccination of mice with pSPD-Gag-CD40L induced an increased number of Gag-specific CD8+ T cells with increased avidity for MHC-I-restricted Gag peptide and improved vaccine-induced protection from challenge by vaccinia-Gag virus. The importance of the multi-trimeric nature of the complex was shown using a plasmid lacking the N-terminus of SPD that produced a single trimer fusion protein. This plasmid, pTrimer-Gag-CD40L, was only weakly active on CD40-bearing cells and did not elicit strong CD8+ T cell responses or improve protection from vaccinia-Gag challenge. An adenovirus-5 (Ad5) vaccine incorporating SPD-Gag-CD40L was much stronger than Ad5 expressing Gag alone (Ad5-Gag) and induced complete protection (i.e., sterilizing immunity) from vaccinia-Gag challenge. Overall, these results show the potential of a new vaccine design in which antigen is introduced into a construct that expresses a multi-trimer soluble form of CD40L, leading to strongly protective CD8+ T cell responses.

DNA vaccination induces both cellular and humoral responses against an encoded antigen, protecting animals against subsequent infection with a microbial pathogen. DNA vaccines are potent inducers of virus-specific T cell responses and studies have shown that prophylactic DNA vaccines, administered either alone or with recombinant viral vaccines as prime/boost vaccine, can provide protection against challenge with viral pathogens including SIV. The HIV-1 Gag antigen encoded within DNA or viral vector vaccines is known to induce measurable immune responses, providing a method to vaccinate against HIV-1. One strategy to enhance the effectiveness of DNA vaccines encoding weakly immunogenic antigens is by co-delivering genes encoding molecular adjuvants. TNF superfamily ligands (TNFSFL) including CD40L are costimulatory molecules involved in dendritic cell (DC) and T cell activation and have previously been tested as adjuvants to enhance immune responses in several vaccination studies.

CD40L acts on DCs to induce or "license" CD8+ T cell responses. CD40L also works on DCs to diminish the immune suppression due to CD4+CD25+FoxP3+ regulatory T cells (Tregs) and prevents the premature disappearance vaccine-generated CD8+ T cells. Consequently, we and others have examined the potential of CD40 stimulation as an adjuvant for vaccines designed to generate CD8+ T cell responses.

CD40-mediated activation requires clustering of this receptor leading to the assembly of a supramolecular signaling complex inside cells. When CD40L is expressed on CD4+ T cells, the array of membrane CD40L molecules ligates receptors on DCs and other cells to create a patch of clustered CD40 receptors that activates downstream events. For soluble ligands of CD40, some other way must be found to induce CD40 receptor clustering. Most reports on CD40 activation use agonistic anti-CD40 antibodies. It is now recognized that these antibodies only induce a CD40 signal if they are mounted onto Fc receptors (FcRs), thereby creating an array of anti-CD40 antibodies that can cluster the receptors on an adjacent CD40 receptor-bearing cell. This requirement restricts the effectiveness of anti-CD40 antibodies to tissue microenvironments that contain FcR-bearing cells. Other drawbacks of using anti-CD40 antibodies are their propensity to generate host antibodies against themselves, their toxicity for mice and humans, and their depleting effect on CD40-bearing B cells in the blood. These negative qualities argue against the routine use of agonistic anti-CD40 antibody as an adjuvant for vaccines given to otherwise healthy people in order to prevent infection by pathogens such as HIV-1.

The use of CD40L presents an alternative to agonistic anti-CD40 antibodies as a vaccine adjuvant. CD40L is made as a Type II membrane protein but can be proteolytically cleaved from the cell surface and released as a soluble single trimer. By itself, a single trimer of CD40L is unable to provide clustering of CD40 receptors sufficient to generate a cell signal. Consequently, we devised fusion proteins in which the extracellular domain of CD40L is joined to a scaffold protein such as surfactant protein D (SPD). The resulting fusion protein, SPD-CD40L, is expected to form a plus sign-shaped 4-trimer molecule held together at its N-terminal "hub" by interchain cysteine bonds. Each "arm" of the SPD portion is a collagen-like triple helix that presents the CD40L trimers on the outside of the molecule for easy interaction with CD40 receptors. As expected, we previously found that SPD-CD40L activated DCs in vitro and was a strong vaccine adjuvant for CD8+ T cell responses against HIV-1 antigens.

In the previous study, mice were vaccinated with plasmid DNAs for HIV antigens such as Gag (pGag) mixed in a single syringe with pSPD-CD40L. In the present study, we considered the effects of introducing the HIV-1 Gag antigen into the SPD-CD40L protein to create SPD-Gag-CD40L, a single chain peptide that retains the ability to form a multi-trimer structure capable of clustering and thereby activating the CD40 receptor. This molecular design resulted in a DNA vaccine that elicited much stronger Gag-specific CD8+ T cell responses capable of protecting mice from challenge by vaccinia virus engineered to express Gag (vaccinia-Gag). Since DNA vaccination is relatively inefficient, viral delivery was also examined by introducing SPD-Gag-CD40L into an adenovirus-5 (Ad5) vaccine vector. The resulting Ad5-SPD-Gag-CD40L vaccine provided essentially total protection from vaccinia-Gag challenge, further attesting to the remarkable effectiveness of including the antigen inside the SPD-CD40L construct rather than administering SPD-CD40L as a separate adjuvant molecule.

Materials and Methods

Construction and Preparation of DNA Plasmids

To construct a HIV-1 Gag DNA vaccine (pGag), the gag coding sequence was fused with the first 21 amino acids of human tissue plasminogen activator (t-PA) as a signal peptide as described previously (Stone et al., J Virol. 2006; 80(4):1762-72). A DNA construct encoding murine SPD-CD40L was also previously described (Stone et al., J Virol. 2006; 80(4):1762-72). To construct SPD-Gag-CD40L, the p55 gag sequence from pGag was inserted into the "arm" portion of murine SPD between amino acids 105 and 106 within the construct SPD-CD40L (i.e. between peptide sequence GERGLSG and PPGLPGI of murine SPD) (see FIG. 5). To construct pTrimer-Gag-CD40L, the ScGag coding sequence was fused with amino acid 106 of mouse SPD within construct SPD-CD40L (i.e. fusing ScGag to a fragment of SPD-CD40L starting at peptide sequence PPGLPGI), thereby deleting the N-terminal portion of SPD that contains the dicystine-containing "hub" region needed for self-assembly into a 4-armed molecule. As a result, this construct is expected to form single trimers of Gag-SPD-CD40L (see FIG. 5). Plasmid pIL-12p70, encoding mouse single chain IL-12, was purchased from Invivogen Inc. All plasmids were propagated in *Escherichia coli* strain TOP10. Endotoxin-free DNA plasmid preparations were prepared using an Endofree Giga plasmid kit (Qiagen). Plasmids were further purified to remove residual endotoxins with additional Triton-X114 extractions as previously described (Stone et al., J Virol. 2006; 80(4):1762-72). Plasmid endotoxin level was <0.2 EU/ml for all constructs as confirmed by LAL endotoxin assay (Lonza Inc.). Gag protein secretion for all Gag-containing constructs was confirmed by p24 ELISA assay on supernatants from transfected 293T cells.

Transient Transfection and Western Blotting of Protein Constructs 293T cells were transiently transfected with plasmid constructs using Genjet-plus Transfection Reagent (Signagen Laboratories, Iamsville, Md.). A control transfection with GFP plasmid was used to confirm transfection efficiency of each reaction. Forty-eight hours later, supernatants were centrifuged and filtered with a 0.45 µm filter to remove debris. Filtered supernatant was reduced with 2-mercaptoethanol, loaded onto sodium-dodecyl sulfate-10% polyacrylamide gels (10% SDS-PAGE) (BioRad), electrophoresed, and blotted onto PVDF membranes (Pierce). The membranes were blocked using 5% (w/v) dry milk and then probed with goat anti-mouse CD40L antibody (R&D Systems), followed by incubation with anti-goat horseradish peroxidase-conjugated antibodies (Jackson Immunoresearch). The protein bands were developed onto X-ray film using chemiluminescence. To further evaluate high molecular weight complexes, a non-denaturing PAGE was performed in the absence of SDS and reducing agent.

CD40 In Vitro Activity Assay

A CD40 receptor-bearing reporter cell line (CD40-293-SEAP) was used to monitor CD40L-mediated activation. This 293-derived cell line constitutively expresses human CD40 receptor along with the gene for secreted alkaline phosphatase (SEAP) gene under control of NF-κB (Maurais et al., Virology. 2009; 385(1):227-32). Briefly, 80,000 CD40-293-SEAP reporter cells, grown in DMEM medium with 10% FBS, were plated in each well of a 96-well plate. A total of 100 µl of SPD-Gag-CD40L, SPD-CD40L or pcDNA3.1 transfected 293T supernatant was added to the reporter cells for 24 h in triplicate at various dilutions. On the following day, 10 µl/well of the supernatants was added to the wells of a 96-well assay plate together with 100 µl/well of QUANTI-Blue Alkaline Phosphatase substrate (InvivoGen). The plates were incubated for 20 min at 20° C. and OD was read at 650 nm.

DC Activation and Maturation Assay

Bone marrow-derived murine DCs were generated by standard methods (Inaba et al., Cellular immunology. 1995; 163(1):148-56) with the following modifications: Bone marrow cells were obtained from C57BL/6 mice and washed in RPMI 1640 media. The cells were then placed in tissue culture treated T75 flasks at a concentration of 1×106 cells per ml in 20 ml complete RPMI (RPMI 1640 with 10% FBS, 20 µg/ml gentamycin sulfate, 50 µM 2-mercaptoethanol), and 20 ng/ml murine recombinant GM-CSF and 10 ng/ml murine recombinant IL-4 (Peprotech, Rocky Hill, N.J.)). Cells were cultured at 37° C., 5% CO2 and on day 3, media was replaced with fresh complete RPMI containing cytokines. On day 5, cells were harvested and washed and resuspended in complete RPMI at 5×10E5 cells/ml. A total of 2 ml was added to each well of 6-well tissue culture treated plates. Subsequently, 300 µl of supernatant containing SPD-Gag-CD40L or DC activation cytokine mix (containing TNF, IL-1beta, IL-6, and PGE2) was added and cells were incubated for 36 hours. Cells were harvested and stained with hamster anti-mouse CD11c clone N418 PE-Cyanine7 conjugate (eBioscience, San Diego, Calif.) combined with one of the following antibodies: anti-mouse CD80 clone 16-10A1, anti-mouse CD86 clone GL1, anti-mouse CD40 clone 1C10, anti-mouse CD83 clone Michel-17, anti-mouse MHC Class II (I-A/I-E) clone M5-114.15.2, and anti-mouse CCR7 clone 4B12 (all from eBioscience). After flow cytometry analysis, the mean fluorescence intensity for each antibody was calculated for CD11c+ dendritic cells under each experimental condition. FlowJo 7.6.4 flow cytometry analysis software (FlowJo, Ashland, Oreg.) was used for analysis. Three independent wells were analyzed for each condition.

Production of Recombinant Adenovirus Containing Gag Antigen or SPD-Gag-CD40L

The construction of replication-deficient adenovirus (pAdEasy-1) containing codon-optimized Gag with a t-PA signal peptide or SPD-Gag-CD40L was performed as described by the manufacturer (AdEasy Adenoviral vector system, Agilent Technology, Inc.). Briefly, gene constructs were PCR amplified and cloned into the pAdenoVator-CMV5 shuttle vector (Qbiogene). CMV5-shuttle vector clones were confirmed by sequencing and then electroporated into BJ5183 cells containing the pAdEasy-1 plasmid to induce homologous recombination. The recombined pAdEasy-1 vector was linearized and transfected into AD293 cells (Stratagene). Following propagation in AD293 cells, recombinant Ad5 viruses were purified and concentrated using the Adeno-X Mega purification kit (Clontech). The concentration of Ad5 viral particles (vp) was determined by measuring the absorbance at 260 nm and 280 nm, and calculated using the formula vp/ml=OD260×viral dilution×1.1×1012. To determine infectious units, viruses were titered using the Adeno-x Rapid Titer kit (Clontech).

Mice and Immunization Schedule

Female BALB/c mice (7-8 weeks old) were used in all vaccination experiments. Animals were housed at the University of Miami under the guidelines of the National Institutes of Health (NIH, Bethesda, Md.). All animal experiments were performed in accordance with national and institutional guidance for animal care and were approved by the IACUC of the University of Miami Different groups of mice were immunized with plasmid DNA or Ad5 viruses for immunological and vaccinia challenge experiments.

DNA Immunization Schedule: DNA was injected intramuscularly into the quadriceps muscle of both hind limbs. Vaccinations were given three times at two-week intervals with 100 µg of SPD-Gag-CD40L or 100 µgGag plasmid mixed with either 20 µg of pcDNA3.1, pSPD-CD40L, or pIL-12p70 plasmids. Doses were administered in a total volume of 100 µl PBS (50 µl per limb). Control mice were injected with 100 µg of pcDNA3.1 empty vector.

Splenocyte preparation: Two weeks following the final DNA immunization, mice were euthanized and spleens were removed. Single cell splenocyte preparations were obtained by passage through a 40 µm nylon cell strainer (BD Falcon). Erythrocytes were depleted with lysis buffer (Sigma) and splenocytes washed thoroughly using R10 media (RPMI 1640 supplemented with 10% fetal bovine serum (FBS), 50 µM 2-mercaptoethanol, 100 U/ml of penicillin, 100 µg/ml streptomycin, and 10 mM HEPES).

Adenovirus Immunization Schedule: Five mice per group were immunized by intramuscular injection with Ad5 constructs twice at a two-week interval. Viral vector was injected in a total volume of 100 µl PBS (50 µl per limb) in the quadriceps muscles of both hind limbs.

Enzyme Linked Immunospot (ELISPOT) Assay

IFN-γ and IL-2 ELISPOT assays were performed to determine antigen specific cytokine secretion from immunized mouse splenocytes. ELISPOT assays were carried out per manufacturer's protocol (R&D Systems) using 96-well MAIP plates (Millipore). Freshly prepared vaccinated mouse splenocytes (1×105 cells/well) were added to each well of the plate and stimulated for 18 h at 37° C., 5% CO2 in the presence of HIV-1 Gag peptide AMQMLKFTI (10 µg/ml or as described). A c-myc peptide (negative control) and PMA/Ionomycin (positive control) were evaluated to calculate the minimum and maximum number of antigen-specific ELISPOTs respectively. After 18 h, spots were developed with AEC substrate kit (Vector Laboratories) according to manufacturer's instructions. The membrane was read by automated plate reader (CTL Immunospot) for quantitative analyses of the number of IFN-γ or IL-2 spots forming counts (SFC) per million cells plated, subtracting negative control values.

T Cell Receptor Avidity ELISPOT Assay

ELISPOT was performed as described, stimulating the cells with 1 µg/ml, 10-3 µg/ml, or 10-5 µg/ml of Gag peptide (AMQMLKFTI) to evaluate the number of T cells able to secrete IFN-γ at limiting peptide concentrations.

ELISA Assay for Anti-Gag IgG Responses

Anti-Gag antibody production was measured by ELISA assay. HIV-1 p55 Gag protein (10 µg/ml) was coated onto 96-well ELISA plates overnight at 4° C. Mouse sera at varying dilutions (1:30, 1:120, 1:480 and 1:1,920) were added to Gag-coated wells and incubated at room temperature for 2 h with shaking. After the plates were washed, Gag antigen specific IgG antibodies were detected using alkaline phosphatase-conjugated goat anti-mouse IgG (Jackson Immunoresearch Inc.). Signal was developed using Blue-Phos substrate (KPL, Inc.). Plates were analyzed using a 96-well plate absorbance reader at 650 nm. Endpoint titers were calculated as the highest dilution with more than twice the background absorbance of control wells.

Vaccinia-Gag Virus Challenge

Two weeks following DNA or Ad5 immunization, mice were challenged i.p with 1×107 vp vaccinia-gag virus vP1287 as described (Qiu et al., J Virol. 1999; 73(11):9145-52). Five days following challenge, mice were sacrificed and ovaries were removed and homogenized in 500 µl PBS. For measurement of virus titers, samples were sonicated and evaluated in triplicate by 10-fold serial dilution on Vero cells plated in 24 well plates. Following 48-hour incubation, the plates were stained with 0.1% (w/v) crystal violet in 20% ethanol. Plaques were counted and expressed as the plaque-forming units (PFU) of virus in total lysate volume (PFU/mouse).

Statistical Analysis

All error bars represent standard error from the mean. Graph pad Prism 6.0 software was used to calculate significance by one way ANOVA for multiple comparison or by two-tailed Student's t test, comparing mice vaccinated with SPD-Gag-CD40L, Gag, or Gag antigen adjuvant (SPD-CD40L or IL-12p70). In all figures, p values are labeled by asterisks denoting $p<0.05$ (*), $p<0.01$ (), and $p<0.001$ (*). Any unlabeled comparisons were not statistically significant between groups.

Results

Construction and Expression of Multi-Trimer SPD-Gag-CD40L

CD40L is naturally produced as a Type II membrane protein on the surface of activated CD4+ T cells and other cells. When an activated CD4+ T cell comes in contact with a DC, an immunological synapse forms that clusters CD40 receptors in the DC membrane, which in turn initiates downstream events in the DC. To mimic this situation using a soluble CD40L protein, a many trimer form of CD40L is needed since single trimers of CD40L do not provide an effective stimulus (reviewed in Kornbluth et al., International Reviews of Immunology. 2012; 31(4):279-88). Consequently, multi-trimer soluble forms of CD40L were developed by fusing SPD with the CD40L extracellular domain, where SPD provides a self-assembling scaffold for multimerization. SPD-CD40L mimics the multivalent nature of membrane CD40L and was previously shown to activate B-cells, macrophages and dendritic cells in vitro and enhance vaccine responses in vivo. In the previous vaccine studies, antigen and multi-trimer CD40L adjuvant were used as separate molecules and mixed together for immunization (Stone et al., J Virol. 2006; 80(4):1762-72). To further improve this vaccine design, an immunogen was developed that incorporated antigen (exemplified by HIV-1 Gag) and multi-trimer CD40L into a single polypeptide, SPD-Gag-CD40L. The p55 portion of Gag was inserted into protein sequence for the collagen-like trimeric "arm" of SPD, between amino acid 105 and 106 of mouse SPD within the SPD-CD40L construct (FIG. 5A). To show that SPD-Gag-CD40L has the expected structure, protein was produced by transfecting 293T cells with pSPD-Gag-CD40L plasmid DNA. Using reducing conditions, SDS-PAGE, and western blotting for CD40L, the resulting culture supernatant was found to contain a single protein of the expected size of 105 kDa (FIG. 6A). A single 105 kDa band was also observed using antibody to the p24 portion of Gag (data not shown). To confirm that SPD-Gag-CD40L forms a large protein complex, PAGE and western blotting were performed using a non-denaturing gel in the absence of reducing agents. Multiple bands were observed at >200 kDa molecular weight, demonstrating the formation of large multimeric complexes (FIG. 6B).

Biological Activity of Multi-Trimer Soluble SPD-Gag-CD40L

To assess the ability of SPD-Gag-CD40L to stimulate the CD40 receptor, a CD40-bearing indicator cell line was used as described previously (Maurais et al., Virology. 2009; 385(1):227-32). In this cell line, CD40 stimulation activates the NF-$\kappa$B pathway which in turn activates the $\kappa$B promoter driving the expression of secreted alkaline phosphatase (SEAP) that is measured by a colorimetric enzymatic assay. Supernatants from 293T cells transfected with pSPD-Gag-CD40L or parent pSPD-CD40L stimulated these CD40 receptor-bearing cells to produce SEAP (FIG. 7A). In contrast, supernatants from 293T cells transfected with pcDNA3.1 empty vector were inactive. To evaluate the biological activity of the soluble forms of CD40L, bone marrow-derived dendritic cells were treated with supernatants from 293T cells transfected with either pSPD-Gag-CD40L or pcDNA3.1 empty vector. A cytokine mix (TNF, IL-1beta, IL-6, and PGE2) was used to "mimic" an inflammatory environment and used as a positive control. As shown in FIG. 7B, CD80, CD86 and CCR7 were significantly upregulated by SPD-Gag-CD40L supernatant compared to pcDNA3.1 control supernatant. In contrast, CD40 expression was significantly reduced, consistent with endocytosis of CD40 following SPD-Gag-CD40L ligation.

As a DNA Vaccine, Multi-Trimer Soluble SPD-Gag-CD40L was More Immunostimulatory than Separate Plasmids for Gag Antigen and SPD-CD40L Adjuvant Plasmid DNA for SPD-Gag-CD40L (pSPD-Gag-CD40L) was evaluated for its ability to enhance immune responses as a DNA vaccine. Mice were vaccinated three times at two-week intervals with an intramuscular injection of 100 µg of pSPD-Gag-CD40L plasmid DNA. For comparison, 100 µg of plasmid DNA encoding soluble secreted Gag antigen (pGag) was mixed with 20 µg of separate plasmids encoding either SPD-CD40L or IL-12p70 adjuvants or pcDNA3.1 empty control vector. The vaccination schedule is outlined in FIG. 8A. Two weeks following the third vaccination, T cell responses were analyzed by IFN-$\gamma$ and IL-2 ELISPOT assays using the Kd-restricted HIV-1 Gag peptide AMQMLKFTI to stimulate mouse splenocytes. As shown in FIG. 8B, there was a significant increase in Gag-specific CD8+ T cell responses measured by IFN-$\gamma$ ELISPOT in splenocytes from mice vaccinated with pSPD-Gag-CD40L compared to mice vaccinated with pGag alone or a mixture of separate plasmids for pGag antigen combined with either pSPD-CD40L or pIL-12p70 adjuvants. Comparing pSPD-Gag-CD40L to unadjuvanted pGag alone, mean IFN-gamma ELISPOT responses increased >60-fold. In contrast, the responses to separate plasmids for pGag mixed with pSPD-CD40L or pIL-12p70 adjuvants were much less. Similarly, IL-2 ELISPOT responses were significantly increased for pSPD-Gag-CD40L compared to pGag alone or separate plasmids for pGag antigen mixed with pSPD-CD40L or pIL-12p70 adjuvants (FIG. 8C). Comparing pSPD-Gag-CD40L to pGag alone, mean IL-2 ELISPOT responses increased >10-fold.

To determine if high avidity CD8+ T cells were present, CD8+ T cell IFN-$\gamma$ ELISPOT responses were tested at limiting AMQMLKFTI peptide concentrations. As shown in FIG. 9A, pSPD-Gag-CD40L significantly increased IFN-$\gamma$ ELISPOT responses compared to other vaccine groups at all peptide dilutions. At 10 pg/ml of AMQMLKFTI peptide, IFN-gamma ELISPOT responses were only detectable from the splenocytes of mice vaccinated with pSPD-Gag-CD40L. Overall, these data show that pSPD-Gag-CD40L markedly enhanced anti-Gag CD8+ T cell immune responses and CD8+ T cell avidity levels compared to alternative vaccination approaches.

To evaluate humoral immune responses, Gag-specific IgG antibody titers in mice serum were measured by ELISA assay two weeks following vaccination. As shown in FIG. 9B, all vaccine groups induced similar Gag-specific IgG responses compared to Gag vaccination alone and there were no significant differences between groups.

Single-Trimer Gag-CD40L Fusion Protein Failed to Enhance Immune Responses Compared to Multi-Trimer SPD-Gag-CD40L We next evaluated the role of multi-trimerization by the SPD scaffold on the immune response. The N-terminus of SPD is involved in disulfide bonding and is required to form 4-trimer complexes (Crouch et al., J Biol Chem. 1994; 269(25):17311-9). Deleting this N-terminal portion of SPD (amino acids 106-256 in murine SPD) results in a single-trimer form of Gag-CD40L (pTrimer-Gag-CD40L). A t-PA signal peptide was added at the N-terminus sequence to direct protein secretion, followed by HIV-1 Gag, amino acids 106-256 of murine SPD, and then amino acids 47-260 of murine CD40L. Lacking the multimerizing "hub" of SPD, this construct is expected to form single trimer molecules containing Gag and CD40L. To examine the biological activity of pTrimer-Gag-CD40L, protein was made by transfecting 293T cells with pTrimer-Gag-CD40L plasmid and testing the resulting supernatant in the CD40 NF-κB SEAP indicator cell line assay described above. As expected, with only one trimer of CD40L, the pTrimer-Gag-CD40L-encoded protein had little or no activity in this assay (data not shown), confirming previous reports that single trimers of CD40L are essentially unable to stimulate CD40 receptor-bearing cells (Holler et al., Mol Cell Biol. 2003; 23(4):1428-40; Haswell et al., Mol Cell Biol. 2003; 23(4):1428-40). Mice were then vaccinated with DNA vaccines encoding pGag (unadjuvanted antigen alone), pTrimer-Gag-CD40L (single trimer of Gag antigen fused to CD40L) or pSPD-Gag-CD40L (multi-trimer of Gag antigen fused to CD40L). Mice vaccinated with pSPD-Gag-CD40L showed a significant increase in IFN-gamma ELISPOT responses compared to unadjuvanted pGag alone or pTrimer-Gag-CD40L which contains Gag and CD40L but lacks the multi-trimer structure (FIG. 10A). Also observed was a significant increase in IL-2 ELISPOT responses for the pSPD-Gag-CD40L group vs. pTrimer-Gag-CD40L (FIG. 10B).

Vaccination with pSPD-Gag-CD40L Protected Mice from Virus Challenge by Vaccinia-Gag To determine the protective efficacy of the CD8+ T cells induced by DNA vaccination with pSPD-Gag-CD40L, vaccinated mice were challenged by vaccinia virus expressing the HIV-1 Gag antigen (vP1287 or vaccinia-Gag) (Qiu et al., J Virol. 1999; 73(11):9145-52). Two weeks following final DNA vaccination, mice were challenged intraperitoneally with vaccinia-gag (10E7 PFU). As shown in FIG. 11A, mice vaccinated with pSPD-Gag-CD40L had a significantly less tissue virus in ovaries compared with unvaccinated animals (p<0.001) or animals vaccinated with pGag DNA vaccine alone (p<0.05) when vaccinia PFUs were measured on day 5 following vaccinia-Gag challenge. Overall, 4 out of 13 mice vaccinated with pSPD-Gag-CD40L had undetectable viral titers (less than 10 PFU in total ovary lysate).

To determine the effect of CD40L multi-trimerization on the protection conferred by vaccination, mice were vaccinated with pcDNA3.1 empty vector, pGag antigen alone, pTrimer-Gag-CD40L, or pSPD-Gag-CD40L (FIG. 11B). There were no significant differences in vaccinia-Gag titers between pGag and pTrimer-Gag-CD40L groups, with both groups reducing viral load by ~1 log compared to pcDNA3.1 treated mice. In contrast pSPD-Gag-CD40L reduced mean viral load by ~3 log in this experiment.

Mice Vaccinated with an Ad5-SPD-Gag-CD40L Viral Vector were Completely Protected from Vaccinia-Gag Challenge While DNA vaccination is effective in mice, its translation to humans has proved difficult. Instead, most currently tested HIV-1 vaccines have used viral vectors, especially adenovirus-5 (Ad5). Consequently, the nucleic acid sequences for Gag alone (Ad5-Gag) or SPD-Gag-CD40L (Ad5-SPD-Gag-CD40L) were cloned into replication defective Ad5 and used to vaccinate mice twice at two-week intervals with 1×10E9 viral particles (vp) i.m. Two weeks following the final vaccination, mice were challenged intraperitoneally with vaccinia-Gag (107 PFU). Remarkably, all 5 mice vaccinated with Ad5-SPD-Gag-CD40L had no detectable vaccinia virus in their ovaries (<10 PFU/mouse) (FIG. 12), which was statistically significant compared with either the Ad5-Gag or unvaccinated groups (p<0.01). Overall there was a 7-log reduction in vaccinia virus titers when Ad5-SPD-Gag-CD40L was compared to Ad5-Gag. A repeat experiment gave similar results (data not shown). These data support the strategy of introducing SPD-Gag-CD40L into viral vector vaccines such as Ad5.

Discussion

Stimulation through the CD40 receptor is important for generating CD8+ T cell responses under non-inflammatory conditions. Numerous studies in mice have shown that agonistic antibodies to CD40 can activate strong responses to vaccination. However, the translation of agonistic anti-CD40 antibody to the clinic has proved challenging due to concerns about toxicity, depletion of CD40-positive cells such as B cells, and the relatively limited effectiveness of agonistic anti-CD40 antibody in humans when compared to studies in mice.

An important advance in the understanding of the CD40L/CD40 system has been the recognition that DC activation requires clustering of the CD40 receptor in order to stimulate the formation of an intracytoplasmic signaling complex. For agonistic anti-CD40 antibodies, clustering requires that the antibodies be mounted via FcRs on an adjacent cell. Under conditions where an adjacent FcR-bearing cell is absent, agonistic anti-CD40 antibodies are not effective.

Keeping in mind this requirement for CD40 receptor clustering, we and others have examined various multi-trimer forms of CD40L as agonists for murine, macaque, and human DCs. These molecules were made as fusion proteins between a multimerization scaffold such as SPD and the extracellular domain of CD40L. SPD is an ideal scaffold because CD40L is a Type II membrane protein in which the C-terminus faces outward and SPD forms a plus sign-shaped structure where the N-terminus is at the central "hub" and the C-terminus faces conveniently outward. When used as a DNA vaccine, multi-trimer SPD-CD40L was an effective adjuvant when added to plasmid DNA encoding an antigen and led to significantly increased antigen-specific CD8+ T cell responses. However, we hypothesized that the vaccine response might be even stronger if the antigen and multi-trimer CD40L protein sequences were physically linked rather than being mixed together for vaccination. Consequently, a tripartite fusion protein was constructed that combined the SPD multimerization scaffold, HIV-1 Gag as an antigen, and murine CD40L as the adjuvant (SPD-Gag-CD40L) (FIGS. 5A and 5B).

As a first step, non-denaturing PAGE was used to show that SPD-Gag-CD40L protein is indeed a high molecular weight multimer complex (FIGS. 6C and 6D). In vitro, this multi-trimer CD40L molecule could stimulate a CD40 receptor-bearing indicator cell line that reports out NF-κB activation by releasing secreted alkaline phosphatase (SEAP) (FIG. 7A). As a control, a molecule was made in which the N-terminal "hub" of SPD was deleted, leading to a 1-trimer CD40L molecule that had little or no activating in this NF-κB activation assay (data not shown). This control revealed the critical importance of the multi-trimer structure in forming a highly actively form of CD40L, as previously demonstrated by Haswell et al. (Eur J Immunol. 2001; 31(10):3094-100). As expected, SPD-Gag-CD40L stimulated murine bone marrow-derived DCs in vitro to express cell surface markers of activation (FIG. 7B). While these data do not present direct evidence that the SPD-Gag-CD40L constructs folds into the structure outlined in FIG. 5B, we consider the ability of the construct to form biologically active trimers to provide initial evidence that functional trimers are being generated. In preliminary experiments we have also observed biological activity for SPD-CD40L fusions with alternative antigens including gp100 and HIV-1 Env gp120 (data not shown), supporting the concept that SPD-CD40L fusions with antigen is broadly applicable as a vaccine design strategy.

In vivo, plasmid DNA (pSPD-Gag-CD40L) was tested as a vaccine (FIG. 8A) and compared to vaccination with plasmid DNA for Gag alone (pGag) or an mixture of separate pGag antigen plasmid with pSPD-CD40L adjuvant plasmid. Strikingly, pSPD-Gag-CD40L elicited the strongest CD8+ T cell responses as judged by the number of IFN-γ and IL-2 producing cells in an ELISPOT analysis (FIGS. 8B, 8C, 10A and 10B). pSPD-Gag-CD40L elicited CD8+ T cells with remarkably increased avidity for the Gag peptide antigen (FIG. 9A). However, as we and others have previously described, multi-trimer CD40L is not a good adjuvant for antibody responses (FIG. 9B), which emphasizes the special effects of CD40L on DCs and subsequent CD8+ T cell responses. While CD40L plays a role in promoting B-cell proliferation and immunoglobin class switching, several reports have shown that strong CD40 stimulation can also prevent the movement of B cells into germinal centers, block the development of memory B cells, and impair B-cell differentiation into antibody-secreting plasma cells. We have also observed similar responses by SPD-CD40L in previous studies. We propose that SPD-Gag-CD40L is unable to enhance antibody responses through one or more of these mechanisms.

In addition, these CD8+ T cell responses were protective as judged by the 2-3 log reduction in tissue viral load after challenging the mice with vaccinia-Gag (FIGS. 11A and 11B). However, we note that viral titers following SPD-Gag-CD40L vaccination were not significantly different than viral titers following vaccination with Gag plus SPD-CD40L, despite a large difference in interferon gamma and IL-2 ELISPOT responses between the two groups. Partly this may reflect the inherent variability of DNA vaccine immune responses, given that 4/13 mice given SPD-Gag-CD40L were able to clear virus while Gag plus SPD-CD40L was unable to reduce titer below 104 pfu/mouse. Overall, Gag plus SPD-CD40L gave a similar mean viral titer to Gag plus empty vector. Since DNA vaccination is a relatively inefficient way to deliver a genetic construct, an adenoviral vector (Ad5) was also used to vaccinate mice. Very remarkably, there was a ~7 log reduction in tissue viral load in mice vaccinated with Ad5-SPD-Gag-CD40L and no challenge virus could be detected (FIG. 12).

To account for the effectiveness of the SPD-Gag-CD40L vaccine design, three factors should be considered: (1) Use of multi-trimer CD40L to cluster the CD40 receptor and thereby activate DCs; (2) Role of CD40L in targeting antigen to CD40 receptor-bearing DCs; and (3) simultaneous delivery of both the Gag antigen and CD40L adjuvant to the same DC at the same time.

(1) Regarding the multi-trimer nature of CD40L in SPD-Gag-CD40L, it is worth noting that others have previously made antigen-CD40L fusion proteins. Xiang et al. (J. Immunol. 2001; 167(8):4560-5) fused a tumor antigen to the C-terminal end of CD40L in a position that could conceivably impair binding of the ligand to the CD40 receptor. No data were presented to rule out this concern, but the vaccine's effectiveness was modest. Similarly, Zhang et al. fused a tumor antigen onto the N-terminus of the CD40L extracellular domain and delivered this construct using an adenovirus vector. In this case, the molecular design allowed for CD40L to bind unimpaired to its receptor. Even so, the effectiveness of this vaccine was relatively modest (Proc Natl Acad Sci USA. 2003; 100(25):15101-6). This is expected when a 1-trimer form of CD40L is used rather than a receptor-clustering multi-trimer construct such as SPD-Gag-CD40L.

(2) Regarding the targeting of antigen to CD40 on DCs, this has emerged as a very desirable property for vaccine design. Barr et al. showed that antigen conjugated to anti-CD40 antibody elicited strong vaccine responses, although toxicity and anti-idiotypic antibody development are drawbacks to this approach (Barr et al., Immunology. 2003; 109(1):87-92). In vitro, Flamar et al. showed that anti-CD40 antibody conjugated to five HIV antigenic peptides could be taken up by human DCs in vitro and the antigens were then presented to T cells from the blood of HIV-infected subjects (Flamar et al., AIDS. 2013 Aug. 24; 27(13):2041-51). In vivo, Cohn et al. found that conjugating antigen to anti-CD40 antibody broadened the types of DCs that crosspresent antigen to T cells to include BDCA1(+) DCs in addition to standard crosspresentation by BDCA3(+) DCs (J Exp Med. 2013; 210(5):1049-63. PMCID: 3646496). However, DC crosspresentation alone does not generate CD8+ T cell responses. As shown by Bonifaz and Steinman, antigen conjugated to anti-DEC205 antibody was targeted to DCs but the unactivated DCs lead to abortive T cell responses and subsequent tolerance. As they showed, the induction of CD8+ T cell responses by the anti-DEC205 antibody/antigen vaccine also required the addition of a DC-activating CD40 stimulus ((Bonifaz et al., J Exp Med. 2002; 196(12): 1627-38). Thus, targeting of antigen to CD40 is helpful but not sufficient for DC-mediated T cell activation and expansion. Indeed, targeting a vaccine antigen to unactivated DCs could be counterproductive and lead to tolerance rather than augmented vaccine responses.

(3) Regarding the need for delivery of both antigen and adjuvant to the same DC at the same time, this issue was recently examined by Kamath et al. ((J Immunol. 2012; 188(10):4828-37). When antigen was delivered to DCs in the absence of adjuvant, antigen-specific T cells were induced to proliferate but did not subsequently differentiate into effector cells. Instead, effective immunity was only induced when the test vaccine provided antigen and adjuvant to the same individual DCs within a short window of time. These parameters are fulfilled by the design of SPD-Gag-CD40L because the antigen and adjuvant are linked in time and space as parts of the very same molecule.

In conclusion, a vaccine was developed that combines multi-trimer CD40L as an adjuvant covalently linked to HIV-1 Gag antigen. Extremely strong and highly protective CD8+ T cell responses were induced by this vaccine, especially when the construct was incorporated into an Ad5 vector. Since other antigens can be substituted for HIV-1 Gag in SPD-Gag-CD40L, this immunogen design suggests a general method for constructing an effective preventative and/or therapeutic vaccine for infections and tumors for which a strong CD8+ T cell response is required.

Example 2: Cancer Immunotherapy

Previous studies have shown that plasmid DNA vaccination using an exogenous gene encoding tumor associated antigens can induce cancer-specific CTLs with antitumor activity. A second-generation improvement on this approach is the targeting of antigen to dendritic cells (DC) by fusion to antibodies or natural ligands that bind dendritic cell receptors. Recently it has been shown that targeting of antigen to DC via CD40 is particularly effective at inducing cross presentation of targeted antigens.

In this example we explored the use of CD40 ligand to target tumor antigen to DC. A DNA vaccine was generated encoding a single fusion protein composed of the spontaneously multimerizing gene Surfactant Protein D (SPD), gp100 tumor antigen, and the extracellular domain of CD40L. This "third generation" antigen-CD40L approach was developed to both target antigen to DC and optimally activate dendritic cells by clustering CD40 on the cell membrane. SPD-gp100-CD40L was expressed as a single 110 kDa protein strand that self-assembles inside cells into a molecule with four trimeric arms containing 4 trimers of CD40L. The protein was biologically active on dendritic cells and able to induce CD40-mediated signaling. SPD-gp100-CD40L was evaluated in a B16-F10 melanoma DNA vaccine model either alone or in combination with plasmids encoding IL-12p70 and GM-CSF. Vaccination with SPD-gp100-CD40L+IL-12p70 GM-CSF significantly increased survival and inhibited tumor growth compared to all other treatments. Expression of gp100 and SPD-CD40L as separate molecules did not enhance survival, suggesting incorporation of gp100 within the SPD-CD40L polymer is required for activity. These data support a model where gp100 antigen incorporated within SPD-CD40L multi-trimers targets antigen to DC in vivo, induces activation of these DC, increases cross-presentation of gp100 antigen, and generates a protective anti-tumor T cell response when given in combination with IL-12p70 and GM-CSF molecular adjuvants.

Cancer vaccination has attracted renewed attention as a therapy for the treatment of tumor growth and metastasis. The use of Tumor Associated Antigens (TAA) is particularly promising. Therapeutic effects specific to cancer cells can be generated through the careful selection of TAA preferentially expressed on tumor cells. In particular, it has been reported that DNA vaccination using an exogenous plasmid encoding a TAA can induce cancer-specific cytotoxic T lymphocytes (CTL) with antitumor activity. However, optimal CTL activity requires that the antigen be selectively and efficiently presented by antigen presenting cells (APC) such as dendritic cells (DC), which play a pivotal role in the initiation, programming and regulation of cancer-specific immune responses. One strategy to enhance the effectiveness of DNA vaccines encoding weakly immunogenic antigens is by co-delivering genes encoding molecular adjuvants that stimulate DC. TNF superfamily ligands (TNFSF) are costimulatory molecules involved in DC and T cell activation and have previously been tested as adjuvants to enhance immune responses in several vaccination studies, in particular the DC activating molecule CD40L, the cognate ligand for CD40.

Melanoma-specific antigen gp100, encoded within DNA or viral vector vaccines, is known to induce measurable immune responses and suppress tumor growth. However, molecular adjuvants could enhance the overall immune response to this antigen, inducing an effective immune response able to prevent tumor growth. As important, targeting of tumor antigens directly to DC using the DC receptor DEC-205 has previously been shown to increase immune responses. Similarly, it has also been shown that delivery of antigens to DC via CD40 can enhance cross-presentation of antigen to CD8+ T cells via MHC I.

CD40L stimulation increases effector T cell differentiation and also induces the production of a variety of cytokines, such as IL-12p70. Based on previously published data, a 4-trimer soluble form of CD40L has been shown to be particularly effective as a vaccine adjuvant. This 4-trimer soluble form was achieved using the scaffold protein Surfactant Protein D (SPD), a collectin family member that spontaneously forms a plus-sign-shaped molecule with four trimeric arms, generating a 4-trimer soluble complex.

In addition to CD40L, other adjuvants previously tested in cancer vaccine models include GM-CSF and IL-12p70. Systemic co-administration of IL-12p70 or GM-CSF have been shown to induce antitumor immunity. Studies have also evaluated these cytokines as DNA-encoded adjuvants for DNA vaccines where they have shown modest efficacy.

In the present study, the fusion protein SPD-gp100-CD40L was generated encoding murine CD40L extracellular domain fused to the collagen-like domain of murine SPD, with gp100 antigen inserted within the SPD coding region. We reasoned that these soluble CD40L multi-trimers would deliver gp100 to DC while simultaneously activating the DC, thereby inducing an enhanced CD8+ T cell CTL response. As we report, SPD-gp100-CD40L protein was stable, formed large polymeric complexes, and was biologically active on DC, suggesting proper assembly of CD40L trimers. Co-delivery of SPD-gp100-CD40L, GM-CSF, and IL-12p70 plasmids by intramuscular injection enhanced survival of mice challenged with B16-F10 and significantly suppressed tumor growth. This response was not observed with any other DNA vaccine combination, and was not observed when gp100 and SPD-CD40L were delivered as separate molecules, either in presence or absence of GM-CSF and IL-12p70. Overall, these data support the hypothesis that SPD-gp100-CD40L, when augmented with GM-CSF and IL-12p70 cytokines, targets gp100 antigen to DC in situ, activates these DC via CD40 stimulation, and induces an immune response that controls tumor growth and enhances survival.

Materials and Methods

Construction and Preparation of DNA Plasmids

Plasmid encoding human glycoprotein 100 (pgp100) was a gift of Dr. Patrick Hwu. Plasmid encoding the 4-trimer soluble form of murine SPD-CD40L was generated as previously described (Stone et al., J Virol. 2006; 80(4):1762-72). To construct pSPD-gp100-CD40L, DNA encoding amino acids 25 to 596 (sequence KVPRNQD to EAGLGQV) of human gp100, incorporating the full extracellular domain or gp100, was inserted between amino acids 105 and 106 of mouse SPD within construct SPD-CD40L (i.e. between peptide sequences GERGLSG and PPGLPGI of murine SPD). Murine IL-12p70 plasmid pIL-12 was purchased from Invivogen and encodes a single chain dimer of IL-12 p35 and p40 (InvivoGen). Murine GM-CSF plasmid was constructed using a codon-optimized gene encoding murine GM-CSF inserted into plasmid pcDNA3.1. Clone pgp100-IRES-SPD-CD40L was generated by placing an IRES sequence between human gp100 (amino acids 1-594) and murine SPD-CD40L (Zhou et al., Proc Natl Acad Sci USA. 2008; 105(14):5465-70). All plasmids were propagated in *Escherichia coli* strain TOP10. Highly purified, endotoxin-free DNA plasmid preparations were produced using the Qiagen endofree GIGA plasmid kit. Plasmids were further purified using a Triton-X114 purification method as previously described (Stone et al., J Virol. 2006; 80(4):1762-72). All plasmid endotoxin levels were <0.2 EU/ml as confirmed by LAL endotoxin assay (Lonza Inc.).

Transient Transfections and Western Blotting of Fusion Protein Constructs 293T cells were transiently transfected with plasmid constructs using Genjet Plus transfection reagent (Signagen Laboratories). Forty-eight hours later, supernatants were centrifuged and filtered. Supernatants were loaded onto a sodium-dodecyl sulfate-10% polyacrylamide gel (BioRad) in the presence of DTT, electrophoresed, and blotted onto PVDF membrane (Pierce). The membrane was blocked using 5% (w/v) dry milk and then probed with goat anti-mouse CD40L antibody (R&D Systems), followed by incubation with anti-goat horseradish peroxidase-conjugated antibodies (Jackson Immunoresearch). The protein band was developed onto X-ray film using chemiluminescence. For analytical light scattering analysis, 293T cells were transiently transfected with the pSPD-gp100-CD40L construct and supernatant was collected and then concentrated 10-fold using an Amicon centrifugal filtration system with 100 kDa cutoff (Millipore).

CD40 SEAP In Vitro Activity Assay

The CD40 receptor bearing reporter cell line CD40-293-SEAP was used to monitor CD40L mediated activation. This 293-derived cell line constitutively expresses human CD40 receptor along with the gene for secreted alkaline phosphatase (SEAP) under the control of NF-□B [59]. Briefly, 80,000 CD40-293-SEAP reporter cells grown in DMEM medium with 10% FBS were plated in each well of a 96-well plate. A total of 100 µl of SPD-gp100-CD40L, SPD-CD40L or pcDNA3.1 transfected 293T cell supernatant was added to the cells in triplicate at various dilutions. After 18 hours, 10 µl/well of the supernatant from each well was added to a 96-well assay plate together with 100 µl/well of QUANTI-Blue Alkaline Phosphatase substrate (InvivoGen). Wells were incubated for 20 min at 20° C. and read at 650 nm in a 96-well plate reader.

DC Activation and Maturation Assay

Bone marrow derived DC were generated by standard methods with the following modifications. Bone marrow cells were obtained from C57BL/6 mice and washed in RPMI 1640 media. The cells were then placed in a non-tissue culture treated T75 flask at a concentration of 1×10⁶ cells per ml in 20 ml complete RPMI (RPMI 1640 with 10% FBS, 20 µg/ml gentamycin sulfate, 50 µM Mercaptoethanol), 20 ng/ml murine recombinant GM-CSF and 10 ng/ml murine recombinant IL-4 (Peprotech, Rocky Hill, N.J.)). Cells were cultured at 37° C., 5% CO2 and on day 3, media was replaced with fresh complete RPMI containing cytokines. On day 5, cells were harvested, washed and resuspended in complete RPMI at 5×10⁵ cells/ml. A total of 1×10⁶ cells were added to each well of 6-well non-tissue culture treated plates. Subsequently, 300 µl of supernatant containing SPD-gp100-CD40L, pcDNA3.1 control supernatant, or cytokine mix positive control (15 ng/ml IL-1beta, 5 ng/ml TNFalpha, and 1 µg/ml PGE2 final concentration) was added and cells were incubated for 36 hours. Cells were harvested and stained with Hamster anti-mouse CD11c clone N418 PE-Cyanine7 conjugate (eBioscience, San Diego, Calif.) combined with each of the following antibodies: anti-mouse CD80 clone 16-10A1, anti-mouse CD86 clone GL1, anti-mouse CD40 clone 1C10, anti-mouse CD83 clone Michel-17, anti-mouse MHC Class II (I-A/I-E) cloneM5-114.15.2, and anti-mouse CCR7 clone 4B12 (all from eBioscience). After flow cytometry analysis, the mean fluorescence intensity was calculated for gated CD11c+ dendritic cells under each experimental condition. FlowJo 7.6.4, flow cytometry analysis software, (FlowJo, Ashland, Oreg.) was used for analysis. Three independent wells were analyzed for each condition.

Tumor Immunotherapy Studies

Female C57BL/6 mice (7-8 weeks old) were used in all experiments. Animals were housed at the University of Miami under the guidelines of the National Institutes of Health (NIH, Bethesda, Md.) Animal experiments were performed in accordance with national and institutional guidance for animal care and were approved by the IACUC of the University of Miami A total of 50,000 B16-F10 cells were injected i.d. into the left flank. Mice were then injected i.m. with plasmid DNA on day 3, 10, and 17 following tumor challenge into both hind quadriceps muscles. Mice received a mixture of from one to three plasmid constructs. Empty vector pcDNA3.1 was used as filler to ensure all groups received the same total micrograms of plasmid. Tumor volume was measured 3 times per week using a digital caliper, measuring the longest diameter (a) and shortest width (b) of the tumor. Tumor volume was calculated by the formula V (mm3)=0.5×ab2. Animals were euthanized when tumors reached >1500 mm3. For GVAX vaccination, B16-F10 tumor cells expressing GM-CSF, kindly provided by Dr. Glenn Dranoff, were irradiated (5,000 rad) and 1×10⁶ cells were injected subcutaneously on the right flank on day 3, 6, and 9.

Histology

Tumors were harvested for histological analysis on day 15-20, fixing the tissue overnight at 4° C. in 10% formalin prior to embedding in paraffin. Serial 4 µm sections were then stained with hematoxylin and eosin (H&E) to evaluate for the presence of lymphocyte infiltration.

Statistical Analysis

Graph pad Prism 6.0 software was used to calculate significance by two-tailed Student's t test. In all figures, p values were labeled by asterisks for p<0.05 (*), p<0.01 (), and p<0.001 (*).

Results

Construction and Expression of Multi-Trimeric Soluble SPD-Gp100-CD40L

Previous studies have shown that CD40L-mediated signaling is required for functional CTL memory development against tumors. Similarly, we have previously shown that injection of plasmid DNA expressing SPD-CD40L into B16-F10 tumors can slow tumor growth when combined with TLR agonists. CD40L mediates the co-stimulation, activation, and maturation of dendritic cells (DC), and this function is critical for the induction of an effective T cell mediated immune response. Previous research has shown that monoclonal antibodies targeting DC surface protein DEC-205 can target cancer antigens to DC in vivo, inducing a protective immune response. We surmised that SPD-CD40L could similarly be used as a carrier to transport tumor associated antigens (TAA) to DC in vivo by incorporating the antigen within the SPD collagen-like domain of SPD-CD40L. We constructed the plasmid pSPD-gp100-CD40L, where human gp100 is fused between amino acids 105 and 106 of the collagen-like domain of murine SPD-CD40L (FIG. 13A) and SEQ ID NO 5 and SEQ ID NO 6. A model of the expected 4-trimer complex is shown in FIG. 13B. Following transfection of pSPD-gp100-CD40L into 293T cells, secreted SPD-gp100-CD40L was detected at the expected size of 110 KDa by SDS-PAGE Western blot in the presence of DTT (FIG. 13C).

Biological Activity of SPD-Gp100-CD40L

To confirm that SPD-gp100-CD40L retains biological activity, an SEAP cell line reporter assay was performed as described previously. We monitored the ability of SPD-gp100-CD40L supernatant to drive NF-kappaB-mediated expression of the SEAP reporter enzyme. Empty vector pcDNA3.1 transfected 293T cell supernatant was used as a negative control. As shown in FIG. 14A, both SPD-CD40L and SPD-gp100-CD40L induced SEAP activity at a similar level in a dose-dependent manner when compared to empty vector.

Next, we evaluated the ability of SPD-gp100-CD40L to activate bone marrow derived DCs. DCs were cultured with supernatant from 293T cells transfected with either empty vector pcDNA3.1 or pSPD-gp100-CD40L. A cytokine mix containing recombinant IL-1beta, TNFalpha, and PGE2 (Mimic) was used as a positive control. We observed a significant increase in CD80, CD86 and CD83 MFI (comparing pcDNA3.1 to pSPD-gp100-CD40L supernatant). SPD-gp100-CD40L was moderately active compared to the Mimic positive control.

SPD-Gp100-CD40L DNA Alone Did not Inhibit B16-F10 Tumor Growth in Mice

Figure 15:
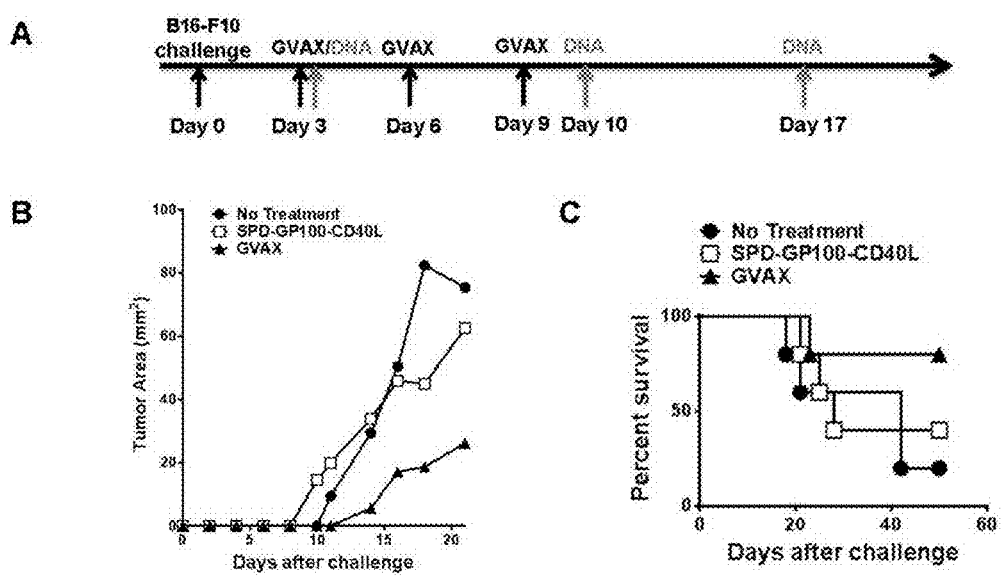
FIG. 15: Immunotherapy of established B16F10 melanoma tumors. Panel A: Immunization schedule for B16-F10 tumor challenge and DNA/GVAX therapeutic vaccination, as indicated by arrows. B16F10 cells (50,000) were injected i.d. into the left flank of C57BL/6 mice on day 0. Mice were then immunized by i.m. injection of PBS or pSPD-gp100-

We next investigated the anti-tumor efficacy of pSPD-gp100-CD40L plasmid, using a B16-F10 melanoma therapeutic vaccination model (FIG. 15). Mice were divided into three vaccination groups: (i) PBS, (ii) pSPD-gp100-CD40L, and (iii) GVAX therapy. Group (ii) received 100 µg of pSPD-gp100-CD40L i.m. per vaccination. We did not observe a statistical difference in tumor sizes and survival between groups (FIGS. 15B and 15C), suggesting that pSPD-gp100-CD40L alone is insufficient to induce an anti-tumor activity.

The Combination of pSPD-Gp100-CD40L, pGM-CSF, and pIL-12p70 Inhibited Tumor Growth and Enhanced Survival Following B16-F10 Tumor Challenge Next, we investigated whether SPD-gp100-CD40L activity could be enhanced using the molecular adjuvants GM-CSF and IL-12p70. We hypothesized that DC chemoattraction induced by GM-CSF and T cell costimulation induced by IL-12p70 would synergize with the CD40L-mediated DC activation induced by SPD-gp100-CD40L, increasing the overall anti-tumor immune response. Mice were divided into 5 vaccination groups: (i) PBS, (ii) pSPD-gp100-CD40L+pGM-CSF, pSPD-gp100-CD40L+pIL-12, (iv) pSPD-gp100-CD40L+pGM-CSF+pIL-12, and (v) GVAX. Empty vector pcDNA3.1 was used as filler to ensure all DNA vaccine groups received the same quantity of total plasmid (120 µg). All DNA vaccinations contained 80 µg of pSPD-gp100-CD40L and 20 µg each of pGM-CSF, pIL-12, and/or pcDNA3.1. The mean tumor size for group (iv) (SPD-gp100-CD40L+GM-CSF+IL-12) was significantly lower compared to groups (i), (ii), and (iii) on days 15, 17, and 20 (FIG. 16B). We observed a statistically significant difference in survival between group (iv) and groups (i), (ii) and (iii) (P<0.05) (FIG. 16C), and a statistically significant difference in tumor-free survival between group (iv) and groups (i), (ii), and (iii) (p<0.01). As shown in FIG. 16D, five out of five mice in group (iv) were free of palpable tumors on day 11 while five out of five mice in groups (i) (ii) and (iii) had palpable tumors on day 11. GVAX "gold standard" vaccination slowed tumor growth compared to untreated animals, however neither tumor growth nor survival reached statistical significance when comparing GVAX to other groups (FIGS. 16B and 16C).

Alternative Combinations of Gp100, SPD-CD40L, IL-12, and GM-CSF Fail to Control of B16-F10 Tumor Growth The previous experiments did not evaluate all possible combinations of gp100, SPD-CD40L, GM-CSF, and IL-12. We therefore wished to confirm that physically linking gp100 and SPD-CD40L was required for activity. Six groups were evaluated: (i) PBS, (ii) pgp100, pgp100+pGM-CSF, (iv) pgp100+pIL-12, (v) pgp100+pGM-CSF+pIL-12, and (vi) pgp100-IRES-SPD-CD40L (gp100 and SPD-CD40L expressed as separate molecules)+pIL-12+pGM-CSF. Empty vector pcDNA3.1 was used as filler to ensure all DNA vaccine groups received the same quantity of plasmid (120 µg total, including 80 µg of the gp100-containing plasmid and 20 µg each of pGM-CSF, pIL-12, and/or pcDNA3.1). We observed no statistical difference in mean tumor sizes between any of the six groups (FIG. 17B). We also failed to observe a statistical difference in survival between groups (FIG. 17C).

Discussion

Recent advances in cancer immunotherapy support the concept that the immune system can induce effective anti-tumor responses. In this context it has been reported that DNA vaccination is effective for the prevention of metastasis and relapse. In particular, the application of DNA vaccination against melanoma has shown promise following the identification of tumor associated antigens (TAA) including gp100, MART-1 and TRP2. For the most part, melanoma DNA therapeutic vaccines are based on the expression of full length antigen following intramuscular injection or electroporation of plasmid DNA. The antigen is secreted from the vaccination site and taken up by APC at the vaccine site or the local draining lymph node. However, it is becoming recognized in the field that targeting cancer antigens directly to APC (in particular dendritic cells) induces a more effective immune response compared to untargeted tumor antigens. We hypothesized that fusing melanoma antigen gp100 within the SPD collagen-like domain of SPD-CD40L multi-trimeric clusters would: 1) target gp100 to DC expressing CD40 in situ, 2) induce cross presentation of gp100 by these DC, possibly via delivery of gp100 to the early endosome, and 3) activate and mature the DC via CD40 crosslinking with CD40L multi-trimers on the DC membrane surface. The SPD-gp100-CD40L fusion protein is a single gene 3.1 kb in size that can be easily encoded within DNA, RNA, or viral vector cancer vaccines. Initially, we determined that SPD-gp100-CD40L was efficiently secreted from transfected cells and formed large multimeric complexes. Western blotting showed that SPD-gp100-CD40L was expressed and secreted into the culture supernatant at the expected molecular weight of 110 kDa. We also confirmed the biological activity of SPD-gp100-CD40L protein using an NF-κB reporter system and DC activation assay. Together these data suggest that SPD-gp100-CD40L is forming a biologically active trimeric CD40L headgroup, in a manner similar to the previously characterized SPD-CD40L protein, and these trimers are forming spontaneous 4-trimer complexes, consistent with the native SPD protein.

In a cancer model, therapeutic immunization with SPD-gp100-CD40L DNA vaccine failed to control tumor growth or improve survival of B16-F10 melanoma (FIG. 16). This is not surprising, given the aggressive nature of established B16-F10 tumor. One possibility is that secretion of immunosuppressive cytokines such as VEGF, IL-10 and TGF-ß by B16-F10 prevents activated cytotoxic T lymphocytes (CTL) induced by SPD-gp100-CD40L from entering into the tumor bed. Alternately, these and other immunosuppressive cytokines suppress cytotoxic activity once the CTL enters the tumor tissue. Previous studies have evaluated cytokines IL-12 and GM-CSF for their ability to enhance T cell mediated immune responses. We hypothesized that SPD-gp100-CD40L combined with cytokines IL-12 and GM-CSF would enhance antigen cross-presentation (via SPD-gp100-CD40L) and immune activation (via GM-CSF and IL-12), overcoming tumor-mediated immune suppression. Consistent with this hypothesis, we observed that vaccination with all 3 genes significantly slowed tumor growth, delayed tumor onset, and improved mouse survival (FIG. 17). Only the triple combination was effective, and all other combinations failed to significantly suppress tumor growth or enhance survival (FIG. 16), including separate expression of gp100 and SPD-CD40L (together with IL-12 and GM-CSF). All animals received the same amount of plasmid (120 µg), allowing us to control for immune stimulation provided by plasmid DNA itself. Based on the literature and our data we propose a model where the effectiveness of SPD-gp100-CD40L is due to the targeting of gp100 to DC, enhanced cross-presentation through CD40-mediated delivery to the early endosome, and the capacity of CD40L multi-trimers to enhance DC activation and maturation. In this model, SPD-gp100-CD40L-mediated DC cross-presentation and activation, coupled with IL-12-p70-mediated T cell stimulation and GM-CSF-mediated chemoattraction of DC, generated an enhanced CD8+ T cell response that was able to overcome immune tolerance at the tumor site. Our results also suggest that CD40L stimulation is a critical component of this vaccine. We did not observe any reduction in tumor growth kinetics when gp100 alone was combined with IL-12 and GM-CSF, despite higher levels of gp100 protein expression in pgp100 transfected cells compared to pSPD-gp100-CD40L transfected cells (FIG. 13C). In addition, the separate delivery of gp100 and SPD-CD40L molecules (using an IRES construct) was unable to replicate the effect of SPD-gp100-CD40L (FIG. 17), consistent with the requirement that gp100 be physically linked to the CD40L multi-trimers for optimal activity. Additional research will be required to determine whether multi-trimerization of CD40L plays a role in the activity of this construct. Of interest, recent studies have shown that delivery of antigen via CD40 can enhance cross presentation to DC. Both enhanced cross-presentation and the simultaneous antigen delivery and DC activation to the same cell may explain the ability of SPD-gp100-CD40L to induce a robust anti-tumor immune response.

In conclusion, this study demonstrates that the fusion of gp100 within SPD-CD40L multi-trimers induces a response against B16-F10 melanoma when combined with IL-12p70 and GM-CSF molecular adjuvants. Overall, SPD-gp100-CD40L is a novel cancer DNA vaccine reagent that provides CD40-mediated APC activation in the context of efficient targeting and cross-presentation of cancer antigen. Future studies will explore alternative SPD-TAA-CD40L fusion proteins using tumor-associated antigens other than gp100. This will allow us to determine whether this strategy can be expanded to a wider range of cancers and TAA. In summary, this study presents a novel reagent for use in cancer therapeutic vaccines, exploiting the unique properties of CD40L on the activation of DC and using CD40L for the targeting and enhanced cross presentation of antigen on APC.

Sequence Examples

The following sequences further describe certain embodiments of the invention:

```
<160>   NUMBER OF SEQ ID NOS: 18

<210>   SEQ ID NO 1

<211>   LENGTH: 2913

<212>   TYPE: DNA

<213>   ORGANISM: Artificial Sequence

<220>   FEATURE:

<223>   OTHER INFORMATION: Murine Surfactant Protein D collagen-like domain
        fused to HIV-1 Gag and the extracellular domain of murine CD40L
``` muSP-D-GAG-muSP-D-muCD40L

Italicized/bolded sequence: Murine SP-D sequence (collagen-like domain)
Non-italicized/bolded sequence: HIV-1 Gag sequence
Italicized sequence: Murine CD40L sequence (extracellular domain)

```
ATGCTGCCCTTTCTCTCCATGCTTGTCTTGCTTGTACAGCCCCTGGGAAATCGGGAGCAGAAAT
GAAGAGCCTCTCGCAGAGATCAGTACCCAACACCTGCACCCTAGTCATGTGTAGCCCAACAGAGA
ATGCCCTGCCTGGTCGTGATGGACGGGATGGGAGAGAAGGTCCACGGGGTGAGAAGGGTGATCCA
GGTTTGCCAGGACCTATGGGGCTCTCAGGGTTGCAGGGCCCTACAGGTCCAGTTGGACCCAAAGG
AGAGAATGGCTCTGCTGGCGAACCTGGACCAAAGGGAGAACGTGGACTAAGTGGAATGGGAGCCA
GGGCCAGCGTGCTGTCTGGGGGCGAGCTGGACAGGTGGGAGAAGATTAGGCTGAGGCCCGGAGGA
AAGAAGAAGTACAAACTGAAACACATCGTGTGGGCCTCCCGGGAGCTGGAACGGTTCGCCGTGAA
TCCTGGGCTGCTGGAGACCTCTGAGGGCTGCAGACAGATCCTGGGACAGCTGCAGCCTAGCCTGC
AGACCGGAAGCGAGGAGCTGAGGTCTCTGTACAACACCGTGGCCACACTGTACTGCGTGCACCAG
CGGATTGAGGTGAAGGATACCAAGGAAGCCCTGGAGAAGATTGAGGAAGAGCAGAATAAGTCCAA
GAAGAAAGCCCAGCAGGCCGCCGCCGACACAGGAAATAGCTCCCAGGTGTCTCAGAACTACCCCA
TCGTGCAGAACCTGCAGGGACAGATGGTGCACCAGGCCATCAGCCCCCGGACCCTGAACGCCTGG
GTGAAGGTGGTGGAAGAGAAAGCCTTCAGCCCAGAAGTGATCCCCATGTTCAGCGCCCTGAGCGA
AGGGGCCACCCCACAGGACCTGAATACAATGCTGAATACAGTGGGCGGCCACCAGGCCGCCATGC
AGATGCTGAAGGAGACCATTAACGAGGAGGCCGCCGAGTGGGATAGGCTGCACCCAGTGCACGCC
GGGCCCATCGCCCCAGGGCAGATGAGGGAGCCACGGGGCTCTGACATCGCCGGCACCACCTCTAC
CCTGCAGGAGCAGATCGGCTGGATGACCAATAACCCACCTATTCCCGTGGGAGAAATCTACAAAA
GGTGGATTATCCTGGGGCTGAACAAGATCGTGAGAATGTACTCCCCAACATCCATTCTGGACATC
CGGCAGGGCCCAAAGGAACCCTTTAGAGACTACGTGGATAGGTTCTACAAAACCCTGCGCGCCGA
```

```
GCAGGCCTCCCAGGAGGTGAAGAACTGGATGACCGAGACACTGCTGGTGCAGAATGCCAACCCAG
ACTGTAAGACCATTCTGAAGGCCCTGGGACCAGCCGCCACCCTGGAGGAAATGATGACAGCCTGC
CAGGGGGTGGGCGGACCCGGCCACAAGGCCCGCGTGCTGGCCGAGGCCATGTCCCAGGTGACAAA
TTCCGCCACCATCATGATGCAGCGCGGAAATTTTCGGAATCAGCGCAAAACAGTGAAATGCTTCA
ATTGCGGGAAGGAGGGCCACATCGCCAAGAATTGCAGAGCCCAAGGAAGAGGGCTGCTGGAAG
TGCCGAAAGGAGGGGCCACCAGATGAAGGACTGCACAGAGCGCCAGGCCAATTTCCTGGGCAAGAT
CTGGCCATCCCACAAGGGGCGGCCTGGAAACTTCCTGCAGAGCCGGCCCGAACCCACAGCCCCCC
CTGAAGAATCCTTCCGGTTCGGAGAGGAAACAACCACACCCAGCCAGAAGCAGGAGCCTATCGAC
AAGGAACTGTACCCACTGGCCAGCCTGAGAAGCCTGTTCGGCAACGATCCAAGCAGCCAGCCTCC
AGGACTTCCAGGTATTCCTGGTCCAGCTGGGAAAGAAGGTCCCTCTGGGAAGCAGGGGAACATAG
GACCTCAAGGCAAACCAGGTCCTAAAGGAGAGGCTGGGCCCAAAGGAGAAGTAGGTGCTCCTGGC
ATGCAAGGATCTACAGGGGCAAAAGGCTCCACAGGCCCCAAGGGAGAAAGAGGTGCCCCTGGTGT
GCAAGGAGCCCCAGGGAATGCTGGAGCAGCAGGACCTGCCGGACCTGCCGGTCCACAGGGAGCTC
CAGGTTCCAGGGGCCCCCAGGACTCAAGGGGGACAGAGGTGTTCCTGGAGACAGAGGAATCAAA
GGTGAAAGCGGGCTTCCAGACAGTGCTGCTCTGAGGCAGCAGATGGAGGCCTTAAAAGGAAAACT
ACAGCGTCTAGAGGTTGCCTTCTCCCACTATCAGAAAGCTGCATTGTTCCCTGATGGCCATAGAA
GATTGGATAAGGTCGAAGAGGAAGTAAACCTTCATGAAGATTTTGTATTCATAAAAAAGCTAAAG
AGATGCAACAAAGGAGAAGGATCTTTATCCTTGCTGAACTGTGAGGAGATGAGAAGGCAATTTGA
AGACCTTGTCAAGGATATAACGTTAAACAAAGAAGAGAAAAAAGAAAACAGCTTTGAAATGCAAA
GAGGTGATGAGGATCCTCAAATTGCAGCACACGTTGTAAGCGAAGCCAACAGTAATGCAGCATCC
GTTCTACAGTGGGCCAAGAAAGGATATTATACCATGAAAAGCAACTTGGTAATGCTTGAAAATGG
GAAACAGCTGACGGTTAAAAGAGAAGGACTCTATTATGTCTACACTCAAGTCACCTTCTGCTCTA
ATCGGGAGCCTTCGAGTCAACGCCCATTCATCGTCGGCCTCTGGCTGAAGCCCAGCATTGGATCT
GAGAGAATCTTACTCAAGGCGGCAAATACCCACAGTTCCTCCCAGCTTTGCGAGCAGCAGTCTGT
TCACTTGGGCGGAGTGTTTGAATTACAAGCTGGTGCTTCTGTGTTTGTCAACGTGACTGAAGCAA
GCCAAGTGATCCACAGAGTTGGCTTCTCATCTTTTGGCTTACTCAAACTCTGA
```

<210> SEQ ID NO 2

<211> LENGTH: 970

<212> TYPE: PRT

<213> ORGANISM: Artificial Sequence

<220> FEATURE:

<223> OTHER INFORMATION: Murine Surfactant Protein D collagen-like domain fused to HIV-1 Gag and the extracellular domain of murine CD40L

```
MLPFLSMLVLLVQPLGNLGAEMKSLSQRSVPNTCTLVMCSPTENGLPGRDGRDGREGPRGEKGDP
GLPGPMGLSGLQGPTGPVGPKGENGSAGEPGPKGERGLSGMGARASVLSGGELDRWEKIRLRPGG
KKKYKLKHIVWASRELERFAVNPGLLETSEGCRQILGQLQPSLQTGSEELRSLYNTVATLYCVHQ
RIEVKDTKEALEKIEEEQNKSKKKAQQAAADTGNSSQVSQNYPIVQNLQGQMVHQAISPRTLNAW
VKVVEEKAFSPEVIPMFSALSEGATPQDLNTMLNTVGGHQAAMQMLKETINEEAAEWDRLHPVHA
GPIAPGQMREPRGSDIAGTTSTLQEQIGWMTNNPPIPVGEIYKRWIILGLNKIVRMYSPTSILDI
RQGPKEPFRDYVDRFYKTLRAEQASQEVKNWMTETLLVQNANPDCKTILKALGPAATLEEMMTAC
QGVGGPGHKARVLAEAMSQVTNSATIMMQRGNFRNQRKTVKCFNCGKEGHIAKNCRAPRKKGCWK
CGKEGHQMKDCTERQANFLGKIWPSHKGRPGNFLQSRPEPTAPPEESFRFGEETTTPSQKQEPID
KELYPLASLRSLFGNDPSSQPPGLPGIPGPAGKEGPSGKQGNIGPQGKPGPKGEAGPKGEVGAPG
MQGSTGAKGSTGPKGERGAPGVQGAPGNAGAAGPAGPAGPQGAPGSRGPPGLKGDRGVPGDRGIK
GESGLPDSAALRQQMEALKGKLQRLEVAFSHYQKAALFPDGHRRLDKVEEEVNLHEDFVFIKKLK
RCNKGEGSLSLLNCEEMRRQFEDLVKDITLNKEEKKENSFEMQRGDEDPQIAAHVVSEANSNAAS
VLQWAKKGYYTMKSNLVMLENGKQLTVKREGLYYVYTQVTFCSNREPSSQRPFIVGLWLKPSIGS
ERILLKAANTHSSSQLCEQQSVHLGGVFELQAGASVFVNVTEASQVIHRVGFSSFGLLKL
``` tpa-muACRP30-gp120-muACRP30-muBAFF

<210> SEQ ID NO 3

<211> LENGTH: 2784

<212> TYPE: DNA

<213> ORGANISM: Artificial Sequence

<220> FEATURE:

<223> OTHER INFORMATION: Human TPA signal sequence fused to murine ACRP30 fused to HIV-1 Env gp120 and the extracellular domain of murine BAFF Underlined sequence: Human TPA sequence
Italicized/bolded sequence: Murine ACRP30 sequence
Non-italicized/bolded sequence: HIV-1 Env gp120 sequence
Italicized sequence: Murine BAFF sequence (extracellular domain)

```
ATGGATGCAATGAAGAGAGGGCTCTGCTGTGTGCTGCTGCTGTGTGGAGCAGTCTTCGTTTCGCC
CAGCGAAGATGACGTTACTACAACTGAAGAGCTAGCTCCTGCTTTGGTCCCTCCACCCAAGGGAA
CTTGTGCAGGTTGGATGGCAGGCATCCCAGGACATCCTGGCCACAATGGCACACCAGGCCGTGAT
GGCTGGGGCAACCTGTGGGTGACCGTGTACTACGGCGTGCCCGTGTGGAAGGAGGCCAAGACCAC
```

```
CCTGTTCTGCGCCAGCGACGCCAAGAGCTACGAGAAGGAGGTGCACAACGTGTGGGCCACCCACG
CCTGCGTGCCCACCGACCCCAACCCCCAGGAGATCGTGCTGGGCAACGTGACCGAGAACTTCAAC
ATGTGGAAGAACGACATGGTGGACCAGATGCACGAGGACATCATCAGCCTGTGGGACCAGAGCCT
GAAGCCCTGCGTGAAGCTGACCCCCCTGTGCGTGACCCTGAACTGCACCGAGGTGAACGTGACCC
GCAACGTGAACAACAGCGTGGTGAACAACACCACCAACGTGAACAACAGCATGAACGGCGACATG
AAGAACTGCAGCTTCAACATCACCACCGAGCTGAAGGACAAGAAGAAGAACGTGTACGCCCTGTT
CTACAAGCTGGACATCGTGAGCCTGAACGAGACCGACGACAGCGAGACCGGCAACAGCAGCAAGT
ACTACCGCCTGATCAACTGCAACACCAGCGCCCTGACCCAGGCCTGCCCCAAGGTGAGCTTCGAC
CCCATCCCCATCCACTACTGCGCCCCCGCCGGCTACGCCATCCTGAAGTGCAACAACAAGACCTT
CAACGGCACCGGCCCCTGCCACAACGTGAGCACCGTGCAGTGCACCCACGGCATCAAGCCCGTGG
TGAGCACCCAGCTGCTGCTGAACGGCAGCCTGGCCGAGGAGGGCATCATCATCCGCAGCGAGAAC
CTGACCAACAACGTCAAGACCATCATCGTGCACCTGAACCGCAGCATCGAGATCGTGTGCGTGCG
CCCCAACAACAACACCCGCCAGAGCATCCGCATCGGCCCCGGCCAGACCTTCTACGCCACCGGCG
ACATCATCCGGCGACATCCGCCAGGCCCACTGCAACATCAGCCGCACCAACTGGACCAAGACCCTG
CGCGAGGTGCGCAACAAGCTGCGCGAGCACTTCCCCAACAAGAACATCACCTTCAAGCCCAGCAG
CGGCGGCGACCTGGAGATCACCACCCACAGCTTCAACTGCCGCGGCGAGTTCTTCTACTGCAACA
CCAGCGGCCTGTTCAGCATCAACTACACCGAGAACAACACCGACGGCACCCCCATCACCCTGCCC
TGCCGCATCCGCCAGATCATCAACATGTGGCAGGAGGTGGGCCGCGCCATGTACGCCCCCCCCAT
CGAGGGCAACATCGCCTGCAAGAGCGACATCACCGGCCTGCTGCTGGTGCGCGACGGCGGCAGCA
CCAACGACAGCACCAACAACAACACCGAGATCTTCCGCCCCGCCGGCGGCGACATGCGCGACAAC
TGGCGCAGCGAGCTGTACAAGTACAAGGTGGTGGAGATCAAGCCCCTGGGCATCGCCCCCACCGA
GGCCAAGCGCCGCGTGGTGGAGCGCGAGAAGCGCGCCGTGGGCATCGGCGCCGTGTTCCTGGGCT
TCCTGGGCGCCGCCGGCAGCACCATGGGCGCCGCCAGCATCACCCTGACCGCCCAGGCCCGCCAG
GTGCTGAGCGGCATCGTGCAGCAGCAGAGCAACCTGCTGCGCGCCATCGAGGCCCAGCAGCACCT
GCTGCAGCTGACCGTGTGGGGCATCAAGCAGCTGCAGACCCGCGTGCTGGCCATCGAGCGCTACC
TGAAGGACCAGCAGCTGCTGAGAGATGGCACTCCTGGAGAGAAGGGAGAGAAAGGAGATGCAGGT
*CTTCTTGGTCCTAAGGTGAGACAGGAGATGTTGGAATGACAGGAGCTGAAGGGCCACGGGGCTT*
***CCCCCGGAACCCCTGCAGGAAAGGAGAGCCTGGA

<220> FEATURE:

<223> OTHER INFORMATION: Murine Surfactant Protein D collagen-like domain
fused to human gp100 and the extracellular domain of murine CD40L Italicized/bolded sequence: Murine SP-D sequence (collagen-like domain)
Non-italicized/bolded sequence: Human gp100 sequence
Italicized sequence: Murine CD40L sequence (extracellular domain)

_ATGCTGCCCTTTCTCTCCATGCTTGTCTTGCTTGTACAGCCCCTGGGAAATCTGGGAGCAGAAAT_
_GAAGAGCCTCTCCGCAGAGATCAGTACCCAACACCTGCACCCTAGTCATGTGTAGCCCAACAGAGA_
_ATGGCCTGCCTGGTCGTGATGGACGGGATGGGAGAGAAGGTCCACGGGGTGAGAAGGGTGATCCA_
_GGTTTGCCAGGACCTATGGGGCTCTCAGGGTTGCAGGGCCCTACAGGTCCAGTTGGACCCAAAGG_
_AGAGAATGGCTCTGCTGGCGAACCTGGACCAAAGGGAGAACGTGGACTAAGTGGA_AAAGTACCCA
GAAACCAGGACTGGCTTGGTGTCTCAAGGCAACTCAGAACCAAAGCCTGGAACAGGCAGCTGTAT
CCAGAGTGGACAGAAGCCCAGAGACTTGACTGCTGGAGAGGTGGTCAAGTGTCCCTCAAGGTCAG
TAATGATGGGCCTACACTGATTGGTGCAAATGCCTCCTTCTCTATTGCCTTGAACTTCCCTGGAA
GCCAAAAGGTATTGCCAGATGGGCAGGTTATCTGGGTCAACAATACCATCATCAATGGGAGCCAG
GTGTGGGGAGGACAGCCAGTGTATCCCCAGGAAACTGACGATGCCTGCATCTTCCCTGATGGTGG
ACCTTGCCCATCTGGCTCTTGGTCTCAGAAGAGAAGCTTTGTTTATGTCTGGAAGACCTGGGGCC
AATACTGGCAAGTTCTAGGGGCCCAGTGTCTGGGCTGAGCATTGGGACAGGCAGGGCAATGCTG
GGCACACACACCATGGAAGTGACTGTCTACCATCGCCGGGGATCCCGGAGCTATGTGCCTCTTGC
TCATTCCAGCTCAGCCTTCACCATTACTGACCAGGTGCCTTTCTCCGTGAGCGTGTCCAGTTGC
GGGCCTTGGATGGAGGGAACAAGCACTTCCTGAGAAATCAGCCTCTGACCTTTGCCCTCCAGCTC
CATGACCCCAGTGGCTATCTGGCTGAAGCTGACCTCTCCTACACCTGGGACTTTGGAGACAGTAG
TGGAACCCTGATCTCTCGGGCACTTGTGGTCACTCATACTTACCTGGAGCCTGGCCCAGTCACTG
CCCAGGTGGTCCTGCAGGCTGCCATTCCTCTCACCTCCTGTGGCTCCTCCCCAGTTCCAGGCACC
ACAGATGGGCACAGGCCAACTGCAGAGGCCCCTAACACCACAGCTGGCCAAGTGCCTACTACAGA
AGTTGTGGGTACTACACCTGGTCAGGCGCCAACTGCAGAGCCCTCTGGAACCACATCTGTGCAGG
TGCCAACCACTGAAGTCATAAGCACTGCACCTGTGCAGATGCCAACTGCAGAGAGCACAGGTATG
ACACCTGAGAAGGTGCCAGTTTCAGAGGTCATGGGTACCACCTTGGCAGAGATGTCAACTCCAGA
GGCTACAGGTATGACACCTGCAGAGGTATCAATTGTGGTGCTTTCTGGAACCACAGCTGCACAGG
TAACAACTACAGAGTGGGTGGAGACCACAGCTAGAGAGCTACCTATCCCTGAGCCTGAAGGTCCA
GATGCCAGCTCAATCATGTCTACGGAAAGTATTACAGGTTCCCTGGGCCCCCTGCTGGATGGTAC
AGCCACCTTAAGGCTGGTGAAGAGACAAGTCCCCCTGGATTGTGTTCTGTATCGATATGGTTCCT
TTTCCGTCACCCTGGACATTGTCCAGGGTATTGAAAGTGCCGAGATCCTGCAGGCTGTGCCGTCC
GGTGAGGGGGATGCATTTGAGCTGACTGTGTCCTGCCAAGGCGGGCTGCCCAAGGAAGCCTGCAT
GGAGATCTCATCGCAGGGTGCCAGCCCCCTGCCCAGCGGCTGTGCCAGCCTGTGCTACCCAGCC
CAGCCTGCCAGCTGGTTCTGCACCAGATACTGAAGGGTGGCTCGGGGACATACTGCCTCAATGTG
TCTCTGGCTGATACCAACAGCCTGGCAGTGGTCAGCACCCAGCTTATCATGCCTGGTCAAGAAGC
AGGCCTTGGGCAGGT*_CCTCCAGGACTTCCAGGTATTCCTGGTCCAGCTGGGAAGAAGGTCCCT_*
*_CTGGGAAGCAGGGGAACATAGGACCTCAAGGCAAACCAGGTCCTAAAGGAGAGGCTGGGCCCAAA_*
*_GGAGAAGTAGGTGCTCCTGGCATGCAAGGATCTACAGGGCCAAAGGCTCCACAGGCCCCAAGGG_*
*_AGAAAGAGGTGCCCCTGGTGTGCAAGGAGCCCCAGGGAATGCTGGAGCAGCAGGACCTGCCGGAC_*
*_CTGCCGGTCCACAGGGAGCTCCAGGTTCCAGGGGGCCCCAGGACTCAAGGGGACAGAGGTGTT_*
*_CCTGGAGACAGAGGAATCAAAGGTGAAAGCGGGCTTCCAGACAGTGCTGCTCTGAGGCAGCAGAT_*
*_GGAGGCCTTAAAAGGAAAACTACAGCGTCTAGAGGTTGCCTTCTCCCAATATCAGAAAGCTGCAT_*
*_TGTTCCCTGATGGC_*CATAGAAGATTGGATAAGGTCGAAGAGGAAGTAAACCTTCATGAAGATTTT
GTATTCATAAAAAAGCTAAAGAGATGCAACAAAGGAGAAGGATCTTTATCCTTGCTGAACTGTGA
GGGAGATGAGAAGGCAATTTGAAGACCTTGTCAAGGATATAACGTTAAACAAGAAGAGAAAAAG
AAAACAGCTTTGAAATGCAAAGAGGTGATGAGGATCCTCAAATTGCAGCACACGTTGTAAGCGAA
GCCAACAGTAATGCAGCATCCGTTCTACAGTGGGCCAAGAAAGATATTATACCATGAAAAGCAA
CTTGGTAATGCTTGAAAATGGGAAACAGCTGACGGTTAAAAGAGAAGGACTCTATTATGTCTACA
CTCAAGTCACCTTCTGCTCTAATCGGGAGCCTTGAGTCAACGCCCATTCATCGTCGGCCTCTGG
CTGAAGCCCAGCATTGGATCTGAGAGAATCTTACTCAAGGCGGCAAATACCCACAGTTCCTCCCA
GCTTTGCGAGCAGCAGTCTGTTCACTTGGGCGGAGTGTTTGAATTACAAGCTGGTGCTTCTGTGT
TTGTCAACGTGACTGAAGCAAGCCAAGTGATCCACAGAGTTGGCTTCTCATCTTTTGGCTTACTC
AAACTCTGA

<210> SEQ ID NO 6

<211> LENGTH: 1042

<212> TYPE: PRT

<213> ORGANISM: Artificial Sequence

<220> FEATURE:

<223> OTHER INFORMATION: Murine Surfactant Protein D collagen-like domain
fused to human gp100 and the extracellular domain of murine CD40L MLPFLSMLVLLVQPLGNLGAEMKSLSQRSVPNTCTLVMCSPTENGLPGRDGRDGREGPRGEKGDP
GLPGPMGLSGLQGPTGPVGPKGENGSAGEPGPKGERGLSGKVPRNQDWLGVSRQLRTKAWNRQLY
PEWTEAQRLDCWRGGQVSLKVSNDGPTLIGANASFSIALNFPGSQKVLPDGQVIWVNNTIINGSQ
VWGGQPVYPQETDDACIFPDGGPCPSGSWSQKRSFVYVWKTWGQYWQVLGGPVSGLSIGTGRAML
GTHTMEVTVYHRRGSRSYVPLAHSSSAFTITDQVPFSVSVSQLRALDGGNKHFLRNQPLTFALQL
HDPSGYLAEADLSYTWDFGDSSGTLISRALVVTHTYLEPGPVTAQVVLQAAIPLTSCGSSPVPGT
TDGHRPTAEAPNTTAGQVPTTEVVGTTPGQAPTAEPSGTTSVQVPTTEVISTAPVQMPTAESTGM
TPEKVPVSEVMGTTLAEMSTPEATGMTPAEVSIVVLSGTTAAQVTTTEWVETTARELPIPEPEGP DASSIMSTESITGSLGPLLDGTATLRLVKRQVPLDCVLYRYGSFSVTLDIVQGIESAEILQAVPS
GEGDAFELTVSCQGGLPKEACMEISSPGCQPPAQRLCQPVLPSPACQLVLHQILKGGSGTYCLNV
SLADTNSLAVVSTQLIMPGQEAGLGQVPPGLPGIPGPAGKEGPSGKQGNIGPQGKPGPKGEAGPK
GEVGAPGMQGSTGAKGSTGPKGERGAPGVQGAPGNAGAAGPAGPAGPQGAPGSRGPPGLKGDRGV
PGDRGIKGESGLPDSAALRQQMEALKGKLQRLEVAFSHYQKAALFPDGHRRLDKVEEEVNLHEDF
VFIKKLKRCNKGEGSLSLLNCEEMRRQFEDLVKDITLNKEEKKENSFEMQRGDEDPQIAAHVVSE
ANSNAASVLQWAKKGYYTMKSNLVMLENGKQLTVKREGLYYVYTQVTFCSNREPSSQRPFIVGLW
LKPSIGSERILLKAANTHSSSQLCEQQSVHLGGVFELQAGASVFVNVTEASQVIHRVGFSSFGLL
KL tpa-huIgG1Fc-gp120-GCN4-huAPRIL

<210>    SEQ ID NO 7

<211>    LENGTH: 3282

<212>    TYPE: DNA

<213>    ORGANISM: Artificial Sequence

<220>    FEATURE:

<223>    OTHER INFORMATION: Human tpa signal sequence fused to human IgG1 Fc
         region fused to HIV-1 Env gp120 fused to GCN4 trimerization motif fused
         to the extracellular domain of human APRIL Underlined sequence: Human tpa signal sequence
Italicized/bolded sequence: Human IgG1 Fc domain to hinge region
Non-italicized/bolded sequence: HIV-1 Env gp120 sequence
Bold sequence: GCN4 trimerization motif
Italicized sequence: Murine APRIL sequence (extracellular domain)

ATGGATGCAATGAAGAGAGGGCTCTGCTGTGTGCTGCTGCTGTGTGGAGCAGTCTTCGTTTCGCC
CAGCTCTTGTGACAAAACTCACACATGCCCACCGTGCCCAGCACCTGAACTCCTGGGGGGACCGT
CAGTCTTCCTCTTCCCCCCAAAACCCAAGGACACCCTCATGATCTCCCGGACCCCTGAGGTCACA
TGCGTGGTGGTGGACGTGAGCCACGAAGACCCTGAGGTCAAGTTCAACTGGTACGTGGACGGCGT
GGAGGTGCATAATGCCAAGACAAAGCCGCGGGAGGAGCAGTACAACAGCACGTACCGTGTGGTCA
GCGTCCTCACCGTCCTGCACCAGGACTGGCTGAATGGCAAGGAGTACAAGTGCAAGGTCTCCAAC
AAAGCCCTCCCAGCCCCCATCGAGAAAACCATCTCCAAAGCCAAAGGGCAGCCCCGAGAACCACA
GGTGTACACCCTGCCCCCATCCCGGGATGAGCTGACCAAGAACCAGGTCAGCCTGACCTGCCTGG
TCAAAGGCTTCTATCCCAGCGACATCGCCGTGGAGTGGGAGAGCAATGGGCAGCCGGAGAACAAC
TACAAGACCACGCCTCCCGTGCTGGACTCCGACGGCTCCTTCTTCCTCTACAGCAAGCTCACCGT
GGACAAGAGCAGGTGGCAGCAGGGGAACGTCTTCTCATGCTCCGTGATGCATGAGGCTCTGCACA
ACCACTACACGCAGAAGAGCCTCTCCCTGTCTCCGGGTAAATGGGGCAACCTGTGGGTGACCGTG
TACTACGGCGTGCCCGTGTGGAAGGAGGCCAAGACCACCCTGTTCTGCGCCAGCGACGCCAAGAG
CTACGAGAAGGAGGTGCACAACGTGTGGGCCACCCACGCCTGCGTGCCCACCGACCCCAACCCCC
AGGAGATCGTGCTGGGCAACGTGACCGAGAACTTCAACATGTGGAAGAACGACATGGTGGACCAG
ATGCACGAGGACATCATCAGCCTGTGGGACCAGAGCCTGAAGCCCTGCGTGAAGCTGACCCCCCT
GTGCGTGACCCTGAACTGCACCGAGGTGAACGTGACCCGCAACGTGAACAACAGCGTGGTGAACA
CACCACCAACGTGAACAACAGCATGAACGGCGACATGAAGAACTGCAGCTTCAACATCACCACC
GAGCTGAAGGACAAGAAGAAGAACGTGTACGCCCTGTTCTACAAGCTGGACATCGTGAGCCTGAA
CGAGACCGACGACAGCGAGACCGGCAACAGCAGCAAGTACTACGCCTGATCAACTGCAACACCA
GCGCCCTGACCCAGGCCTGCCCCAAGGTGAGCTTCGACCCCATCCCCATCCACTACTGCGCCCCC
GCCGGCTACGCCATCCTGAAGTGCAACAACAAGACCTTCAACGGCACCGGCCCCTGCCACAACGT
GAGCACCGTGCAGTGCACCCACGGCATCAAGCCCGTGGTGAGCACCCAGCTGCTGCTGAACGGCA
GCCTGGCCGAGGAGGGCATCATCATCCGCAGCGAGAACCTGACCAACAACGTCAAGACCATCATC
GTGCACCTGAACCGCAGCATCGAGATCGTGTGCGTGCGCCCCAACAACAACACCCGCCAGAGCAT
CCGCATCGGCCCCGGCCAGACCTTCTACGCCACCGGCGACATCATCGGCGACATCCGCCAGGCCC
ACTGCAACATCAGCCGCACCAACTGGACCAAGACCCTGCGCGAGGTGCGCAACAAGCTGCGCGAG
CACTTCCCCAACAAGAACATCACCTTCAAGCCCAGCAGCGGCGGCGACCTGGAGATCACCACCCA
CAGCTTCAACTGCCGCGGCGAGTTCTTCTACTGCAACACCAGCGGCCTGTTCAGCATCAACTACA
CCGAGAACAACACCGACGGCACCCCCATCACCCTGCCCTGCCGCATCCGCCAGATCATCAACATG
TGGCAGGAGGTGGGCCGCGCCATGTACGCCCCCCCCATCGAGGGCAACATCGCCTGCAAGAGCGA
CATCACCGGCCTGCTGCTGGTGCGCGACGGCGGCAGCACCAACGACGAGCACCAACAACAACACCG
AGATCTTCCGCCCCGCCGGCGGCGACATGCGCGACAACTGGCGCAGCGAGCTGTACAAGTACAAG
GTGGTGGAGATCAAGCCCCTGGGCATCGCCCCCACCGAGGCCAAGCGCCGCGTGGTGGAGCGCGA
GAAGCGCGCCGTGGGCATCGGCGCCGTGTTCCTGGGCTTCCTGGGCGCCGCCGGCAGCACCATGG
GCGCCGCCAGCATCACCCTGACCGCCCAGGCCCGCCAGGTGCTGAGCGGCATCGTGCAGCAGCAG
AGCAACCTGCTGCGCGCCATCGAGGCCCAGCAGCACCTGCTGCAGCTGACCGTGTGGGGCATCAA
GCAGCTGCAGACCCGCGTGCTGGCCATCGAGCGCTACCTGAAGGACCAGCAGCTGCT**ATGAAAC
AGATCGAGGATAAGATTGAGGAAATCCTGAGCAAGATCTACCATATCGAGAACGAAATTGCTAGG
ATCAAAAAGCTGATCGGCGAGGTG**ATGCCAGCCTCATCTCCAGGCCACATGGGGGGCTCAGTCAG
AGAGCCAGCCCTTTCGGTTGCTCTTTGGTTGAGTTGGGGGGCAGTTCTGGGGGCTGTGACTTGTG
CTGTCGCACTACTGATCCAACAGACAGAGCTGCAAAGCCTAAGGCGGGAGGTGAGCCGGCTGCAG
CGGAGTGGAGGGCCTTCCCAGAAGCAGGGAGAGCGCCCATGCAGAGCCTCTGGGAGCAGAGTCC
TGATGTCCTGGAAGCCTGGAAGGATGGGGCGAAATCTCGGAGAAGGAGAGCAGTACTCACCCAGA
AGCACAAGAAGAAGCACTCAGTCCTGCATCTTGTTCCAGTTAACATTACCTCCAAGGACTCTGAC
GTGACAGAGGTGATGTGGCAACCAGTACTTAGGCGTGGGAGAGGCCTGGAGGCCCAGGGAGACAT
TGTACGAGTCTGGGACACTGGAATTTATCTGCTCTATAGTCAGGTCCTGTTTCATGATGTGACTT
TCACAATGGGTCAGGTGGTATCTCGGGAAGGACAAGGGAGAAGAGAAACTCTATTCCGATGTATC

```
AGAAGTATGCCTTCTGATCCTGACCGTGCCTACAATAGCTGCTACAGTGCAGGTGTCTTTCATTT
ACATCAAGGGGATATTATCACTGTCAAAATTCCACGGGCAAACGCAAAACTTAGCCTTTCTCCGC
ATGGAACATTCCTGGGGTTTGTGAAACTATGA
```

<210> SEQ ID NO 8

<211> LENGTH: 1093

<212> TYPE: PRT

<213> ORGANISM: Artificial Sequence

<220> FEATURE:

<223> OTHER INFORMATION: Human tpa signal sequence fused to human IgG1 Fc
region fused to HIV-1 Env gp120 fused to GCN4 trimerization motif fused
to the extracellular domain of human APRIL

```
MDAMKRGLCCVLLLCGAVFVSPSSCDKTHTCPPCPAPELLGGPSVFLFPPKPKDTLMISRTPEVT
CVVVDVSHEDPEVKFNWYVDGVEVHNAKTKPREEQYNSTYRVVSVLTVLHQDWLNGKEYKCKVSN
KALPAPIEKTISKAKGQPREPQVYTLPPSRDELTKNQVSLTCLVKGFYPSDIAVEWESNGQPENN
YKTTPPVLDSDGSFFLYSKLTVDKSRWQQGNVFSCSVMHEALHNHYTQKSLSLSPGKWGNLWVTV
YYGVPVWKEAKTTLFCASDAKSYEKEVHNVWATHACVPTDPNPQEIVLGNVTENFNMWKNDMVDQ
MHEDIISLWDQSLKPCVKLTPLCVTLNCTEVNVTRNVNNSVVNNTTNVNNSMNGDMKNCSFNITT
ELKDKKKNVYALFYKLDIVSLNETDDSETGNSSKYYRLINCNTSALTQACPKVSFDPIPIHYCAP
AGYAILKCNNKTFNGTGPCHNVSTVQCTHGIKPVVSTQLLLNGSLAEEGIIIRSENLTNNVKTII
VHLNRSIEIVCVRPNNNTRQSIRIGPGQTFYATGDIIGDIRQAHCNISRTNWTKTLREVRNKLRE
HFPNKNITFKPSSGGDLEITTHSFNCRGEFFYCNTSGLFSINYTENNTDGTPITLPCRIRQIINM
WQEVGRAMYAPPIEGNIACKSDITGLLLVRDGGSTNDSTNNNTEIFRPAGGDMRDNWRSELYKYK
VVEIKPLGIAPTEAKRRVVEREKRAVGIGAVFLGFLGAAGSTMGAASITLTAQARQVLSGIVQQQ
SNLLRAIEAQQHLLQLTVWGIKQLQTRVLAIERYLKDQQLLMKQIEDKIEEILSKIYHIENEIAR
IKKLIGEVMPASSPGHMGGSVREPALSVALWLSWGAVLGAVTCAVALLIQQTELQSLRREVSRLQ
RSGGPSQKQGERPWQSLWEQSPDVLEAWKDGAKSRRRRAVLTQKHKKKHSVLHLVPVNITSKDSD
VTEVMWQPVLRRGRGLEAQGDIVRVWDTGIYLLYSQVLFHDVTFTMGQVVSREGQGRRETLFRCI
RSMPSDPDRAYNSCYSAGVFHLHQGDIITVKIPRANAKLSLSPHGTFLGFVKL
``` huSP-D-NP-huSP-D-huCD40L-NST

<210> SEQ ID NO 9

<211> LENGTH: 2769

<212> TYPE: DNA

<213> ORGANISM: Artificial Sequence

<220> FEATURE:

<223> OTHER INFORMATION: Human Surfactant Protein D collagen-like domain fused
to H. influenza NP protein and the extracellular domain of human CD40L
(minus stalk region (Non-Stalk (NST)))

Italicized/bolded sequence: Human SP-D sequence (collagen-like domain)
Non-italicized/bolded sequence: H. influenza NP sequence
Italicized sequence: Human CD40L sequence (extracellular domain, missing stalk
region)

```
ATGCTGCTCTTCCTCCTCTCTGCACTGGTCCTACTCACACAGCCCCTGGGCTACCTGGAAGCAGA
AATGAAGACCTACTCCCACAGAACAACGCCCAGTGCTTGCACCCTGGTCATGTGTAGCTCAGTGG
AGAGTGGCCTGCCTGGTCGCGATGGACGGGATGGAGAGAGGCCCTCGGGCGAGAAGGGGGAC
CCAGGTTTGCCAGGAGCTGCAGGGCAAGCAGGGATGCCTGGACAAGCTGGCCCAGTTGGGCCCAA
AGGGGACAATGGCTCTGTTGGAGAACCTGGACCAAAGGGAGACACTGGGCCAAGTATGGCGTCTC
AAGGCACCAAACGATCTTACGAACAGATGGAGACTGATGGAGAACGCCAGAATGCCACTGAAATC
AGAGCATCCGTCGGAAAAATGATTGGTGGAATTGGACGATTCTACATCCAAATGTGCACCGAACT
CAAACTCAGTGATTATGAGGGACGGTTGATCCAAAACAGCTTAACAATAGAGAATGGTGCTCT
CTGCTTTTGACGAAAGGAGAAATAAATACCTTGAAGAACATCCCAGTGCGGGAAAAGATCCTAAG
AAAACTGGAGGACCTATATACAGGAGAGTAAACGGAAAGTGGATGAGAGAACTCATCCTTTATGA
CAAAGAAGAAATAAGGCGAATCTGGCGCCAAGCTAATAATGGTGACGATGCAACGGCTGGTCTGA
CTCACATGATGATCTGGCATTCCAATTTGAATGATGCAACTTATCAGAGGACAAGAGCTCTTGTT
CGCACCGGAATGGATCCCAGGATGTGCTCTCTGATGCAAGGTTCAACTCTCCCTAGGAGGTCTGG
AGCCGCAGGTGCTGCAGTCAAAGGAGTTGGAACAATGGTGATGGAATTGGTCAGAATGATCAAAC
GTGGGATCAATGATCGGAACTTCTGGAGGGGTGAGAATGGACGAAAAACAAGAATTGCTTATGAA
AGAATGCAACATTCTCAAAGGGAAATTTCAAACTGCTGCACAAAAAGCAATGATGGATCAAGT
GAGAGAGAGCCGGAACCCAGGGAATGCTGAGTTCGAAGATCTCACTTTTCTAGCACGGTCTGCAC
TCATATTGAGAGGGTCGGTTGCTCACAAGTCCTGCCTGCCTGCCTGTGTGTATGGGCCTGCCGTA
GCCAGTGGGTACGACTTTGAAAGGGAGGGATACTCTCTAGTCGGAATAGACCCTTTCAGACTGCT
TCAAAACAGCCAAGTGTACAGCCTAATCGACCAAATGAGAATCCAGCACACAAGAGTCAACTGG
TGTGGATGGCATGCCATTCTGCCGCATTTGAAGATCTAAGAGTATTAAGCTTCATCAAAGGGACG
AAGGTGCTCCCAAGAGGGAAGCTTTCCACTAGAGGAGTTCAAATTGCTTCCAATGAAAATATGGA
GACTATGGAATCAAGTACACTTGAACTGAGAAGCAGGTACTGGGCCATAAGGACCAGAAGTGGAG
```

-continued

```
GAAACACCAATCAACAGAGGGCATCTGCGGGCCAAATCAGCATACAACCTACGTTCTCAGTACAG
AGAAATCTCCCTTTTGACAGAACAACCATTATGGCAGCATTCAATGGGAATACAGAGGGGAGAAC
ATCTGACATGAGGACCGAAATCATAAGGATGATGGAAAGTGCAAGACCAGAAGATGTGTCTTTCC
AGGGGCGGGGAGTCTTCGAGCTCTCGGACGAAAAGGCAGCGAGCCCGATCGTGCCTTCCTTTGAC
ATGAGTAATGAAGGATCTTATTTCTTCGGAGACAATGCAGAGGAGTACGACAATGGACCTCCAGG
ACCTCCCGGTGTGCCTGGTCCAGCTGGAAGAGAAGGTCCCCTGGGGAAGCAGGGGAACATAGGAC
CTCAGGGCAAGCCAGGCCCAAAAGGAGAAGCTGGGCCCAAAGGAGAAGTAGGTGCCCCAGGCATG
CAGGGCTCGGCAGGGGCAAGAGGCCTCGCAGGCCCTAAGGGAGAGCGAGGTGTCCCTGGTGAGCG
TGGAGTCCCTGGAAACACAGGGGCAGCAGGGTCTGCTGGAGCCATGGGTCCCCAGGGAAGTCCAG
GTGCCAGGGGACCCCCGGGATTGAAGGGGACAAAGGCATTCCTGGAGACAAAGGAGCAAAGGGA
GAAAGTGGGCTTCCAGATGTTGCTTCTCTGAGGCAGCAGGTTGAGGCCTTACAGGGACAAGTACA
GCACCTCCAGGCTGCTTTCTCTCAGTATAAGAAAGTTGAGCTCTTCCCAAATGGCAAAGTGTCG
GGGAGAAGATTTTCAAGCAGCAGGCTTTGTAAAACCATTTACGGAGGCACAGGGTGATCGAAT
CCTCAAATTGCGGCACATGTCATAAGTGAGGCCAGCAGTAAAACAACATCTGTGTTACAGTGGGC
TGAAAAAGGATACTACACCATGAGCAACAACTTGGTAACCCTGGAAAATGGGAAACAGCTGACCG
TTAAAAGACAAGGACTCTATTATATCTATGCCCAAGTCACCTTCTGTTCCAATCGGGAAGCTTCG
AGTCAAGCTCCATTTATAGCCAGCCTCTGCCTAAAGTCCCCCGGTAGATTCGAGAGAATCTTACT
CAGAGCTGCAAATACCCACAGTTCCGCCAAACCTTGCGGGCAACAATCCATTCACTTGGGAGGAG
TATTTGAATTGCAACCAGGTGCTTCGGTGTTTGTCAATGTGACTGATCCAAGCCAAGTGAGCCAT
GGCACTGGCTTCACGTCCTTTGGCTTACTCAAACTCTGA
```

<210> SEQ ID NO 10

<211> LENGTH: 922

<212> TYPE: PRT

<213> ORGANISM: Artificial Sequence

<220> FEATURE:

<223> OTHER INFORMATION: Human Surfactant Protein D collagen-like domain fused to H. influenza NP protein and the extracellular domain of human CD40L (minus stalk region (Non-Stalk (NST)))

```
MLLFLLSALVLLTQPLGYLEAEMKTYSHRTTPSACTLVMCSSVESGLPGRDGRDGREGPRGEKGD
PGLPGAAGQAGMPGQAGPVGPKGDNGSVGEPGPKGDTGPSMASQGTKRSYEQMETDGERQNATEI
RASVGKMIGGIGRFYIQMCTELKLSDYEGRLIQNSLTIERMVLSAFDERRNKYLEEHPSAGKDPK
KTGGPIYRRVNGKWMRELILYDKEEIRRIWRQANNGDDATAGLTHMMIWHSNLNDATYQRTRALV
RTGMDPRMCSLMQGSTLPRRSGAAGAAVKGVGTMVMELVRMIKRGINDRNFWRGENGRKTRIAYE
RMCNILKGKFQTAAQKAMMDQVRESRNPGNAEFEDLTFLARSALILRGSVAHKSCLPACVYGPAV
ASGYDFEREGYSLVGIDPFRLLQNSQVYSLIRPNENPAHKSQLVWMACHSAAFEDLRVLSFIKGT
KVLPRGKLSTRGVQIASNENMETMESSTLELRSRYWAIRTRSGGNTNQQRASAGQISIQPTFSVQ
RNLPFDRTTIMAAFNGNTEGRTSDMRTEIIRMMESARPEDVSFQGRGVFELSDEKAASPIVPSFD
MSNEGSYFFGDNAEEYDNGPPGPPGVPGPAGREGPLGKQGNIGPQGKPGPKGEAGPKGEVGAPGM
QGSAGARGLAGPKGERGVPGERGVPGNTGAAGSAGAMGPQGSPGARGPPGLKGDKGIPGDKGAKG
ESGLPDVASLRQQVEALQGQVQHLQAAFSQYKKVELFPNGQSVGEKIFKTAGFVKPFTEAQGDQN
PQIAAHVISEASSKTTSVLQWAEKGYYTMSNNLVTLENGKQLTVKRQGLYYIYAQVTFCSNREAS
SQAPFIASLCLKSPGRFERILLRAANTHSSAKPCGQQSIHLGGVFELQPGASVFVNVTDPSQVSH
GTGFTSFGLLKL
``` tpa-muACRP30-CSP1-muACRP30-muCD40L

<210> SEQ ID NO 11

<211> LENGTH: 1929

<212> TYPE: DNA

<213> ORGANISM: Artificial Sequence

<220> FEATURE:

<223> OTHER INFORMATION: Human TPA signal sequence fused to murine ACRP30 fused to P. yoelii CSP-1 and the extracellular domain of murine CD40L Underlined sequence: Human TPA sequence
Italicized/bolded sequence: Murine ACRP30 sequence
Non-italicized/bolded sequence: P. yoelii CSP-1 sequence
Italicized sequence: Murine CD40L sequence (extracellular domain)

```
ATGGATGCAATGAAGAGAGGGCTCTGCTGTGTGCTGCTGCTGTGTGGAGCAGTCTTCGTTTCGCC
CAGCGAAGATGACGTTACTACAACTGAAGAGCTAGCTCCTGCTTTGGTCCCTCCACCCAAGGGAA
CTTGTGCAGGTTGGATGGCAGGCATCCCAGGACATCCTGGCCACAATGGCACACCAGGCCGTGAT
GGCAAAATATACAATCGAAATATAGTCAACAGATTACTTGGCGATGCTCTCAACGGAAAACCAGA
AGAAAAAAAGATGATCCCCCAAAAGATGGCAACAAAGATGATCTTCCAAAAGAAGAAAAAAAG
ATGATCTTCCAAAAGAAGAAAAAAAGATGATCCCCCAAAAGATCCTAAAAAAGATGATCCACCA
AAAGAGGCTCAAAATAAATTGAATCAACCAGTAGTGGCAGATGAAATGTAGATCAAGGGCCAGG
AGCACCACAAGGGCCAGGAGCACCACAAGGACCAGGAGCACCACAGGGTCCAGGAGCACCACAAG
```

-continued

```
GACCAGGAGCACCACAAGGACCAGGAGCACCACAAGGTCCAGGAGCACCACAGGGTCCAGGAGCA
CCACAGGGTCCAGGAGCACCACAAGGACCAGGAGCACCACAGGGGCCAGGAGCACCACAAGGACC
AGGAGCACCACAAGGACCAGGAGCACCACAGGGGCCAGGAGCACCACAAGGGCCAGGAGCACCAC
AAGAACCACCCCAACAACCACCCCAACAACCACCACAACAGCCACCACAACAGCCACCACAACAG
CCACCACAACAGCCACCACAACAACCACGCCCACAGCCAGATGGTAATAACAACAATAACAATAA
TAATGGTAATAATAATGAAGATTCTTATGTCCCAAGCGCGGAACAAATACTAGAATTTGTTAAAC
AGATAAGTAGTCAACTCACAGAGGAATGGTCTCAATGTAGTGTAACCTGTGGTTCTGGTGTAAGA
GTTAGAAAACGAAAAAATGTAAACAAGCAACCAGAAAATTTGACCTTAGAGGATATTGATACTGA
AATTTGTAAAATGGATAAATGTTCAAGTATATTTAATATTGTAAGCAATTCATTAGGATTTGTAA
TATTATTAGTATTAGTATTCTTTAATAGAGATGGCACTCCTGGAGAGAAGGGAGAGAAAGGAGAT
GCAGGTCTTCTTGGTCCTAAGGGTGAGACAGGAGATGTTGGAATGACAGGAGCTGAAGGGCCACG
GGGCTTCCCCGGAACCCCTGGCAGGAAAGGAGAGCCTGGAGAAGCCGCTCATAGAAGATTGGATA
AGGTCGAAGAGGAAGTAAACCTTCATGAAGATTTTGTATTCATAAAAAAGCTAAAGAGATGCAAC
AAAGGAGAAGGATCTTTATCCTTGCTGAACTGTGAGGAGATGAGAAGGCAATTTGAAGACCTTGT
CAAGGATATAACGTTAAACAAAGAAGAGAAAAAAGAAAACAGCTTTGAAATGCAAAGAGGTGATG
AGGATCCTCAAATTGCAGCACACGTTGTAAGCGAAGCCAACAGTAATGCAGCATCCGTTCTACAG
TGGGCCAAGAAAGGATATTATACCATGAAAAGCAACTTGGTAATGCTTGAAAATGGGAAACAGCT
GACGGTTAAAAGAGAAGGACTCTATTATGTCTACACTCAAGTCACCTTCTGCTCTAATCGGGAGC
CTTCGAGTCAACGCCCATTCATCGTCGGCCTCTGGCTGAAGCCCAGCATTGGATCTGAGAGAATC
TTACTCAAGGCGGCAAATACCCACAGTTCCTCCCAGCTTTGCGAGCAGCAGTCTGTTCACTTGGG
CGGAGTGTTTGAATTACAAGCTGGTGCTTCTGTGTTTGTCAACGTGACTGAAGCAAGCCAAGTGA
TCCACAGAGTTGGCTTCTCATCTTTTGGCTTACTCAAACTCTGA
```

<210> SEQ ID NO 12

<211> LENGTH: 642

<212> TYPE: PRT

<213> ORGANISM: Artificial Sequence

<220> FEATURE:

<223> OTHER INFORMATION: Human TPA signal sequence fused to murine ACRP30 fused to P. yoelii CSP-1 and the extracellular domain of murine CD40L

```
MDAMKRGLCCVLLLCGAVFVSPSEDDVTTTEELAPALVPPPKGTCAGWMAGIPGHPGHNGTPGRD
GKIYNRNIVNRLLGDALNGKPEEKKDDPPKDGNKDDLPKEEKKDDLPKEEKKDDPPKDPKKDDPP
KEAQNKLNQPVVADENVDQGPGAPQGPGAPQGPGAPQGPGAPQGPGAPQGPGAPQGPGAPQGPGA
PQGPGAPQGPGAPQGPGAPQGPGAPQGPGAPQGPGAPQGPGAPQEPPQQPPQQPPQQPPQQPPQQ
PPQQPPQQPRPQPDGNNNNNNNNGNNNEDSYVPSAEQILEFVKQISSQLTEEWSQCSVTCGSGVR
VRKRKNVNKQPENLTLEDIDTEICKMDKCSSIFNIVSNSLGFVILLVLVFFNRDGTPGEKGEKGD
AGLLGPKGETGDVGMTGAEGPRGFPGTPGRKGEPGEAAHRRLDKVEEEVNLHEDFVIKKLKRCN
KGEGSLSLLNCEEMRRQFEDLVKDITLNKEEKKENSFEMQRGDEDPQIAAHVVSEANSNAASVLQ
WAKKGYYTMKSNLVMLENGKQLTVKREGLYYVYTQVTFCSNREPSSQRPFIVGLWLKPSIGSERI
LLKAANTHSSSQLCEQQSVHLGGVFELQAGASVFVNVTEASQVIHRVGFSSFGLLKL
``` muSP-D-Gag-muSP-D-muRANKL

<210> SEQ ID NO 13

<211> LENGTH: 3006

<212> TYPE: DNA

<213> ORGANISM: Artificial Sequence

<220> FEATURE:

<223> OTHER INFORMATION: Murine Surfactant Protein D collagen-like domain fused to HIV-1 Gag and the extracellular domain of murine RANKL Italicized/bolded sequence: Murine SP-D sequence (collagen-like domain)
Non-italicized/bolded sequence: HIV-1 Gag sequence (shifted 10 aa along SP-D)
Italicized sequence: Murine RANKL sequence (extracellular domain)

```
ATGCTGCCCTTTCTCTCCATGCTTGTCTTGCTTGTACAGCCCCTGGGAAATCTGGGAGCAGAAAT
GAAGAGCCTCTCGCAGAGATCAGTACCCAACACCTGCACCCTAGTCATGTGTAGCCCAACAGAGA
ATGGCCTGCCTGGTCGTGATGGACGGGATGGGAGAGAAGGTCCACGGGGTGAGAAGGGTGATCCA
GGTTTGCCAGGACCTATGGGGCTCTCAGGGTTGCAGGGCCCTACAGGTCCAGTTGGACCCAAAGG
AGAGAATGGCTCTGCTGGCGAACCTGGACCAAAGGGAGAACGTGGACTAAGTGGACCTCCAGGAC
TTCCAGGTATTCCTGGTCCAATGGGAGCCAGGGCCAGCGTGCTGTCTGGGGCGAGCTGGACAGG
TGGGAGAAGATTAGGCTGAGGCCCGGAGGAAAGAAGAAGTACAAACTGAAACACATCGTGTGGGC
CTCCCGGGAGCTGGAACGGTTCGCCGTGAATCCTGGGCTGCTGGAGACCTCTGAGGGCTGCAGAC
AGATCCTGGGACAGCTGCAGCCTAGCCTGCAGACCGGAAGCGAGGAGCTGAGGTCTCTGTACAAC
ACCGTGGCCACACTGTACTGCGTGCACCAGCGGATTGAGGTGAAGGATACCAAGGAAGCCCTGGA
GAAGATTGAGGAAGAGCAGAATAAGTCCAAGAAGAAAGCCCAGCAGGCCGCCGCCGACACAGGAA
ATAGCTCCCAGGTGTCTCAGAACTACCCCATCGTGCAGAACCTGCAGGGACAGATGGTGCACCAG
GCCATCAGCCCCCGGACCCTGAACGCCTGGGTGAAGGTGGTGGAAGAGAAAGCCTTCAGCCCAGA
AGTGATCCCCATGTTCAGCGCCCTGAGCGAAGGGGCCACCCCACAGGACCTGAATACAATGCTGA
```

```
ATACAGTGGGCGGCCACCAGGCCGCCATGCAGATGCTGAAGGAGACCATTAACGAGGAGGCCGCC
GAGTGGGATAGGCTGCACCCAGTGCACGCCGGGCCCATCGCCCCAGGGCAGATGAGGGAGCCACG
GGGCTCTGACATCGCCGGCACCACCTCTACCCTGCAGGAGCAGATCGGCTGGATGACCAATAACC
CACCTATTCCCGTGGGAGAAATCTACAAAAGGTGGATTATCCTGGGGCTGAACAAGATCGTGAGA
ATGTACTCCCCAACATCCATTCTGGACATCCGGCAGGGCCCAAAGGAACCCTTTAGAGACTACGT
GGATAGGTTCTACAAAACCCTGCGCGCCGAGCAGGCCTCCCAGGAGGTGAAGAACTGGATGACCG
AGACACTGCTGGTGCAGAATGCCAACCCAGACTGTAAGACCATTCTGAAGGCCCTGGGACCAGCC
GCCACCCTGGAGGAAATGATGACAGCCTGCCAGGGGGTGGGCGGACCCGGCCACAAGGCCCGCGT
GCTGGCCGAGGCCATGTCCCAGGTGACAAATTCCGCCACCATCATGATGCAGCGCGGAAATTTTC
GGAATCAGCGCAAAACAGTGAAATGCTTCAATTGCGGGAAGGAGGGCCACATCGCCAAGAATTGC
AGAGCCCCAAGGAAGAGGGCTGCTGGAAGTGCGGAAAGGAGGGCCACCAGATGAAGGACTGCAC
AGAGCGCCAGGCCAATTTCCTGGGCAAGATCTGGCCATCCCACAAGGGGCGGCCTGGAAACTTCC
TGCAGAGCCGGCCCGAACCCACAGCCCCCCCTGAAGAATCCTTCCGGTTCGGAGAGGAAACAACC
ACACCCAGCCAGAAGCAGGAGCCTATCGACAAGGAACTGTACCCACTGGCCAGCCTGAGAAGCCT
GTTCGGCAACGATCCAAGCAGCCAG**GCTGGGAAAGAAGGTCCCTCTGGGAAGCAGGGGAACATAG
GACCTCAAGGCAAACCAGGTCCTAAAGGAGAGGCTGGGCCCAAAGGAGAAGTAGGTGCTCCTGGC
ATGCAAGGATCTACAGGGGCAAAAGGCTCCACAGGCCCCAAGGGAGAAAGAGGTGCCCCTGGTGT
GCAAGGAGCCCCAGGGAATGCTGGAGCAGCAGGACCTGCCGGACCTGCCGGTCCACAGGGAGCTC
CAGGTTCCAGGGGGCCCCAGGACTCAAGGGGGACAGAGGTGTTCCTGGAGACAGAGGAATCAAA
GGTGAAAGCGGGCTTCCAGACAGTGCTGCTCTGAGGCAGCAGATGGAGGCCTTAAAAGGAAAACT
ACAGCGTCTAGAGGTTGCCTTCTCCCACTATCAGAAAGCTGCATTGTTCCCTGATGGC**CGAGCGC
AGATGGATCCTAACAGAATATCAGAAGACAGCACTCACTGCTTTTATAGAATCCTGAGACTCCAT
GAAAACGCAGATTTGCAGGACTCGACTCTGGAGAGTGAAGACACACTACCTGACTCCTGCAGGAG
GATGAAACAAGCCTTTCAGGGGGCCGTGCAGAAGGAACTGCAACATTTGTGGGGCCACAGCGCT
TCTCAGGAGCTCCAGCTATGATGGAAGGCTCATGGTTGGATGTGGCCCAGCGAGGCAAGCCTGAG
GCCCAGCCATTTGCACACCTCACCATCAATGCTGCCAGCATCCCATCGGGTTCCCATAAAGTCAC
TCTGTCCTCTTGGTACCACGATCGAGGCTGGGCCAAGATCTCTAACATGACGTTAAGCAACGGAA
AACTAAGGGTTAACCAAGATGGCTTCTATTACCTGTACGCCAACATTTGCTTTCGGCATCATGAA
ACATCGGGAAGCGTACCTACAGACTATCTTCAGCTGATGGTGTATGTCGTTAAAACCAGCATCAA
AATCCCAAGTTCTCATAACCTGATGAAGGAGGGAGCACGAAAAACTGGTCGGGCAATTCTGAAT
TCCACTTTTATTCCATAAATGTTGGGGGATTTTTCAAGCTCCGAGCTGGTGAAGAAATTAGCATT
CAGGTGTCCAACCCTTCCCTGCTGGATCCGGATCAAGATGCGACGTACTTTGGGGCTTTCAAAGT
TCAGGACATAGACTGA
```

<210> SEQ ID NO 14

<211> LENGTH: 1001

<212> TYPE: PRT

<213> ORGANISM: Artificial Sequence

<220> FEATURE:

<223> OTHER INFORMATION: Murine Surfactant Protein D collagen-like domain fused to HIV-1 Gag and the extracellular domain of murine RANKL

```
MLPFLSMLVLLVQP

Italicized/bolded sequence: Human SP-D sequence (collagen-like domain)
Non-italicized/bolded sequence: Human WT1 sequence
Italicized sequence: Human CD40L sequence (extracellular domain)
*ATGCTGCTCTTCCTCCTCTCTGCACTGGTCCTACTCACACAGCCCCTGGGCTACCTGGAAGCAGA*
*AATGAAGACCTACTCCCACAGAACAACGCCCAGTGCTTGCACCCTGGTCATGTGTAGCTCAGTGG*
*AGAGTGGCCTGCCTGGTCGCGATGGACGGGATGGGAGAGAGGGCCCTCGGGGCGAGAAGGGGGAC*
*CCAGGTTTGCCAGGAGCTGCAGGGCAAGCAGGGATGCCTGGACAAGCTGGCCCAGTTGGGCCCAA*
*AGGGGACAATGGCTCTGTTGGAGAACCTGGACCAAAGGGAGACACTGGGCCAAGT*ATGGGCCATC
ATCATCATCATCATCATCATCATCACAGCAGCGGCCATATCGAAGGTCGTCATATGCGACGTGTG
CCTGGAGTAGCCCCGACTCTTGTACGGTCGGCATCTGAGACCAGTGAGAAACGCCCCTTCATGTG
TGCTTACCCAGGCTGCAATAAGAGATATTTTAAGCTGTCCCACTTACAGATGCACAGCAGGAAGC
ACACTGGTGAGAAACCATACCAGTGTGACTTCAAGGACTGTGAACGAAGGTTTTTTCGTTCAGAC
CAGCTCAAAAGACACCAAAGGAGACATACAGGTGTGAAACCATTCCAGTGTAAAACTTGTCAGCG
AAAGTTCTCCCGGTCCGACCACCTGAAGACCCACACCAGGACTCATACAGGTGAAAAGCCCTTCA
GCTGTCGGTGGCCAAGTTGTCAGAAAAAGTTTGCCCGGTCAGATGAATTAGTCCGCCATCACAAC
ATGCATCAGAGAAACATGACCAAACTCCAGCTGGCGCTT*GGACCTCCAGGACCTCCCGGTGTGCC*
*TGGTCCAGCTGGAAGAGAAGGTCCCCTGGGGAAGCAGGGGAACATAGGACCTCAGGGCAAGCCAG*
*GCCCAAAAGGAGAAGCTGGGCCCAAAGGAGAAGTAGGTGCCCCAGGCATGCAGGGCTCGGCAGGG*
*GCAAGAGGCCTCGCAGGCCCTAAGGGAGAGCGAGGTGTCCCTGGTGAGCGTGGAGTCCCTGGAAA*
*CACAGGGGCAGCAGGGTCTGCTGGAGCCATGGGTCCCCAGGGAAGTCCAGGTGCCAGGGGACCCC*
*CGGGATTGAAGGGGGACAAAGGCATTCCTGGAGACAAAGGAGCAAAGGGAGAAAGTGGGCTTCCA*
*GATGTTGCTTCTCTGAGGCAGCAGGTTGAGGCCTTACAGGGACAAGTACAGCACCTCCAGGCTGC*
*TTTCTCTCAGTATAAGAAAGTTGAGCTCTTCCCAAATGGCCAAAGTGTCGGGGAGAAGATTTTCA*
*AGACAGCAGGCTTTGTAAAACCATTTACGGAGGCACAG**CATAGAAGGTTGGACAAGATAGAAGAT*
*GAAAGGAATCTTCATGAAGATTTTGTATTCATGAAAACGATACAGAGATGCAACACAGGAGAAAG*
*ATCCTTATCCTTACTGAACTGTGAGGAGATTAAAAGCCAGTTTGAAGGCTTTGTGAAGGATATAA*
*TGTTAAACAAAGAGGAGACGAAGAAAGAAAACAGCTTTGAAATGCAAAAAGGTGATCAGAATCCT*
*CAAATTGCGGCACATGTCATAAGTGAGGCCAGCAGTAAAACAACATCTGTGTTACAGTGGGCTGA*
*AAAAGGATACTACACCATGAGCAACAACTTGGTAACCCTGGAAAATGGGAAACAGCTGACCGTTA*
*AAAGACAAGGACTCTATTATATCTATGCCCAAGTCACCTTCTGTTCCAATCGGGAAGCTTCGAGT*
*CAAGCTCCATTTATAGCCAGCCTCTGCCTAAAGTCCCCCGGTAGATTCGAGAGAATCTTACTCAG*
*AGCTGCAAATACCCACAGTTCCGCCAAACCTTGCGGGCAACAATCCATTCACTTGGGAGGAGTAT*
*TTGAATTGCAACCAGGTGCTTCGGTGTTTGTCAATGTGACTGATCCAAGCCAAGTGAGCCATGGC*
*ACTGGCTTCACGTCCTTTGGCTTACTCAAACTCTGA*

<210> SEQ ID NO 16

<211> LENGTH: 661

<212> TYPE: PRT

<213> ORGANISM: Artificial Sequence

<220> FEATURE:

<223> OTHER INFORMATION: Human Surfactant Protein D collagen-like domain fused to human WT1 and the extracellular domain of human CD40L MLLFLLSALVLLTQPLGYLEAEMKTYSHRTTPSACTLVMCSSVESGLPGRDGRDGREGPRGEKGD
PGLPGAAGQAGMPGQAGPVGPKGDNGSVGEPGPKGDTGPSMGHHHHHHHHHHSSGHIEGRHMRRV
PGVAPTLVRSASETSEKRPFMCAYPGCNKRYFKLSHLQMHSRKHTGEKPYQCDFKDCERRFFRSD
QLKRHQRRHTGVKPFQCKTCQRKFSRSDHLKTHTRTHTGEKPFSCRWPSCQKKFARSDELVRHHN
MHQRNMTKLQLALGPPGPPGVPGPAGREGPLGKQGNIGPQGKPGPKGEAGPKGEVGAPGMQGSAG
ARGLAGPKGERGVPGERGVPGNTGAAGSAGAMGPQGSPGARGPPGLKGDKGIPGDKGAKGESGLP
DVASLRQQVEALQGQVQHLQAAFSQYKKVELFPNGQSVGEKIFKTAGFVKPFTEAQHRRLDKIED
ERNLHEDFVFMKTIQRCNTGERSLSLLNCEEIKSQFEGFVKDIMLNKEETKKENSFEMQKGDQNP
QIAAHVISEASSKTTSVLQWAEKGYYTMSNNLVTLENGKQLTVKRQGLYYIYAQVTFCSNREASS
QAPFIASLCLKSPGRFERILLRAANTHSSAKPCGQQSIHLGGVFELQPGASVFVNVTDPSQVSHG
TGFTSFGLLKL muSP-D-MAGE-A3-muSP-D-muBAFF

<210> SEQ ID NO 17

<211> LENGTH: 2394

<212> TYPE: DNA

<213> ORGANISM: Artificial Sequence

<220> FEATURE:

<223> OTHER INFORMATION: Murine Surfactant Protein D collagen-like domain fused to murine MAGE-A3 and the extracellular domain of murine BAFF. Deleted 20 aa of SP-D sequence.

Italicized/bolded sequence: Murine SP-D sequence (collagen-like domain) (deleted 20 aa) Non-italicized/bolded sequence: Murine MAGE-A3 sequence Italicized sequence: Murine BAFF sequence (extracellular domain)
*ATGCTGCCCTTTCTCTCCATGCTTGTCTTGCTTGTACAGCCCCTGGGAAAT*GGGAGCAGAAAT
GAAGAGCCTCTCGCAGAGATCAGTACCCAACACCTGCACCCTAGTCATGTGTAGCCAACAGAGA
ATGGCCTGCCTGGTCGTGATGGACGGGATGGGAGAGAAGGTCCACGGGGTGAAAGGGTGATCCA
GGTTTGCCAGGACCTATGGGGCTCTCAGGGTTGCAGGGCCCTACAGGTCCAGTTGGACCCAAAGG
AGAGAATGGCTCTGCTGGCGAACCTGGACCAAAGGGAGAACGTGGACTAAGTGGAATGGCTGATT
CCCATAACACCCAATACTGCAACCTCGAAGAGAGTGCTCAAGCCCAACAGGAATTAGACAATGAC
CAGGAGACCATGGAGACATCAGAGGAGGAGGAAGATACCACCACCTCAAATAAAGTGTATGGCAG
TGCAATACCAAGTCCTCCCCAGAGTCCTCAGAGAGCCTACTCTCCCTGTGTGGCACTGGCCTCCA
TCCCTGATAGCCCATCTGAGGAAGCTTCCATCAAAGGATCAGAGGGCCTGGAAGACCCACTTCAT
TTGTTGCACAATGCACAGAACACAAAGGTGTATGACTTGGTGGACTTTCTGGTTTTAAACTATCA
AATGAAGGCATTCACTACCAAAGCAGAAATGTTGGAAAATATTGGTAGAGAGTATGAGGAGTACT
ACCCTCTGATCTTTAGTGAGGCCTCTGAGTGCTTGAAGATGGTCTTTGGCCTTGACATGGTAGAA
GTGGACTCCTCTGTCCACACCTATATGCTTGTCACTGCCCTGGGGATCACCTATGATGGCATGAT
GACTGATGTCCAGGGTATGCCCAAGACAGGTATCCTCATAGCTGTACTGAGTGTCATTTTCATGA
AGGGAAACTATGTCAGTGAGGAGATTATCTGGGAAATGCTGAATAACATAGGGTTGTGTGGTGGG
AGGGATCCTTACATACATAAAGACCCCAGGAAGCTCATCTCTGAGGAGTTTGTGCAGGAAGGGTA
CCTGGAATACAGGCAGGTGCCCAATAGTGATCCCCCTAGCTATGGGTTCCTGTGGGGCCCAAGGG
CTTTTGCAGAAACCAGCAAAATGAAAGTCTTACAGTTCTTTGCCAGCATTAATAAGACTCATCCC
AGAGCCTACCCTGAAAAGTATGCAGAGGCTTTACAAGATGAGATAGACAGGACCAAGACCTGGAT
CTTGAACAGATGCTCCAACTCCTCTGACCTACACACATTC*GGGAACATAGGACCTCAAGGCAAAC
CAGGTCCTAAAGGAGAGGCTGGGCCCAAAGGA*GAAGTAGGTGCTCCTGGCATGCAAGGATCTACA
GGGGGCAAAAGGCTCCACAGGCCCCAAGGGAGA*AAGAGGTGCCCCTGGTGTGCAAGGAGCCCCAGG
GAATGCTGGAGCAGCAGGACCTGCCGGACCTG*CCGGTCCACAGGGAGCTCCAGGTTCCAGGGGGC
CCCCAGGACTCAAGGGGGACAGAGGTGTTCCT*GGAGACAGAGGAATCAAAGGTGAAAGCGGGCTT
CCAGACAGTGCTGCTCT*AGAAAGCTGCATTGTTCCCTGATGGCCAGTTGGCTGCCTTGCAAGCAG
ACCTGATGAACCTGCGCATGGAGCTGCAGAGCTACCGAGGTTCAGCAACACCAGCCGCCGCGGGT
GCTCCAGAGTTGACCGCTGGAGTCAAACTCCTGACACCGGCAGCTCCTGACCCCACAACTCCAG
CCGCGGCCACAGGAACAGACGCGCTTTCCAGGGACCAGAGGAAACAGAACAAGATGTAGACCTCT
CAGCTCCTCCTGCACCATGCCTGCCTGGATGCCGCCATTCTCAACATGATGATAATGGAATGAAC
CTCAGAAACATCATTCAAGACTGTCTGCAGCTGATTGCAGACAGCGACACGCCGACTATACGAAA
AGGAACTTACACATTTGTTCCATGGCTTCTCAGCTTTAAAAGAGGAAATGCCTTGGAGGAGAAAG
AGAACAAAATAGTGGTGAGGCAAACAGGCTATTTCTTCATCTACAGCCAGGTTCTATACACGGAC
CCCATCTTTGCTATGGGTCATGTCATCCAGAGGAAGAAAGTACACGTCTTTGGGGACGAGCTGAG
CCTGGTGACCCTGTTCCGATGTATTCAGAATATGCCCAAAACACTGCCCAACAATTCCTGCTACT
CGGCTGGCATCGCGAGGCTGGAAGAAGGAGATGAGATTCAGCTTGCAATTCCTCGGGAGAATGCA
CAGATTTCACGCAACGGAGACGACACCTTCTTTGGTGCCCTAAAACTGCTGTAA

<210> SEQ ID NO 18

<211> LENGTH: 797

<212> TYPE: PRT

<213> ORGANISM: Artificial Sequence

<220> FEATURE:

<223> OTHER INFORMATION: Murine Surfactant Protein D collagen-like domain fused to murine MAGE-A3 and the extracellular domain of murine BAFF. Deleted 20 aa of SP-D sequence.

MLPFLSMLVLLVQPLGNLGAEMKSLSQ

<213> ORGANISM: Artificial Sequence
<220> FEATURE:
<223> OTHER INFORMATION: Fusion protein

<400> SEQUENCE: 1

| | | | | | | |
|---|---|---|---|---|---|---|
| atgctgccct | ttctctccat | gcttgtcttg | cttgtacagc | ccctgggaaa | tctgggagca | 60 |
| gaaatgaaga | gcctctcgca | gagatcagta | cccaacacct | gcaccctagt | catgtgtagc | 120 |
| ccaacagaga | atggcctgcc | tggtcgtgat | ggacgggatg | ggagagaagg | tccacggggt | 180 |
| gagaagggtg | atccaggttt | gccaggacct | atgggctct | cagggttgca | gggccctaca | 240 |
| ggtccagttg | acccaaaagg | agagaatggc | tctgctggcg | aacctggacc | aaagggagaa | 300 |
| cgtggactaa | gtggaatggg | agccagggcc | agcgtgctgt | ctggggcga | gctggacagg | 360 |
| tgggagaaga | ttaggctgag | gcccggagga | agaagaagt | acaaactgaa | acacatcgtg | 420 |
| tgggcctccc | gggagctgga | acggttcgcc | gtgaatcctg | ggctgctgga | gacctctgag | 480 |
| ggctgcagac | agatcctggg | acagctgcag | cctagcctgc | agaccggaag | cgaggagctg | 540 |
| aggtctctgt | acaacaccgt | ggccacactg | tactgcgtgc | accagcggat | tgaggtgaag | 600 |
| gataccaagg | aagccctgga | gaagattgag | gaagagcaga | ataagtccaa | gaagaaagcc | 660 |
| cagcaggccg | ccgccgacac | aggaaatagc | tcccaggtgt | ctcagaacta | ccccatcgtg | 720 |
| cagaacctgc | agggacagat | ggtgcaccag | gccatcagcc | ccggaccct | gaacgcctgg | 780 |
| gtgaaggtgg | tggaagagaa | agccttcagc | ccagaagtga | tccccatgtt | cagcgccctg | 840 |
| agcgaagggg | ccaccccaca | ggacctgaat | acaatgctga | atacagtggg | cggccaccag | 900 |
| gccgccatgc | agatgctgaa | ggagaccatt | aacgaggagg | ccgccgagtg | ggataggctg | 960 |
| cacccagtgc | acgccgggcc | atcgccccca | gggcagatga | gggagccacg | gggctctgac | 1020 |
| atcgccggca | ccacctctac | cctgcaggag | cagatcggct | ggatgaccaa | taacccacct | 1080 |
| attcccgtgg | agaaatcta | caaaggtgg | attatcctgg | ggctgaacaa | gatcgtgaga | 1140 |
| atgtactccc | caacatccat | tctggacatc | cggcagggcc | caaaggaacc | ctttagagac | 1200 |
| tacgtggata | ggttctacaa | aaccctgcgc | gccgagcagg | cctcccagga | ggtgaagaac | 1260 |
| tggatgaccg | agacactgct | ggtgcagaat | gccaacccag | actgtaagac | cattctgaag | 1320 |
| gccctgggac | cagccgccac | cctggaggaa | atgatgacag | cctgccaggg | ggtgggcgga | 1380 |
| cccggccaca | aggcccgcgt | gctggccgag | gccatgtccc | aggtgacaaa | ttccgccacc | 1440 |
| atcatgatgc | agcgcggaaa | ttttcggaat | cagcgcaaaa | cagtgaaatg | cttcaattgc | 1500 |
| gggaaggagg | ccacatcgc | caagaattgc | agagccccaa | ggaagaaggg | ctgctggaag | 1560 |
| tgcggaaagg | agggccacca | gatgaaggac | tgcacagagc | gccaggccaa | tttcctgggc | 1620 |
| aagatctggc | catcccacaa | ggggcggcct | ggaaacttcc | tgcagagccg | gcccgaaccc | 1680 |
| acagcccccc | ctgaagaatc | cttccggttc | ggagaggaaa | caaccacacc | cagccagaag | 1740 |
| caggagccta | tcgacaagga | actgtaccca | ctggccagcc | tgagaagcct | gttcggcaac | 1800 |
| gatccaagca | gccagcctcc | aggacttcca | ggtattcctg | gtccagctgg | aaagaaggt | 1860 |
| ccctctggga | agcaggggaa | cataggacct | caaggcaaac | aggtcctaa | aggagaggct | 1920 |
| gggcccaaag | agaagtagg | tgctcctggc | atgcaaggat | ctacagggc | aaaaggctcc | 1980 |
| acaggcccca | agggagaaag | aggtgcccct | ggtgtgcaag | agccccagg | gaatgctgga | 2040 |
| gcagcaggac | ctgccggacc | tgccggtcca | cagggagctc | caggttccag | ggggccccca | 2100 |
| ggactcaagg | gggacagagg | tgttcctgga | gacagagga | tcaaaggtga | agcgggctt | 2160 |
| ccagacagtg | ctgctctgag | gcagcagatg | gaggccttaa | aaggaaaact | acagcgtcta | 2220 |

```
gaggttgcct tctcccacta tcagaaagct gcattgttcc ctgatggcca tagaagattg    2280
gataaggtcg aagaggaagt aaaccttcat gaagattttg tattcataaa aaagctaaag    2340
agatgcaaca aaggagaagg atctttatcc ttgctgaact gtgaggagat gagaaggcaa    2400
tttgaagacc ttgtcaagga tataacgtta aacaaagaag agaaaaaaga aaacagcttt    2460
gaaatgcaaa gaggtgatga ggatcctcaa attgcagcac acgttgtaag cgaagccaac    2520
agtaatgcag catccgttct acagtgggcc aagaaaggat attataccat gaaaagcaac    2580
ttggtaatgc ttgaaaatgg gaaacagctg acggttaaaa gagaaggact ctattatgtc    2640
tacactcaag tcaccttctg ctctaatcgg gagccttcga gtcaacgccc attcatcgtc    2700
ggcctctggc tgaagcccag cattggatct gagagaatct tactcaaggc ggcaaatacc    2760
cacagttcct cccagctttg cgagcagcag tctgttcact gggcggagt gtttgaatta    2820 caagctggtg cttctgtgtt tgtcaacgtg actgaagcaa gccaagtgat ccacagagtt    2880
ggcttctcat cttttggctt actcaaactc tga                                 2913
```

<210> SEQ ID NO 2
<211> LENGTH: 970
<212> TYPE: PRT
<213> ORGANISM: Artificial Sequence
<220> FEATURE:
<223> OTHER INFORMATION: Fusion protein

<400> SEQUENCE: 2

```
Met Leu Pro Phe Leu Ser Met Leu Val Leu Val Gln Pro Leu Gly
1               5                   10                  15

Asn Leu Gly Ala Glu Met Lys Ser Leu Ser Gln Arg Ser Val Pro Asn
                20                  25                  30

Thr Cys Thr Leu Val Met Cys Ser Pro Thr Glu Asn Gly Leu Pro Gly
            35                  40                  45

Arg Asp Gly Arg Asp Gly Arg Glu Gly Pro Arg Gly Glu Lys Gly Asp
        50                  55                  60

Pro Gly Leu Pro Gly Pro Met Gly Leu Ser Gly Leu Gln Gly Pro Thr
65                  70                  75                  80

Gly Pro Val Gly Pro Lys Gly Glu Asn Gly Ser Ala Gly Glu Pro Gly
                85                  90                  95

Pro Lys Gly Glu Arg Gly Leu Ser Gly Met Gly Ala Arg Ala Ser Val
            100                 105                 110

Leu Ser Gly Gly Glu Leu Asp Arg Trp Glu Lys Ile Arg Leu Arg Pro
        115                 120                 125

Gly Gly Lys Lys Lys Tyr Lys Leu Lys His Ile Val Trp Ala Ser Arg
    130                 135                 140

Glu Leu Glu Arg Phe Ala Val Asn Pro Gly Leu Leu Glu Thr Ser Glu
145                 150                 155                 160

Gly Cys Arg Gln Ile Leu Gly Gln Leu Gln Pro Ser Leu Gln Thr Gly
                165                 170                 175

Ser Glu Glu Leu Arg Ser Leu Tyr Asn Thr Val Ala Thr Leu Tyr Cys
            180                 185                 190

Val His Gln Arg Ile Glu Val Lys Asp Thr Lys Glu Ala Leu Glu Lys
        195                 200                 205

Ile Glu Glu Glu Gln Asn Lys Ser Lys Lys Lys Ala Gln Gln Ala Ala
    210                 215                 220

Ala Asp Thr Gly Asn Ser Ser Gln Val Ser Gln Asn Tyr Pro Ile Val
225                 230                 235                 240
```

```
Gln Asn Leu Gln Gly Gln Met Val His Gln Ala Ile Ser Pro Arg Thr
                245                 250                 255

Leu Asn Ala Trp Val Lys Val Val Glu Lys Ala Phe Ser Pro Glu
        260                 265                 270

Val Ile Pro Met Phe Ser Ala Leu Ser Glu Gly Ala Thr Pro Gln Asp
    275                 280                 285

Leu Asn Thr Met Leu Asn Thr Val Gly Gly His Gln Ala Ala Met Gln
290                 295                 300

Met Leu Lys Glu Thr Ile Asn Glu Glu Ala Ala Glu Trp Asp Arg Leu
305                 310                 315                 320

His Pro Val His Ala Gly Pro Ile Ala Pro Gly Gln Met Arg Glu Pro
                325                 330                 335

Arg Gly Ser Asp Ile Ala Gly Thr Thr Ser Thr Leu Gln Glu Gln Ile
            340                 345                 350

Gly Trp Met Thr Asn Asn Pro Pro Ile Pro Val Gly Glu Ile Tyr Lys
        355                 360                 365

Arg Trp Ile Ile Leu Gly Leu Asn Lys Ile Val Arg Met Tyr Ser Pro
    370                 375                 380

Thr Ser Ile Leu Asp Ile Arg Gln Gly Pro Lys Glu Pro Phe Arg Asp
385                 390                 395                 400

Tyr Val Asp Arg Phe Tyr Lys Thr Leu Arg Ala Glu Gln Ala Ser Gln
                405                 410                 415

Glu Val Lys Asn Trp Met Thr Glu Thr Leu Leu Val Gln Asn Ala Asn
            420                 425                 430

Pro Asp Cys Lys Thr Ile Leu Lys Ala Leu Gly Pro Ala Ala Thr Leu
        435                 440                 445

Glu Glu Met Met Thr Ala Cys Gln Gly Val Gly Gly Pro Gly His Lys
    450                 455                 460

Ala Arg Val Leu Ala Glu Ala Met Ser Gln Val Thr Asn Ser Ala Thr
465                 470                 475                 480

Ile Met Met Gln Arg Gly Asn Phe Arg Asn Gln Arg Lys Thr Val Lys
                485                 490                 495

Cys Phe Asn Cys Gly Lys Glu Gly His Ile Ala Lys Asn Cys Arg Ala
            500                 505                 510

Pro Arg Lys Lys Gly Cys Trp Lys Cys Gly Lys Glu Gly His Gln Met
        515                 520                 525

Lys Asp Cys Thr Glu Arg Gln Ala Asn Phe Leu Gly Lys Ile Trp Pro
    530                 535                 540

Ser His Lys Gly Arg Pro Gly Asn Phe Leu Gln Ser Arg Pro Glu Pro
545                 550                 555                 560

Thr Ala Pro Pro Glu Glu Ser Phe Arg Phe Gly Glu Glu Thr Thr Thr
                565                 570                 575

Pro Ser Gln Lys Gln Glu Pro Ile Asp Lys Glu Leu Tyr Pro Leu Ala
            580                 585                 590

Ser Leu Arg Ser Leu Phe Gly Asn Asp Pro Ser Ser Gln Pro Pro Gly
        595                 600                 605

Leu Pro Gly Ile Pro Gly Pro Ala Gly Lys Glu Gly Pro Ser Gly Lys
    610                 615                 620

Gln Gly Asn Ile Gly Pro Gln Gly Lys Pro Gly Lys Gly Glu Ala
625                 630                 635                 640

Gly Pro Lys Gly Glu Val Gly Ala Pro Gly Met Gln Gly Ser Thr Gly
                645                 650                 655
```

Ala Lys Gly Ser Thr Gly Pro Lys Gly Glu Arg Gly Ala Pro Gly Val
          660                 665                 670

Gln Gly Ala Pro Gly Asn Ala Gly Ala Gly Pro Ala Gly Pro Ala
      675                 680                 685

Gly Pro Gln Gly Ala Pro Gly Ser Arg Gly Pro Pro Gly Leu Lys Gly
      690                 695                 700

Asp Arg Gly Val Pro Gly Asp Arg Gly Ile Lys Gly Glu Ser Gly Leu
705                 710                 715                 720

Pro Asp Ser Ala Ala Leu Arg Gln Gln Met Glu Ala Leu Lys Gly Lys
              725                 730                 735

Leu Gln Arg Leu Glu Val Ala Phe Ser His Tyr Gln Lys Ala Ala Leu
          740                 745                 750

Phe Pro Asp Gly His Arg Leu Asp Lys Val Glu Glu Val Asn
      755                 760                 765

Leu His Glu Asp Phe Val Phe Ile Lys Lys Leu Lys Arg Cys Asn Lys
      770                 775                 780

Gly Glu Gly Ser Leu Ser Leu Leu Asn Cys Glu Glu Met Arg Arg Gln
785                 790                 795                 800

Phe Glu Asp Leu Val Lys Asp Ile Thr Leu Asn Lys Glu Glu Lys Lys
              805                 810                 815

Glu Asn Ser Phe Glu Met Gln Arg Gly Asp Glu Asp Pro Gln Ile Ala
          820                 825                 830

Ala His Val Val Ser Glu Ala Asn Ser Asn Ala Ala Ser Val Leu Gln
          835                 840                 845

Trp Ala Lys Lys Gly Tyr Tyr Thr Met Lys Ser Asn Leu Val Met Leu
850                 855                 860

Glu Asn Gly Lys Gln Leu Thr Val Lys Arg Glu Gly Leu Tyr Tyr Val
865                 870                 875                 880

Tyr Thr Gln Val Thr Phe Cys Ser Asn Arg Glu Pro Ser Ser Gln Arg
              885                 890                 895

Pro Phe Ile Val Gly Leu Trp Leu Lys Pro Ser Ile Gly Ser Glu Arg
          900                 905                 910

Ile Leu Leu Lys Ala Ala Asn Thr His Ser Ser Gln Leu Cys Glu
          915                 920                 925

Gln Gln Ser Val His Leu Gly Gly Val Phe Glu Leu Gln Ala Gly Ala
      930                 935                 940

Ser Val Phe Val Asn Val Thr Glu Ala Ser Gln Val Ile His Arg Val
945                 950                 955                 960

Gly Phe Ser Ser Phe Gly Leu Leu Lys Leu
              965                 970

<210> SEQ ID NO 3
<211> LENGTH: 2784
<212> TYPE: DNA
<213> ORGANISM: Artificial Sequence
<220> FEATURE:
<223> OTHER INFORMATION: Fusion protein

<400> SEQUENCE: 3
atggatgcaa tgaagagagg gctctgctgt gtgctgctgc tgtgtggagc agtcttcgtt      60
tcgcccagcg aagatgacgt tactacaact gaagagctag ctcctgcttt ggtccctcca     120
cccaagggaa cttgtgcagg ttggatggca ggcatcccag acatcctggc cacaatggc     180 acaccaggcc gtgatggctg gggcaacctg tgggtgaccg tgtactacgg cgtgcccgtg     240
tggaaggagg ccaagaccac cctgttctgc gccagcgacg ccaagagcta cgagaaggag     300

```
gtgcacaacg tgtgggccac ccacgcctgc gtgcccaccg accccaaccc ccaggagatc    360
gtgctgggca acgtgaccga gaacttcaac atgtggaaga acgacatggt ggaccagatg    420
cacgaggaca tcatcagcct gtgggaccag agcctgaagc cctgcgtgaa gctgacccccc   480
ctgtgcgtga ccctgaactg caccgaggtg aacgtgaccc gcaacgtgaa caacagcgtg    540
gtgaacaaca ccaccaacgt gaacaacagc atgaacggcg acatgaagaa ctgcagcttc    600
aacatcacca ccgagctgaa ggacaagaag aagaacgtgt acgccctgtt ctacaagctg    660
gacatcgtga gcctgaacga gaccgacgac agcgagaccg gcaacagcag caagtactac    720
cgcctgatca actgcaacac cagcgccctg acccaggcct gccccaaggt gagcttcgac    780
cccatcccca tccactactg cgccccgcc ggctacgcca tcctgaagtg caacaacaag    840
accttcaacg gcaccggccc ctgccacaac gtgagcaccg tgcagtgcac ccacggcatc    900
aagcccgtgg tgagcaccca gctgctgctg aacggcagcc tggccgagga gggcatcatc    960
atccgcagcg agaacctgac caacaacgtc aagaccatca tcgtgcacct gaaccgcagc    1020
atcgagatcg tgtgcgtgcg ccccaacaac aacacccgcc agagcatccg catcggcccc    1080
ggccagacct tctacgccac cggcgacatc atcggcgaca tccgccaggc ccactgcaac    1140
atcagccgca ccaactggac caagaccctg cgcgaggtgc gcaacaagct gcgcgagcac    1200
ttccccaaca gaacatcac cttcaagccc agcagcggcg gcgacctgga gatcaccacc    1260
cacagcttca actgccgcgg cgagttcttc tactgcaaca ccagcggcct gttcagcatc    1320
aactacaccg agaacaacac cgacggcacc cccatcaccc tgccctgccg catccgccag    1380
atcatcaaca tgtggcagga ggtgggccgc gccatgtacg ccccccccat cgagggcaac    1440
atcgcctgca gagcgacat caccggcctg ctgctggtgc gcgacggcgg cagcaccaac    1500
gacagcacca acaacaacac cgagatcttc cgccccgccg gcggcgacat gcgcgacaac    1560
tggcgcagcg agctgtacaa gtacaaggtg gtggagatca gcccctggg catcgccccc    1620
accgaggcca agcgccgcgt ggtggagcgc gagaagcgcg ccgtgggcat cggcgccgtg    1680
ttcctgggct tcctgggcgc cgccggcagc accatgggcg ccgccagcat caccctgacc    1740
gcccaggccc gccaggtgct gagcggcatc gtgcagcagc agagcaacct gctgcgcgcc    1800
atcgaggccc agcagcacct gctgcagctg accgtgtggg gcatcaagca gctgcagacc    1860
cgcgtgctgg ccatcgagcg ctacctgaag gaccagcagc tgctgagaga tggcactcct    1920
ggagagaagg gagagaaagg agatgcaggt cttcttggtc ctaagggtga gacaggagat    1980
gttgaatga caggagctga agggccacgg ggcttccccg gaacccctgg caggaaagga    2040
gagcctggag aagccgctca gttggctgcc ttgcaagcag acctgatgaa cctgcgcatg    2100
gagctgcaga gctaccgagg ttcagcaaca ccagccgccg cgggtgctcc agagttgacc    2160
gctggagtca aactcctgac accggcagct cctcgacccc acaactccag ccgcggccac    2220
aggaacagac gcgctttcca gggaccagag gaaacagaac aagatgtaga cctctcagct    2280
cctcctgcac catgcctgcc tggatgccgc cattctcaac atgatgataa tggaatgaac    2340
ctcagaaaca tcattcaaga ctgtctgcag ctgattgcag acagcgacac gccgactata    2400
cgaaaaggaa cttacacatt tgttccatgg cttctcagct ttaaaagagg aaatgccttg    2460
gaggagaaag agaacaaaat agtggtgagg caaacaggct atttcttcat ctacagccag    2520
gttctataca cggaccccat cttttgctat ggtcatgtca tccagaggaa gaaagtacac    2580
gtctttgggg acgagctgag cctggtgacc ctgttccgat gtattcagaa tatgcccaaa    2640
```

```
acactgccca caattcctg ctactcggct ggcatcgcga ggctggaaga aggagatgag    2700
attcagcttg caattcctcg ggagaatgca cagatttcac gcaacggaga cgacaccttc    2760
tttggtgccc taaaactgct gtaa                                           2784
```

<210> SEQ ID NO 4
<211> LENGTH: 927
<212> TYPE: PRT
<213> ORGANISM: Artificial Sequence
<220> FEATURE:
<223> OTHER INFORMATION: Fusion protein

<400> SEQUENCE: 4

```
Met Asp Ala Met Lys Arg Gly Leu Cys Cys Val Leu Leu Leu Cys Gly
1               5                   10                  15

Ala Val Phe Val Ser Pro Ser Glu Asp Asp Val Thr Thr Thr Glu Glu
            20                  25                  30

Leu Ala Pro Ala Leu Val Pro Pro Lys Gly Thr Cys Ala Gly Trp
        35                  40                  45

Met Ala Gly Ile Pro Gly His Pro Gly His Asn Gly Thr Pro Gly Arg
    50                  55                  60

Asp Gly Trp Gly Asn Leu Trp Val Thr Val Tyr Tyr Gly Val Pro Val
65                  70                  75                  80

Trp Lys Glu Ala Lys Thr Thr Leu Phe Cys Ala Ser Asp Ala Lys Ser
                85                  90                  95

Tyr Glu Lys Glu Val His Asn Val Trp Ala Thr His Ala Cys Val Pro
            100                 105                 110

Thr Asp Pro Asn Pro Gln Glu Ile Val Leu Gly Asn Val Thr Glu Asn
        115                 120                 125

Phe Asn Met Trp Lys Asn Asp Met Val Asp Gln Met His Glu Asp Ile
    130                 135                 140

Ile Ser Leu Trp Asp Gln Ser Leu Lys Pro Cys Val Lys Leu Thr Pro
145                 150                 155                 160

Leu Cys Val Thr Leu Asn Cys Thr Glu Val Asn Val Thr Arg Asn Val
                165                 170                 175

Asn Asn Ser Val Val Asn Asn Thr Thr Asn Val Asn Asn Ser Met Asn
            180                 185                 190

Gly Asp Met Lys Asn Cys Ser Phe Asn Ile Thr Thr Glu Leu Lys Asp
        195                 200                 205

Lys Lys Lys Asn Val Tyr Ala Leu Phe Tyr Lys Leu Asp Ile Val Ser
    210                 215                 220

Leu Asn Glu Thr Asp Asp Ser Glu Thr Gly Asn Ser Ser Lys Tyr Tyr
225                 230                 235                 240

Arg Leu Ile Asn Cys Asn Thr Ser Ala Leu Thr Gln Ala Cys Pro Lys
                245                 250                 255

Val Ser Phe Asp Pro Ile Pro Ile His Tyr Cys Ala Pro Ala Gly Tyr
            260                 265                 270

Ala Ile Leu Lys Cys Asn Asn Lys Thr Phe Asn Gly Thr Gly Pro Cys
        275                 280                 285

His Asn Val Ser Thr Val Gln Cys Thr His Gly Ile Lys Pro Val Val
    290                 295                 300

Ser Thr Gln Leu Leu Leu Asn Gly Ser Leu Ala Glu Glu Gly Ile Ile
305                 310                 315                 320

Ile Arg Ser Glu Asn Leu Thr Asn Asn Val Lys Thr Ile Ile Val His
                325                 330                 335
```

-continued

```
Leu Asn Arg Ser Ile Glu Ile Val Cys Val Arg Pro Asn Asn Asn Thr
            340                 345                 350
Arg Gln Ser Ile Arg Ile Gly Pro Gly Gln Thr Phe Tyr Ala Thr Gly
        355                 360                 365
Asp Ile Ile Gly Asp Ile Arg Gln Ala His Cys Asn Ile Ser Arg Thr
    370                 375                 380
Asn Trp Thr Lys Thr Leu Arg Glu Val Arg Asn Lys Leu Arg Glu His
385                 390                 395                 400
Phe Pro Asn Lys Asn Ile Thr Phe Lys Pro Ser Ser Gly Gly Asp Leu
                405                 410                 415
Glu Ile Thr Thr His Ser Phe Asn Cys Arg Gly Glu Phe Phe Tyr Cys
            420                 425                 430
Asn Thr Ser Gly Leu Phe Ser Ile Asn Tyr Thr Glu Asn Asn Thr Asp
        435                 440                 445
Gly Thr Pro Ile Thr Leu Pro Cys Arg Ile Arg Gln Ile Ile Asn Met
    450                 455                 460
Trp Gln Glu Val Gly Arg Ala Met Tyr Ala Pro Pro Ile Glu Gly Asn
465                 470                 475                 480
Ile Ala Cys Lys Ser Asp Ile Thr Gly Leu Leu Leu Val Arg Asp Gly
                485                 490                 495
Gly Ser Thr Asn Asp Ser Thr Asn Asn Asn Thr Glu Ile Phe Arg Pro
            500                 505                 510
Ala Gly Gly Asp Met Arg Asp Asn Trp Arg Ser Glu Leu Tyr Lys Tyr
        515                 520                 525
Lys Val Val Glu Ile Lys Pro Leu Gly Ile Ala Pro Thr Glu Ala Lys
    530                 535                 540
Arg Arg Val Val Glu Arg Glu Lys Arg Ala Val Gly Ile Gly Ala Val
545                 550                 555                 560
Phe Leu Gly Phe Leu Gly Ala Ala Gly Ser Thr Met Gly Ala Ala Ser
                565                 570                 575
Ile Thr Leu Thr Ala Gln Ala Arg Gln Val Leu Ser Gly Ile Val Gln
            580                 585                 590
Gln Gln Ser Asn Leu Leu Arg Ala Ile Glu Ala Gln Gln His Leu Leu
        595                 600                 605
Gln Leu Thr Val Trp Gly Ile Lys Gln Leu Gln Thr Arg Val Leu Ala
    610                 615                 620
Ile Glu Arg Tyr Leu Lys Asp Gln Gln Leu Leu Arg Asp Gly Thr Pro
625                 630                 635                 640
Gly Glu Lys Gly Glu Lys Gly Asp Ala Gly Leu Leu Gly Pro Lys Gly
                645                 650                 655
Glu Thr Gly Asp Val Gly Met Thr Gly Ala Glu Gly Pro Arg Gly Phe
            660                 665                 670
Pro Gly Thr Pro Gly Arg Lys Gly Glu Pro Gly Glu Ala Ala Gln Leu
        675                 680                 685
Ala Ala Leu Gln Ala Asp Leu Met Asn Leu Arg Met Glu Leu Gln Ser
    690                 695                 700
Tyr Arg Gly Ser Ala Thr Pro Ala Ala Gly Ala Pro Glu Leu Thr
705                 710                 715                 720
Ala Gly Val Lys Leu Thr Pro Ala Ala Pro Arg Pro His Asn Ser
                725                 730                 735
Ser Arg Gly His Arg Asn Arg Ala Phe Gln Gly Pro Glu Glu Thr
            740                 745                 750
Glu Gln Asp Val Asp Leu Ser Ala Pro Pro Ala Pro Cys Leu Pro Gly
```

|     | 755 |     |     | 760 |     |     | 765 |     |     |
|-----|-----|-----|-----|-----|-----|-----|-----|-----|-----|

Cys Arg His Ser Gln His Asp Asp Asn Gly Met Asn Leu Arg Asn Ile
      770                 775                 780

Ile Gln Asp Cys Leu Gln Leu Ile Ala Asp Ser Asp Thr Pro Thr Ile
785                 790                 795                 800

Arg Lys Gly Thr Tyr Thr Phe Val Pro Trp Leu Leu Ser Phe Lys Arg
                805                 810                 815

Gly Asn Ala Leu Glu Glu Lys Glu Asn Lys Ile Val Arg Gln Thr
            820                 825                 830

Gly Tyr Phe Phe Ile Tyr Ser Gln Val Leu Tyr Thr Asp Pro Ile Phe
        835                 840                 845

Ala Met Gly His Val Ile Gln Arg Lys Lys Val His Val Phe Gly Asp
      850                 855                 860

Glu Leu Ser Leu Val Thr Leu Phe Arg Cys Ile Gln Asn Met Pro Lys
865                 870                 875                 880

Thr Leu Pro Asn Asn Ser Cys Tyr Ser Ala Gly Ile Ala Arg Leu Glu
                885                 890                 895

Glu Gly Asp Glu Ile Gln Leu Ala Ile Pro Arg Glu Asn Ala Gln Ile
            900                 905                 910

Ser Arg Asn Gly Asp Asp Thr Phe Phe Gly Ala Leu Lys Leu Leu
        915                 920                 925

<210> SEQ ID NO 5
<211> LENGTH: 3129
<212> TYPE: DNA
<213> ORGANISM: Artificial Sequence
<220> FEATURE:
<223> OTHER INFORMATION: Fusion protein

<400> SEQUENCE: 5

| atgctgccct | tctctccat | gcttgtcttg | cttgtacagc | ccctgggaaa | tctgggagca | 60 |
| gaaatgaaga | gcctctcgca | gagatcagta | cccaacacct | gcaccctagt | catgtgtagc | 120 |
| ccaacagaga | atggcctgcc | tggtcgtgat | ggacgggatg | ggagagaagg | tccacggggt | 180 |
| gagaagggtg | atccaggttt | gccaggacct | atggggctct | cagggttgca | gggccctaca | 240 |
| ggtccagttg | acccaaaagg | agagaatggc | tctgctggcg | aacctggacc | aaagggagaa | 300 |
| cgtggactaa | gtgaaaaagt | acccagaaac | caggactggc | ttggtgtctc | aaggcaactc | 360 |
| agaaccaaag | cctggaacag | gcagctgtat | ccagagtgga | cagaagccca | gagacttgac | 420 |
| tgctggagag | gtggtcaagt | gtccctcaag | gtcagtaatg | atgggcctac | actgattggt | 480 |
| gcaaatgcct | ccttctctat | gcccttgaac | ttccctggaa | gccaaaaggt | attgccagat | 540 |
| gggcaggtta | tctgggtcaa | caataccatc | atcaatggga | gccaggtgtg | ggaggacag | 600 |
| ccagtgtatc | cccaggaaac | tgacgatgcc | tgcatcttcc | ctgatggtgg | accttgccca | 660 |
| tctggctctt | ggtctcagaa | gagaagcttt | gtttatgtct | ggaagacctg | gggccaatac | 720 |
| tggcaagttc | tagggggccc | agtgtctggg | ctgagcattg | gacaggcag | gcaatgctg | 780 |
| ggcacacaca | ccatggaagt | gactgtctac | catcgccggg | gatcccggag | ctatgtgcct | 840 |
| cttgctcatt | ccagctcagc | cttcaccatt | actgaccagg | tgccttctc | cgtgagcgtg | 900 |
| tcccagttgc | gggccttgga | tggagggaac | aagcacttcc | tgagaaatca | gcctctgacc | 960 |
| tttgccctcc | agctccatga | ccccagtggc | tatctggctg | aagctgacct | ctcctacacc | 1020 |
| tgggactttg | agacagtag | tggaacccctg | atctctcggg | cacttgtggt | cactcatact | 1080 |
| tacctggagc | ctgcccagt | cactgcccag | gtggtcctgc | aggctgccat | tcctctcacc | 1140 |

```
tcctgtggct cctccccagt tccaggcacc acagatgggc acaggccaac tgcagaggcc    1200
cctaacacca cagctggcca agtgcctact acagaagttg tgggtactac acctggtcag    1260
gcgccaactg cagagccctc tggaaccaca tctgtgcagg tgccaaccac tgaagtcata    1320
agcactgcac ctgtgcagat gccaactgca gagagcacag gtatgacacc tgagaaggtg    1380
ccagtttcag aggtcatggg taccacactg gcagagatgt caactccaga ggctacaggt    1440
atgacacctg cagaggtatc aattgtggtg ctttctggaa ccacagctgc acaggtaaca    1500
actacagagt gggtggagac cacagctaga gagctaccta tccctgagcc tgaaggtcca    1560
gatgccagct caatcatgtc tacggaaagt attacaggtt ccctgggccc cctgctggat    1620
ggtacagcca ccttaaggct ggtgaagaga caagtccccc tggattgtgt tctgtatcga    1680
tatggttcct tttccgtcac cctggacatt gtccagggta ttgaaagtgc cgagatcctg    1740
caggctgtgc cgtccggtga gggggatgca tttgagctga ctgtgtcctg ccaaggcggg    1800
ctgcccaagg aagcctgcat ggagatctca tcgccaggt gccagccccc tgcccagcgg    1860
ctgtgccagc ctgtgctacc cagcccagcc tgccagctgg ttctgcacca gatactgaag    1920
ggtggctcgg ggacatactg cctcaatgtg tctctggctg ataccaacag cctggcagtg    1980
gtcagcaccc agcttatcat gcctggtcaa gaagcaggcc ttgggcaggt tcctccagga    2040
cttccaggta ttcctggtcc agctgggaaa gaaggtccct ctgggaagca gggaacata     2100 ggacctcaag gcaaaccagg tcctaaagga gaggctgggc caaaggaga agtaggtgct    2160 cctggcatgc aaggatctac aggggcaaaa ggctccacag gccccaaggg agaaagaggt    2220
gcccctggtg tgcaaggagc cccagggaat gctggagcag caggacctgc cggacctgcc    2280
ggtccacagg gagctccagg ttccaggggg cccccaggac tcaaggggga cagaggtgtt    2340
cctggagaca gaggaatcaa aggtgaaagc gggcttccag acagtgctgc tctgaggcag    2400
cagatggagg ccttaaaagg aaaactacag cgtctagagg ttgccttctc ccactatcag    2460
aaagctgcat tgttccctga tggccataga agattggata aggtcgaaga ggaagtaaac    2520
cttcatgaag attttgtatt cataaaaaag ctaaagagat gcaacaaagg agaaggatct    2580
ttatccttgc tgaactgtga ggagatgaga aggcaatttg aagaccttgt caaggatata    2640
acgttaaaca aagaagagaa aaaagaaaac agctttgaaa tgcaaagagg tgatgaggat    2700
cctcaaattg cagcacacgt tgtaagcgaa gccaacagta tgcagcatc cgttctacag    2760 tgggccaaga aggatatta ccatgaaa agcaacttgg taatgcttga aatgggaaa     2820 cagctgacgg ttaaaagaga aggactctat tatgtctaca ctcaagtcac cttctgctct    2880
aatcgggagc cttcgagtca acgcccattc atcgtcggcc tctggctgaa gcccagcatt    2940
ggatctgaga gaatcttact caaggcggca aatacccaca gttcctccca gctttgcgag    3000
cagcagtctg ttcacttggg cggagtgttt gaattacaag ctggtgcttc tgtgtttgtc    3060
aacgtgactg aagcaagcca agtgatccac agagttggct tctcatcttt tggcttactc    3120
aaactctga                                                            3129
```

<210> SEQ ID NO 6
<211> LENGTH: 1042
<212> TYPE: PRT
<213> ORGANISM: Artificial Sequence
<220> FEATURE:
<223> OTHER INFORMATION: Fusion protein

<400> SEQUENCE: 6

-continued

```
Met Leu Pro Phe Leu Ser Met Leu Val Leu Val Gln Pro Leu Gly
 1               5                  10                  15

Asn Leu Gly Ala Glu Met Lys Ser Leu Ser Gln Arg Ser Val Pro Asn
                 20                  25                  30

Thr Cys Thr Leu Val Met Cys Ser Pro Thr Glu Asn Gly Leu Pro Gly
             35                  40                  45

Arg Asp Gly Arg Asp Gly Arg Glu Gly Pro Arg Gly Glu Lys Gly Asp
         50                  55                  60

Pro Gly Leu Pro Gly Pro Met Gly Leu Ser Leu Gln Gly Pro Thr
 65                  70                  75                  80

Gly Pro Val Gly Pro Lys Gly Glu Asn Gly Ser Ala Gly Glu Pro Gly
                 85                  90                  95

Pro Lys Gly Glu Arg Gly Leu Ser Gly Lys Val Pro Arg Asn Gln Asp
            100                 105                 110

Trp Leu Gly Val Ser Arg Gln Leu Arg Thr Lys Ala Trp Asn Arg Gln
            115                 120                 125

Leu Tyr Pro Glu Trp Thr Glu Ala Gln Arg Leu Asp Cys Trp Arg Gly
        130                 135                 140

Gly Gln Val Ser Leu Lys Val Ser Asn Asp Gly Pro Thr Leu Ile Gly
145                 150                 155                 160

Ala Asn Ala Ser Phe Ser Ile Ala Leu Asn Phe Pro Gly Ser Gln Lys
                165                 170                 175

Val Leu Pro Asp Gly Gln Val Ile Trp Val Asn Asn Thr Ile Ile Asn
                180                 185                 190

Gly Ser Gln Val Trp Gly Gly Gln Pro Val Tyr Pro Gln Glu Thr Asp
            195                 200                 205

Asp Ala Cys Ile Phe Pro Asp Gly Gly Pro Cys Pro Ser Gly Ser Trp
        210                 215                 220

Ser Gln Lys Arg Ser Phe Val Tyr Val Trp Lys Thr Trp Gly Gln Tyr
225                 230                 235                 240

Trp Gln Val Leu Gly Gly Pro Val Ser Gly Leu Ser Ile Gly Thr Gly
                245                 250                 255

Arg Ala Met Leu Gly Thr His Thr Met Glu Val Thr Val Tyr His Arg
            260                 265                 270

Arg Gly Ser Arg Ser Tyr Val Pro Leu Ala His Ser Ser Ala Phe
        275                 280                 285

Thr Ile Thr Asp Gln Val Pro Phe Ser Val Ser Val Ser Gln Leu Arg
        290                 295                 300

Ala Leu Asp Gly Gly Asn Lys His Phe Leu Arg Asn Gln Pro Leu Thr
305                 310                 315                 320

Phe Ala Leu Gln Leu His Asp Pro Ser Gly Tyr Leu Ala Glu Ala Asp
                325                 330                 335

Leu Ser Tyr Thr Trp Asp Phe Gly Asp Ser Ser Gly Thr Leu Ile Ser
            340                 345                 350

Arg Ala Leu Val Val Thr His Thr Tyr Leu Glu Pro Gly Pro Val Thr
        355                 360                 365

Ala Gln Val Val Leu Gln Ala Ala Ile Pro Leu Thr Ser Cys Gly Ser
    370                 375                 380

Ser Pro Val Pro Gly Thr Thr Asp Gly His Arg Pro Thr Ala Glu Ala
385                 390                 395                 400

Pro Asn Thr Thr Ala Gly Gln Val Pro Thr Thr Glu Val Val Gly Thr
                405                 410                 415

Thr Pro Gly Gln Ala Pro Thr Ala Glu Pro Ser Gly Thr Thr Ser Val
```

```
                420             425             430
Gln Val Pro Thr Thr Glu Val Ile Ser Thr Ala Pro Val Gln Met Pro
            435             440             445
Thr Ala Glu Ser Thr Gly Met Thr Pro Glu Lys Val Pro Val Ser Glu
        450             455             460
Val Met Gly Thr Thr Leu Ala Glu Met Ser Thr Pro Glu Ala Thr Gly
465             470             475             480
Met Thr Pro Ala Glu Val Ser Ile Val Val Leu Ser Gly Thr Thr Ala
            485             490             495
Ala Gln Val Thr Thr Glu Trp Val Glu Thr Thr Ala Arg Glu Leu
        500             505             510
Pro Ile Pro Glu Pro Glu Gly Pro Asp Ala Ser Ser Ile Met Ser Thr
        515             520             525
Glu Ser Ile Thr Gly Ser Leu Gly Pro Leu Leu Asp Gly Thr Ala Thr
        530             535             540
Leu Arg Leu Val Lys Arg Gln Val Pro Leu Asp Cys Val Leu Tyr Arg
545             550             555             560
Tyr Gly Ser Phe Ser Val Thr Leu Asp Ile Val Gln Gly Ile Glu Ser
            565             570             575
Ala Glu Ile Leu Gln Ala Val Pro Ser Gly Glu Gly Asp Ala Phe Glu
            580             585             590
Leu Thr Val Ser Cys Gln Gly Gly Leu Pro Lys Glu Ala Cys Met Glu
        595             600             605
Ile Ser Ser Pro Gly Cys Gln Pro Pro Ala Gln Arg Leu Cys Gln Pro
        610             615             620
Val Leu Pro Ser Pro Ala Cys Gln Leu Val Leu His Gln Ile Leu Lys
625             630             635             640
Gly Gly Ser Gly Thr Tyr Cys Leu Asn Val Ser Leu Ala Asp Thr Asn
            645             650             655
Ser Leu Ala Val Val Ser Thr Gln Leu Ile Met Pro Gly Gln Glu Ala
            660             665             670
Gly Leu Gly Gln Val Pro Pro Gly Leu Pro Gly Ile Pro Gly Pro Ala
            675             680             685
Gly Lys Glu Gly Pro Ser Gly Lys Gln Gly Asn Ile Gly Pro Gln Gly
            690             695             700
Lys Pro Gly Pro Lys Gly Glu Ala Gly Pro Lys Gly Glu Val Gly Ala
705             710             715             720
Pro Gly Met Gln Gly Ser Thr Gly Ala Lys Gly Ser Thr Gly Pro Lys
            725             730             735
Gly Glu Arg Gly Ala Pro Gly Val Gln Gly Ala Pro Gly Asn Ala Gly
            740             745             750
Ala Ala Gly Pro Ala Gly Pro Ala Gly Pro Gln Gly Ala Pro Gly Ser
            755             760             765
Arg Gly Pro Pro Gly Leu Lys Gly Asp Arg Gly Val Pro Gly Asp Arg
            770             775             780
Gly Ile Lys Gly Glu Ser Gly Leu Pro Asp Ser Ala Ala Leu Arg Gln
785             790             795             800
Gln Met Glu Ala Leu Lys Gly Lys Leu Gln Arg Leu Glu Val Ala Phe
            805             810             815
Ser His Tyr Gln Lys Ala Ala Leu Phe Pro Asp Gly His Arg Arg Leu
            820             825             830
Asp Lys Val Glu Glu Glu Val Asn Leu His Glu Asp Phe Val Phe Ile
            835             840             845
```

Lys Lys Leu Lys Arg Cys Asn Lys Gly Glu Gly Ser Leu Ser Leu Leu
850                 855                 860

Asn Cys Glu Glu Met Arg Arg Gln Phe Glu Asp Leu Val Lys Asp Ile
865                 870                 875                 880

Thr Leu Asn Lys Glu Glu Lys Lys Glu Asn Ser Phe Glu Met Gln Arg
            885                 890                 895

Gly Asp Glu Asp Pro Gln Ile Ala Ala His Val Val Ser Glu Ala Asn
            900                 905                 910

Ser Asn Ala Ala Ser Val Leu Gln Trp Ala Lys Lys Gly Tyr Tyr Thr
        915                 920                 925

Met Lys Ser Asn Leu Val Met Leu Glu Asn Gly Lys Gln Leu Thr Val
        930                 935                 940

Lys Arg Glu Gly Leu Tyr Tyr Val Tyr Thr Gln Val Thr Phe Cys Ser
945                 950                 955                 960

Asn Arg Glu Pro Ser Ser Gln Arg Pro Phe Ile Val Gly Leu Trp Leu
            965                 970                 975

Lys Pro Ser Ile Gly Ser Glu Arg Ile Leu Leu Lys Ala Ala Asn Thr
            980                 985                 990

His Ser Ser Ser Gln Leu Cys Glu Gln Gln Ser Val His Leu Gly Gly
        995                 1000                1005

Val Phe Glu Leu Gln Ala Gly Ala Ser Val Phe Val Asn Val Thr
    1010                1015                1020

Glu Ala Ser Gln Val Ile His Arg Val Gly Phe Ser Ser Phe Gly
    1025                1030                1035

Leu Leu Lys Leu
    1040

<210> SEQ ID NO 7
<211> LENGTH: 3282
<212> TYPE: DNA
<213> ORGANISM: Artificial Sequence
<220> FEATURE:
<223> OTHER INFORMATION: Fusion protein

<400> SEQUENCE: 7

| | | | | |
|---|---|---|---|---|
| atggatgcaa tgaagagagg ctctgctgt | gtgctgctgc | tgtgtggagc | agtcttcgtt | 60 |
| tcgcccagct cttgtgacaa aactcacaca | tgcccaccgt | gcccagcacc | tgaactcctg | 120 |
| gggggaccgt cagtcttcct cttcccccca | aaacccaagg | acaccctcat | gatctcccgg | 180 |
| accctgaggt ccacatgcgt ggtggtggac | gtgagccacg | aagaccctga | ggtcaagttc | 240 |
| aactggtacg tggacggcgt ggaggtgcat | aatgccaaga | caaagccgcg | ggaggagcag | 300 |
| tacaacagca cgtaccgtgt ggtcagcgtc | ctcaccgtcc | tgcaccagga | ctggctgaat | 360 |
| ggcaaggagt acaagtgcaa ggtctccaac | aaagccctcc | cagcccccat | cgagaaaacc | 420 |
| atctccaaag ccaaagggca gccccgagaa | ccacaggtgt | acaccctgcc | cccatcccgg | 480 |
| gatgagctga ccaagaacca ggtcagcctg | acctgcctgg | tcaaaggctt | ctatcccagc | 540 |
| gacatcgccg tggagtggga gagcaatggg | cagccggaga | acaactacaa | gaccacgcct | 600 |
| cccgtgctgg actccgacgg ctccttcttc | ctctacagca | agctcaccgt | ggacaagagc | 660 |
| aggtggcagc aggggaacgt cttctcatgc | tccgtgatgc | atgaggctct | gcacaaccac | 720 |
| tacacgcaga agagcctctc cctgtctccg | ggtaaatggg | caacctgtg | gtgaccgtg | 780 |
| tactacggcg tgcccgtgtg gaaggaggcc | aagaccaccc | tgttctgcgc | cagcgacgcc | 840 |
| aagagctacg agaaggaggt gcacaacgtg | tgggccaccc | acgcctgcgt | gcccaccgac | 900 |

```
cccaaccccc aggagatcgt gctgggcaac gtgaccgaga acttcaacat gtggaagaac    960
gacatggtgg accagatgca cgaggacatc atcagcctgt gggaccagag cctgaagccc   1020
tgcgtgaagc tgaccccccct gtgcgtgacc ctgaactgca ccgaggtgaa cgtgacccgc   1080
aacgtgaaca cagcgtggt gaacaacacc accaacgtga caacagcat gaacggcgac    1140
atgaagaact gcagcttcaa catcaccacc gagctgaagg acaagaagaa gaacgtgtac   1200
gccctgttct acaagctgga catcgtgagc ctgaacgaga ccgacgacag cgagaccggc   1260
aacagcagca agtactaccg cctgatcaac tgcaacacca gcgccctgac ccaggcctgc   1320
cccaaggtga gcttcgaccc catccccatc cactactgcg ccccgccgg ctacgccatc    1380
ctgaagtgca caacaagac cttcaacggc accggcccct gccacaacgt gagcaccgtg    1440
cagtgcaccc acggcatcaa gccgtggtg agcacccagc tgctgctgaa cggcagcctg    1500
gccgaggagg gcatcatcat ccgcagcgag aacctgacca caacgtcaa gaccatcatc    1560
gtgcacctga ccgcagcat cgagatcgtg tgcgtgcgcc ccaacaacaa cacccgccag    1620
agcatccgca tcggccccgg ccagaccttc tacgccaccg cgacatcat cggcgacatc    1680
cgccaggccc actgcaacat cagccgcacc aactggacca agaccctgcg cgaggtgcgc    1740
aacaagctgc gcgagcactt ccccaacaag aacatcacct tcaagcccag cagcggcggc    1800
gacctggaga tcaccaccca cagcttcaac tgccgcggcg agttcttcta ctgcaacacc    1860
agcggcctgt tcagcatcaa ctacaccgag aacaacaccg acggcacccc catcaccctg    1920
ccctgccgca tccgccagat catcaacatg tggcaggagg tgggccgcgc catgtacgcc    1980
ccccccatcg agggcaacat cgcctgcaag agcgacatca ccggcctgct gctggtgcgc    2040
gacggcggca gcaccaacga cagcaccaac aacaacaccg agatcttccg ccccgccggc    2100
ggcgacatgc gcgacaactg gcgcagcgag ctgtacaagt acaaggtggt ggagatcaag    2160
cccctgggca tcgcccccac cgaggccaag cgccgcgtgg tggagcgcga aagcgcgcc    2220
gtgggcatcg gcgccgtgtt cctgggcttc ctgggcgccg ccggcagcac catgggcgcc    2280
gccagcatca ccctgaccgc ccaggcccgc caggtgctga gcggcatcgt gcagcagcag    2340
agcaacctgc tgcgcgccat cgaggcccag cagcacctgc tgcagctgac cgtgtgggc    2400
atcaagcagc tgcagacccg cgtgctggcc atcgagcgct acctgaagga ccagcagctg    2460
ctgatgaaac agatcgagga taagattgag gaaatcctga gcaagatcta ccatatcgag    2520
aacgaaattg ctaggatcaa aaagctgatc ggcgaggtga tgccagcctc atctccaggc    2580
cacatggggg gctcagtcag agagccagcc ctttcggttg ctctttggtt gagttggggg    2640
gcagttctgg gggctgtgac ttgtgctgtc gcactactga tccaacagac agagctgcaa    2700
agcctaaggc gggaggtgag ccggctgcag cggagtggag ggccttccca gaagcaggga    2760
gagcgcccat ggcagagcct ctgggagcag agtcctgatg tcctggaagc ctggaaggat    2820
ggggcgaaat ctcggagaag gagagcagta ctcacccaga agcacaagaa gaagcactca    2880
gtcctgcatc ttgttccagt taacattacc tccaaggact ctgacgtgac agaggtgatg    2940
tggcaaccag tacttaggcg tgggagaggc ctggaggccc agggagacat tgtacgagtc    3000
tgggacactg gaattatct gctctatagt caggtcctgt ttcatgatgt gactttcaca    3060
atgggtcagg tggtatctcg ggaaggacaa gggagaagag aaactctatt ccgatgtatc    3120
agaagtatgc cttctgatcc tgaccgtgcc tacaatagct gctacagtgc aggtgtcttt    3180
catttacatc aagggatat tatcactgtc aaaattccac gggcaaacgc aaaacttagc    3240
```
ctttctccgc atggaacatt cctggggttt gtgaaactat ga          3282

<210> SEQ ID NO 8
<211> LENGTH: 1093
<212> TYPE: PRT
<213> ORGANISM: Artificial Sequence
<220> FEATURE:
<223> OTHER INFORMATION: Fusion protein

<400> SEQUENCE: 8

```
Met Asp Ala Met Lys Arg Gly Leu Cys Cys Val Leu Leu Leu Cys Gly
1               5                   10                  15

Ala Val Phe Val Ser Pro Ser Ser Cys Asp Lys Thr His Thr Cys Pro
            20                  25                  30

Pro Cys Pro Ala Pro Glu Leu Leu Gly Gly Pro Ser Val Phe Leu Phe
        35                  40                  45

Pro Pro Lys Pro Lys Asp Thr Leu Met Ile Ser Arg Thr Pro Glu Val
    50                  55                  60

Thr Cys Val Val Val Asp Val Ser His Glu Asp Pro Glu Val Lys Phe
65                  70                  75                  80

Asn Trp Tyr Val Asp Gly Val Glu Val His Asn Ala Lys Thr Lys Pro
                85                  90                  95

Arg Glu Glu Gln Tyr Asn Ser Thr Tyr Arg Val Val Ser Val Leu Thr
            100                 105                 110

Val Leu His Gln Asp Trp Leu Asn Gly Lys Glu Tyr Lys Cys Lys Val
        115                 120                 125

Ser Asn Lys Ala Leu Pro Ala Pro Ile Glu Lys Thr Ile Ser Lys Ala
    130                 135                 140

Lys Gly Gln Pro Arg Glu Pro Gln Val Tyr Thr Leu Pro Pro Ser Arg
145                 150                 155                 160

Asp Glu Leu Thr Lys Asn Gln Val Ser Leu Thr Cys Leu Val Lys Gly
                165                 170                 175

Phe Tyr Pro Ser Asp Ile Ala Val Glu Trp Glu Ser Asn Gly Gln Pro
            180                 185                 190

Glu Asn Asn Tyr Lys Thr Thr Pro Pro Val Leu Asp Ser Asp Gly Ser
        195                 200                 205

Phe Phe Leu Tyr Ser Lys Leu Thr Val Asp Lys Ser Arg Trp Gln Gln
    210                 215                 220

Gly Asn Val Phe Ser Cys Ser Val Met His Glu Ala Leu His Asn His
225                 230                 235                 240

Tyr Thr Gln Lys Ser Leu Ser Leu Ser Pro Gly Lys Trp Gly Asn Leu
                245                 250                 255

Trp Val Thr Val Tyr Tyr Gly Val Pro Val Trp Lys Glu Ala Lys Thr
            260                 265                 270

Thr Leu Phe Cys Ala Ser Asp Ala Lys Ser Tyr Glu Lys Glu Val His
        275                 280                 285

Asn Val Trp Ala Thr His Ala Cys Val Pro Thr Asp Pro Asn Pro Gln
    290                 295                 300

Glu Ile Val Leu Gly Asn Val Thr Glu Asn Phe Asn Met Trp Lys Asn
305                 310                 315                 320

Asp Met Val Asp Gln Met His Glu Asp Ile Ile Ser Leu Trp Asp Gln
                325                 330                 335

Ser Leu Lys Pro Cys Val Lys Leu Thr Pro Leu Cys Val Thr Leu Asn
            340                 345                 350

Cys Thr Glu Val Asn Val Thr Arg Asn Val Asn Asn Ser Val Val Asn
```

355                 360                 365
Asn Thr Thr Asn Val Asn Asn Ser Met Asn Gly Asp Met Lys Asn Cys
        370                 375                 380

Ser Phe Asn Ile Thr Thr Glu Leu Lys Asp Lys Lys Asn Val Tyr
385                 390                 395                 400

Ala Leu Phe Tyr Lys Leu Asp Ile Val Ser Leu Asn Glu Thr Asp Asp
                405                 410                 415

Ser Glu Thr Gly Asn Ser Ser Lys Tyr Tyr Arg Leu Ile Asn Cys Asn
                420                 425                 430

Thr Ser Ala Leu Thr Gln Ala Cys Pro Lys Val Ser Phe Asp Pro Ile
                435                 440                 445

Pro Ile His Tyr Cys Ala Pro Ala Gly Tyr Ala Ile Leu Lys Cys Asn
                450                 455                 460

Asn Lys Thr Phe Asn Gly Thr Gly Pro Cys His Asn Val Ser Thr Val
465                 470                 475                 480

Gln Cys Thr His Gly Ile Lys Pro Val Val Ser Thr Gln Leu Leu Leu
                485                 490                 495

Asn Gly Ser Leu Ala Glu Glu Gly Ile Ile Ile Arg Ser Glu Asn Leu
                500                 505                 510

Thr Asn Asn Val Lys Thr Ile Ile Val His Leu Asn Arg Ser Ile Glu
                515                 520                 525

Ile Val Cys Val Arg Pro Asn Asn Asn Thr Arg Gln Ser Ile Arg Ile
530                 535                 540

Gly Pro Gly Gln Thr Phe Tyr Ala Thr Gly Asp Ile Ile Gly Asp Ile
545                 550                 555                 560

Arg Gln Ala His Cys Asn Ile Ser Arg Thr Asn Trp Thr Lys Thr Leu
                565                 570                 575

Arg Glu Val Arg Asn Lys Leu Arg Glu His Phe Pro Asn Lys Asn Ile
                580                 585                 590

Thr Phe Lys Pro Ser Ser Gly Gly Asp Leu Glu Ile Thr Thr His Ser
                595                 600                 605

Phe Asn Cys Arg Gly Glu Phe Phe Tyr Cys Asn Thr Ser Gly Leu Phe
                610                 615                 620

Ser Ile Asn Tyr Thr Glu Asn Asn Thr Asp Gly Thr Pro Ile Thr Leu
625                 630                 635                 640

Pro Cys Arg Ile Arg Gln Ile Ile Asn Met Trp Gln Glu Val Gly Arg
                645                 650                 655

Ala Met Tyr Ala Pro Pro Ile Glu Gly Asn Ile Ala Cys Lys Ser Asp
                660                 665                 670

Ile Thr Gly Leu Leu Leu Val Arg Asp Gly Gly Ser Thr Asn Asp Ser
                675                 680                 685

Thr Asn Asn Asn Thr Glu Ile Phe Arg Pro Ala Gly Gly Asp Met Arg
                690                 695                 700

Asp Asn Trp Arg Ser Glu Leu Tyr Lys Tyr Lys Val Val Glu Ile Lys
705                 710                 715                 720

Pro Leu Gly Ile Ala Pro Thr Glu Ala Lys Arg Arg Val Val Glu Arg
                725                 730                 735

Glu Lys Arg Ala Val Gly Ile Gly Ala Val Phe Leu Gly Phe Leu Gly
                740                 745                 750

Ala Ala Gly Ser Thr Met Gly Ala Ala Ser Ile Thr Leu Thr Ala Gln
                755                 760                 765

Ala Arg Gln Val Leu Ser Gly Ile Val Gln Gln Gln Ser Asn Leu Leu
                770                 775                 780

```
Arg Ala Ile Glu Ala Gln Gln His Leu Leu Gln Leu Thr Val Trp Gly
785                 790                 795                 800

Ile Lys Gln Leu Gln Thr Arg Val Leu Ala Ile Glu Arg Tyr Leu Lys
            805                 810                 815

Asp Gln Gln Leu Leu Met Lys Gln Ile Glu Asp Lys Ile Glu Glu Ile
        820                 825                 830

Leu Ser Lys Ile Tyr His Ile Glu Asn Glu Ile Ala Arg Ile Lys Lys
    835                 840                 845

Leu Ile Gly Glu Val Met Pro Ala Ser Ser Pro Gly His Met Gly Gly
850                 855                 860

Ser Val Arg Glu Pro Ala Leu Ser Val Ala Leu Trp Leu Ser Trp Gly
865                 870                 875                 880

Ala Val Leu Gly Ala Val Thr Cys Ala Val Ala Leu Leu Ile Gln Gln
                885                 890                 895

Thr Glu Leu Gln Ser Leu Arg Arg Glu Val Ser Arg Leu Gln Arg Ser
            900                 905                 910

Gly Gly Pro Ser Gln Lys Gln Gly Glu Arg Pro Trp Gln Ser Leu Trp
        915                 920                 925

Glu Gln Ser Pro Asp Val Leu Glu Ala Trp Lys Asp Gly Ala Lys Ser
    930                 935                 940

Arg Arg Arg Arg Ala Val Leu Thr Gln Lys His Lys Lys Lys His Ser
945                 950                 955                 960

Val Leu His Leu Val Pro Val Asn Ile Thr Ser Lys Asp Ser Asp Val
                965                 970                 975

Thr Glu Val Met Trp Gln Pro Val Leu Arg Arg Gly Arg Gly Leu Glu
            980                 985                 990

Ala Gln Gly Asp Ile Val Arg Val Trp Asp Thr Gly Ile Tyr Leu Leu
        995                 1000                1005

Tyr Ser Gln Val Leu Phe His Asp Val Thr Phe Thr Met Gly Gln
    1010                1015                1020

Val Val Ser Arg Glu Gly Gln Gly Arg Arg Glu Thr Leu Phe Arg
    1025                1030                1035

Cys Ile Arg Ser Met Pro Ser Asp Pro Asp Arg Ala Tyr Asn Ser
    1040                1045                1050

Cys Tyr Ser Ala Gly Val Phe His Leu His Gln Gly Asp Ile Ile
    1055                1060                1065

Thr Val Lys Ile Pro Arg Ala Asn Ala Lys Leu Ser Leu Ser Pro
    1070                1075                1080

His Gly Thr Phe Leu Gly Phe Val Lys Leu
    1085                1090

<210> SEQ ID NO 9
<211> LENGTH: 2769
<212> TYPE: DNA
<213> ORGANISM: Artificial Sequence
<220> FEATURE:
<223> OTHER INFORMATION: Fusion protein

<400> SEQUENCE: 9
atgctgctct tcctcctctc tgcactggtc ctactcacac agcccctggg ctacctggaa      60
gcagaaatga agacctactc ccacagaaca acgcccagtg cttgcaccct ggtcatgtgt     120
agctcagtgg agagtggcct gcctggtcgc gatggacggg atgggagaga ggccctcgg      180 ggcgagaagg gggacccagg tttgccagga gctgcagggc aagcagggat gcctggacaa     240
```

```
gctggcccag ttgggcccaa aggggacaat ggctctgttg gagaacctgg accaaaggga        300
gacactgggc caagtatggc gtctcaaggc accaaacgat cttacgaaca gatggagact        360
gatggagaac gccagaatgc cactgaaatc agagcatccg tcggaaaaat gattggtgga        420
attggacgat tctacatcca aatgtgcacc gaactcaaac tcagtgatta tgagggacgg        480
ttgatccaaa acagcttaac aatagagaga atggtgctct ctgcttttga cgaaaggaga        540
aataaatacc ttgaagaaca tcccagtgcg ggaaaagatc ctaagaaaac tggaggacct        600
atatacagga gagtaaacgg aaagtggatg agagaactca tcctttatga caagaagaa         660 ataaggcgaa tctggcgcca agctaataat ggtgacgatg caacggctgg tctgactcac        720
atgatgatct ggcattccaa tttgaatgat gcaacttatc agaggacaag agctcttgtt        780
cgcaccggaa tggatcccag gatgtgctct ctgatgcaag gttcaactct ccctaggagg        840
tctggagccg caggtgctgc agtcaaagga gttggaacaa tggtgatgga attggtcaga        900
atgatcaaac gtgggatcaa tgatcggaac ttctggaggg gtgagaatgg acgaaaaaca        960
agaattgctt atgaaagaat gtgcaacatt ctcaaaggga aatttcaaac tgctgcacaa       1020
aaagcaatga tggatcaagt gagagagagc cggaacccag ggaatgctga gttcgaagat       1080 ctcactttc tagcacggtc tgcactcata ttgagagggt cggttgctca caagtcctgc         1140
ctgcctgcct gtgtgtatgg gcctgccgta gccagtgggt acgactttga aggagggga         1200 tactctctag tcggaataga cccttttcaga ctgcttcaaa acagccaagt gtacagccta      1260
atcagaccaa atgagaatcc agcacacaag agtcaactgg tgtggatggc atgccattct        1320
gccgcatttg aagatctaag agtattaagc ttcatcaaag gacgaaggt gctcccaaga         1380 gggaagcttt ccactagagg agttcaaatt gcttccaatg aaaatatgga gactatggaa        1440
tcaagtacac ttgaactgag aagcaggtac tgggccataa ggaccagaag tggaggaaac        1500
accaatcaac agagggcatc tgcgggccaa atcagcatac aacctacgtt ctcagtacag        1560
agaaatctcc cttttgacag aacaaccatt atggcagcat tcaatgggaa tacagagggg        1620
agaacatctg acatgaggac cgaaatcata aggatgatgg aaagtgcaag accagaagat        1680
gtgtctttcc aggggcgggg agtcttcgag ctctcggacg aaaaggcagc gagcccgatc        1740
gtgccttcct ttgacatgag taatgaagga tcttatttct tcggagacaa tgcagaggag        1800
tacgacaatg gacctccagg acctcccggt gtgcctggtc cagctggaag agaaggtccc       1860
ctggggaagc aggggaacat aggacctcag ggcaagccag gcccaaaagg agaagctggg        1920
cccaaaggag aagtaggtgc cccaggcatg cagggctcgg caggggcaag aggcctcgca       1980
ggccctaagg gagagcgagg tgtccctggt gagcgtggag tccctggaaa cacaggggca       2040
gcagggtctg ctggagccat gggtcccag ggaagtccag gtgccagggg accccggga         2100 ttgaaggggg acaaaggcat tcctggagac aaaggagcaa agggagaaag tgggcttcca       2160
gatgttgctt ctctgaggca gcaggttgag gccttacagg acaagtaca gcacctccag         2220 gctgctttct ctcagtataa gaaagttgag ctcttcccaa atggccaaag tgtcgggag        2280 aagattttca agacagcagg ctttgtaaaa ccatttacgg aggcacaggg tgatcagaat        2340
cctcaaattg cggcacatgt cataagtgag gccagcagta aaacaacatc tgtgttacag        2400
tgggctgaaa aaggatacta caccatgagc aacaacttgg taaccctgga aaatgggaaa        2460
cagctgaccg ttaaaagaca aggactctat tatatctatg cccaagtcac cttctgttcc        2520
aatcgggaag cttcgagtca agctccattt atagccagcc tctgcctaaa gtcccccggt        2580
agattcgaga gaatcttact cagagctgca aatacccaca gttccgccaa accttgcggg        2640
```

-continued

```
caacaatcca ttcacttggg aggagtattt gaattgcaac caggtgcttc ggtgtttgtc    2700
aatgtgactg atccaagcca agtgagccat ggcactggct tcacgtcctt tggcttactc    2760
aaactctga                                                              2769
```

<210> SEQ ID NO 10
<211> LENGTH: 922
<212> TYPE: PRT
<213> ORGANISM: Artificial Sequence
<220> FEATURE:
<223> OTHER INFORMATION: Fusion protein construct

<400> SEQUENCE: 10

```
Met Leu Leu Phe Leu Leu Ser Ala Leu Val Leu Leu Thr Gln Pro Leu
1               5                   10                  15

Gly Tyr Leu Glu Ala Glu Met Lys Thr Tyr Ser His Arg Thr Thr Pro
            20                  25                  30

Ser Ala Cys Thr Leu Val Met Cys Ser Ser Val Glu Ser Gly Leu Pro
        35                  40                  45

Gly Arg Asp Gly Arg Asp Gly Arg Glu Gly Pro Arg Gly Glu Lys Gly
    50                  55                  60

Asp Pro Gly Leu Pro Gly Ala Ala Gly Gln Ala Gly Met Pro Gly Gln
65                  70                  75                  80

Ala Gly Pro Val Gly Pro Lys Gly Asp Asn Gly Ser Val Gly Glu Pro
                85                  90                  95

Gly Pro Lys Gly Asp Thr Gly Pro Ser Met Ala Ser Gln Gly Thr Lys
            100                 105                 110

Arg Ser Tyr Glu Gln Met Glu Thr Asp Gly Glu Arg Gln Asn Ala Thr
        115                 120                 125

Glu Ile Arg Ala Ser Val Gly Lys Met Ile Gly Ile Gly Arg Phe
    130                 135                 140

Tyr Ile Gln Met Cys Thr Glu Leu Lys Leu Ser Asp Tyr Glu Gly Arg
145                 150                 155                 160

Leu Ile Gln Asn Ser Leu Thr Ile Glu Arg Met Val Leu Ser Ala Phe
                165                 170                 175

Asp Glu Arg Arg Asn Lys Tyr Leu Glu Glu His Pro Ser Ala Gly Lys
            180                 185                 190

Asp Pro Lys Lys Thr Gly Gly Pro Ile Tyr Arg Arg Val Asn Gly Lys
        195                 200                 205

Trp Met Arg Glu Leu Ile Leu Tyr Asp Lys Glu Glu Ile Arg Arg Ile
    210                 215                 220

Trp Arg Gln Ala Asn Asn Gly Asp Asp Ala Thr Ala Gly Leu Thr His
225                 230                 235                 240

Met Met Ile Trp His Ser Asn Leu Asn Asp Ala Thr Tyr Gln Arg Thr
                245                 250                 255

Arg Ala Leu Val Arg Thr Gly Met Asp Pro Arg Met Cys Ser Leu Met
            260                 265                 270

Gln Gly Ser Thr Leu Pro Arg Arg Ser Gly Ala Ala Gly Ala Ala Val
        275                 280                 285

Lys Gly Val Gly Thr Met Val Met Glu Leu Val Arg Met Ile Lys Arg
    290                 295                 300

Gly Ile Asn Asp Arg Asn Phe Trp Arg Gly Glu Asn Gly Arg Lys Thr
305                 310                 315                 320

Arg Ile Ala Tyr Glu Arg Met Cys Asn Ile Leu Lys Gly Lys Phe Gln
                325                 330                 335
```

-continued

```
Thr Ala Ala Gln Lys Ala Met Met Asp Gln Val Arg Glu Ser Arg Asn
            340                 345                 350
Pro Gly Asn Ala Glu Phe Glu Asp Leu Thr Phe Leu Ala Arg Ser Ala
            355                 360                 365
Leu Ile Leu Arg Gly Ser Val Ala His Lys Ser Cys Leu Pro Ala Cys
370                 375                 380
Val Tyr Gly Pro Ala Val Ala Ser Gly Tyr Asp Phe Glu Arg Glu Gly
385                 390                 395                 400
Tyr Ser Leu Val Gly Ile Asp Pro Phe Arg Leu Leu Gln Asn Ser Gln
                405                 410                 415
Val Tyr Ser Leu Ile Arg Pro Asn Glu Asn Pro Ala His Lys Ser Gln
            420                 425                 430
Leu Val Trp Met Ala Cys His Ser Ala Ala Phe Glu Asp Leu Arg Val
            435                 440                 445
Leu Ser Phe Ile Lys Gly Thr Lys Val Leu Pro Arg Gly Lys Leu Ser
450                 455                 460
Thr Arg Gly Val Gln Ile Ala Ser Asn Glu Asn Met Glu Thr Met Glu
465                 470                 475                 480
Ser Ser Thr Leu Glu Leu Arg Ser Arg Tyr Trp Ala Ile Arg Thr Arg
                485                 490                 495
Ser Gly Gly Asn Thr Asn Gln Gln Arg Ala Ser Ala Gly Gln Ile Ser
            500                 505                 510
Ile Gln Pro Thr Phe Ser Val Gln Arg Asn Leu Pro Phe Asp Arg Thr
            515                 520                 525
Thr Ile Met Ala Ala Phe Asn Gly Asn Thr Glu Gly Arg Thr Ser Asp
530                 535                 540
Met Arg Thr Glu Ile Ile Arg Met Met Glu Ser Ala Arg Pro Glu Asp
545                 550                 555                 560
Val Ser Phe Gln Gly Arg Gly Val Phe Glu Leu Ser Asp Glu Lys Ala
                565                 570                 575
Ala Ser Pro Ile Val Pro Ser Phe Asp Met Ser Asn Glu Gly Ser Tyr
            580                 585                 590
Phe Phe Gly Asp Asn Ala Glu Glu Tyr Asp Asn Gly Pro Pro Gly Pro
            595                 600                 605
Pro Gly Val Pro Gly Pro Ala Gly Arg Glu Gly Pro Leu Gly Lys Gln
610                 615                 620
Gly Asn Ile Gly Pro Gln Gly Lys Pro Gly Pro Lys Gly Glu Ala Gly
625                 630                 635                 640
Pro Lys Gly Glu Val Gly Ala Pro Gly Met Gln Gly Ser Ala Gly Ala
                645                 650                 655
Arg Gly Leu Ala Gly Pro Lys Gly Glu Arg Gly Val Pro Gly Glu Arg
            660                 665                 670
Gly Val Pro Gly Asn Thr Gly Ala Ala Gly Ser Ala Gly Ala Met Gly
            675                 680                 685
Pro Gln Gly Ser Pro Gly Ala Arg Gly Pro Pro Gly Leu Lys Gly Asp
690                 695                 700
Lys Gly Ile Pro Gly Asp Lys Gly Ala Lys Gly Glu Ser Gly Leu Pro
705                 710                 715                 720
Asp Val Ala Ser Leu Arg Gln Gln Val Glu Ala Leu Gln Gly Gln Val
                725                 730                 735
Gln His Leu Gln Ala Ala Phe Ser Gln Tyr Lys Lys Val Glu Leu Phe
            740                 745                 750
```

```
Pro Asn Gly Gln Ser Val Gly Glu Lys Ile Phe Lys Thr Ala Gly Phe
            755                 760                 765

Val Lys Pro Phe Thr Glu Ala Gln Gly Asp Gln Asn Pro Gln Ile Ala
    770                 775                 780

Ala His Val Ile Ser Glu Ala Ser Ser Lys Thr Thr Ser Val Leu Gln
785                 790                 795                 800

Trp Ala Glu Lys Gly Tyr Tyr Thr Met Ser Asn Asn Leu Val Thr Leu
                805                 810                 815

Glu Asn Gly Lys Gln Leu Thr Val Lys Arg Gln Gly Leu Tyr Tyr Ile
            820                 825                 830

Tyr Ala Gln Val Thr Phe Cys Ser Asn Arg Glu Ala Ser Ser Gln Ala
            835                 840                 845

Pro Phe Ile Ala Ser Leu Cys Leu Lys Ser Pro Gly Arg Phe Glu Arg
850                 855                 860

Ile Leu Leu Arg Ala Ala Asn Thr His Ser Ser Ala Lys Pro Cys Gly
865                 870                 875                 880

Gln Gln Ser Ile His Leu Gly Gly Val Phe Glu Leu Gln Pro Gly Ala
                885                 890                 895

Ser Val Phe Val Asn Val Thr Asp Pro Ser Gln Val Ser His Gly Thr
            900                 905                 910

Gly Phe Thr Ser Phe Gly Leu Leu Lys Leu
            915                 920

<210> SEQ ID NO 11
<211> LENGTH: 1929
<212> TYPE: DNA
<213> ORGANISM: Artificial Sequence
<220> FEATURE:
<223> OTHER INFORMATION: Fusion protein

<400> SEQUENCE: 11
atggatgcaa tgaagagagg gctctgctgt gtgctgctgc tgtgtggagc agtcttcgtt      60
tcgcccagcg aagatgacgt tactacaact gaagagctag ctcctgcttt ggtccctcca     120
cccaagggaa cttgtgcagg ttggatggca ggcatcccag acatcctgg  ccacaatggc     180 acaccaggcc gtgatggcaa aatatacaat cgaaatatag tcaacagatt acttggcgat     240
gctctcaacg gaaaaccaga agaaaaaaaa gatgatcccc aaaagatgg  caacaaagat     300 gatcttccaa agaagaaaaa aaagatgat  cttccaaaag aagaaaaaaa agatgatccc     360
ccaaaagatc taaaaaaga  tgatccacca aaagaggctc aaaataaatt gaatcaacca     420
gtagtggcag atgaaaatgt agatcaaggg ccaggagcac acaagggcc  aggagcacca     480 caaggaccag gagcaccaca gggtccagga gcaccacaag gaccaggagc accacaagga     540
ccaggagcac acaaggtcc  aggagcacca cagggtccag gagcaccaca gggtccagga     600
gcaccacaag gaccaggagc accacagggg ccaggagcac acaaggacc  aggagcacca     660 caaggaccag gagcaccaca ggggccagga gcaccacaag gccaggagc  accacaagaa     720 ccacccc aac aaccacccca caaccacca  caacagccac acaacagcc  accacaacag     780 ccaccacaac agccaccaca caaccacgc  ccacagccag atggtaataa caacaataac     840
aataataatg gtaataataa tgaagattct tatgtcccaa gcgcggaaca atactagaa      900 tttgttaaac agataagtag tcaactcaca gaggaatggt ctcaatgtag tgtaacctgt     960
ggttctggtg taagagttag aaaacgaaaa aatgtaaaca agcaaccaga aaatttgacc    1020
ttagaggata ttgatactga aatttgtaaa atggataaat gttcaagtat atttaatatt    1080
```

-continued

```
gtaagcaatt cattaggatt tgtaatatta ttagtattag tattctttaa tagagatggc    1140
actcctggag agaagggaga gaaaggagat gcaggtcttc ttggtcctaa gggtgagaca    1200
ggagatgttg gaatgacagg agctgaaggg ccacggggct tccccggaac ccctggcagg    1260
aaaggagagc ctggagaagc cgctcataga agattggata aggtcgaaga ggaagtaaac    1320
cttcatgaag attttgtatt cataaaaaag ctaaagagat gcaacaaagg agaaggatct    1380
ttatccttgc tgaactgtga ggagatgaga aggcaatttg aagaccttgt caaggatata    1440
acgttaaaca aagaagagaa aaaagaaaac agctttgaaa tgcaaagagg tgatgaggat    1500
cctcaaattg cagcacacgt tgtaagcgaa gccaacagta atgcagcatc cgttctacag    1560
tgggccaaga aaggatatta taccatgaaa agcaacttgg taatgcttga aaatgggaaa    1620
cagctgacgg ttaaaagaga aggactctat tatgtctaca ctcaagtcac cttctgctct    1680
aatcgggagc cttcgagtca acgcccattc atcgtcggcc tctggctgaa gcccagcatt    1740
ggatctgaga gaatcttact caaggcggca aatacccaca gttcctccca gctttgcgag    1800
cagcagtctg ttcacttggg cggagtgttt gaattacaag ctggtgcttc tgtgtttgtc    1860
aacgtgactg aagcaagcca agtgatccac agagttggct tctcatcttt tggcttactc    1920
aaactctga                                                           1929
```

<210> SEQ ID NO 12
<211> LENGTH: 642
<212> TYPE: PRT
<213> ORGANISM: Artificial Sequence
<220> FEATURE:
<223> OTHER INFORMATION: Fusion protein

<400> SEQUENCE: 12

```
Met Asp Ala Met Lys Arg Gly Leu Cys Cys Val Leu Leu Cys Gly
 1               5                  10                  15

Ala Val Phe Val Ser Pro Ser Glu Asp Val Thr Thr Thr Glu Glu
                20                  25                  30

Leu Ala Pro Ala Leu Val Pro Pro Lys Gly Thr Cys Ala Gly Trp
                35                  40                  45

Met Ala Gly Ile Pro Gly His Pro Gly His Asn Gly Thr Pro Gly
    50                  55                  60

Asp Gly Lys Ile Tyr Asn Arg Asn Ile Val Asn Arg Leu Leu Gly Asp
 65                  70                  75                  80

Ala Leu Asn Gly Lys Pro Glu Glu Lys Lys Asp Asp Pro Lys Asp
                85                  90                  95

Gly Asn Lys Asp Asp Leu Pro Lys Glu Lys Lys Asp Asp Leu Pro
                100                 105                 110

Lys Glu Glu Lys Lys Asp Asp Pro Lys Asp Pro Lys Lys Asp Asp
                115                 120                 125

Pro Pro Lys Glu Ala Gln Asn Lys Leu Asn Gln Pro Val Val Ala Asp
    130                 135                 140

Glu Asn Val Asp Gln Gly Pro Gly Ala Pro Gln Gly Pro Gly Ala Pro
145                 150                 155                 160

Gln Gly Pro Gly Ala Pro Gln Gly Pro Gly Ala Pro Gln Gly Pro Gly
                165                 170                 175

Ala Pro Gln Gly Pro Gly Ala Pro Gln Gly Pro Gly Ala Pro Gln Gly
                180                 185                 190

Pro Gly Ala Pro Gln Gly Pro Gly Ala Pro Gln Gly Pro Gly Ala Pro
                195                 200                 205
```

```
Gln Gly Pro Gly Ala Pro Gln Gly Pro Gly Ala Pro Gln Gly Pro Gly
    210                 215                 220

Ala Pro Gln Gly Pro Gly Ala Pro Gln Gly Pro Gly Ala Pro Gln Glu
225                 230                 235                 240

Pro Pro Gln Gln Pro Pro Gln Gln Pro Pro Gln Gln Pro Pro Gln Gln
                245                 250                 255

Pro Pro Gln Gln Pro Pro Gln Gln Pro Pro Gln Gln Pro Arg Pro Gln
                260                 265                 270

Pro Asp Gly Asn Asn Asn Asn Asn Asn Gly Asn Asn Asn Glu
            275                 280                 285

Asp Ser Tyr Val Pro Ser Ala Glu Gln Ile Leu Glu Phe Val Lys Gln
        290                 295                 300

Ile Ser Ser Gln Leu Thr Glu Glu Trp Ser Gln Cys Ser Val Thr Cys
305                 310                 315                 320

Gly Ser Gly Val Arg Val Arg Lys Arg Lys Asn Val Asn Lys Gln Pro
                325                 330                 335

Glu Asn Leu Thr Leu Glu Asp Ile Asp Thr Glu Ile Cys Lys Met Asp
                340                 345                 350

Lys Cys Ser Ser Ile Phe Asn Ile Val Ser Asn Ser Leu Gly Phe Val
        355                 360                 365

Ile Leu Leu Val Leu Val Phe Phe Asn Arg Asp Gly Thr Pro Gly Glu
370                 375                 380

Lys Gly Glu Lys Gly Asp Ala Gly Leu Leu Gly Pro Lys Gly Glu Thr
385                 390                 395                 400

Gly Asp Val Gly Met Thr Gly Ala Glu Gly Pro Arg Gly Phe Pro Gly
                405                 410                 415

Thr Pro Gly Arg Lys Gly Glu Pro Gly Glu Ala Ala His Arg Arg Leu
                420                 425                 430

Asp Lys Val Glu Glu Val Asn Leu His Glu Asp Phe Val Phe Ile
        435                 440                 445

Lys Lys Leu Lys Arg Cys Asn Lys Gly Glu Gly Ser Leu Ser Leu Leu
        450                 455                 460

Asn Cys Glu Glu Met Arg Arg Gln Phe Glu Asp Leu Val Lys Asp Ile
465                 470                 475                 480

Thr Leu Asn Lys Glu Glu Lys Lys Glu Asn Ser Phe Glu Met Gln Arg
                485                 490                 495

Gly Asp Glu Asp Pro Gln Ile Ala Ala His Val Val Ser Glu Ala Asn
                500                 505                 510

Ser Asn Ala Ala Ser Val Leu Gln Trp Ala Lys Lys Gly Tyr Tyr Thr
        515                 520                 525

Met Lys Ser Asn Leu Val Met Leu Glu Asn Gly Lys Gln Leu Thr Val
        530                 535                 540

Lys Arg Glu Gly Leu Tyr Tyr Val Tyr Thr Gln Val Thr Phe Cys Ser
545                 550                 555                 560

Asn Arg Glu Pro Ser Ser Gln Arg Pro Phe Ile Val Gly Leu Trp Leu
                565                 570                 575

Lys Pro Ser Ile Gly Ser Glu Arg Ile Leu Leu Lys Ala Ala Asn Thr
            580                 585                 590

His Ser Ser Ser Gln Leu Cys Glu Gln Gln Ser Val His Leu Gly Gly
            595                 600                 605

Val Phe Glu Leu Gln Ala Gly Ala Ser Val Phe Val Asn Val Thr Glu
        610                 615                 620

Ala Ser Gln Val Ile His Arg Val Gly Phe Ser Ser Phe Gly Leu Leu
```

| | | | | |
|---|---|---|---|---|
| 625 | 630 | 635 | 640 | |

Lys Leu

<210> SEQ ID NO 13
<211> LENGTH: 3006
<212> TYPE: DNA
<213> ORGANISM: Artificial Sequence
<220> FEATURE:
<223> OTHER INFORMATION: Fusion protein

<400> SEQUENCE: 13

| | |
|---|---|
| atgctgccct ttctctccat gcttgtcttg cttgtacagc ccctgggaaa tctgggagca | 60 |
| gaaatgaaga gcctctcgca gagatcagta cccaacacct gcaccctagt catgtgtagc | 120 |
| ccaacagaga atggcctgcc tggtcgtgat ggacgggatg ggagagaagg tccacggggt | 180 |
| gagaagggtg atccaggttt gccaggacct atggggctct cagggttgca gggccctaca | 240 |
| ggtccagttg gacccaaagg agagaatggc tctgctggcg aacctggacc aaagggagaa | 300 |
| cgtggactaa gtgacctcc aggacttcca gtattcctg tccaatggg agccaggcc | 360 |
| agcgtgctgt ctggggcga gctggacagg tgggagaaga ttaggctgag gcccggagga | 420 |
| aagaagaagt acaaactgaa acacatcgtg tgggcctccc gggagctgga acggttcgcc | 480 |
| gtgaatcctg gctgctgga cctctgag ggctgcagac agatcctggg acagctgcag | 540 |
| cctagcctgc agaccggaag cgaggagctg aggtctctgt acaacaccgt ggccacactg | 600 |
| tactgcgtgc accagcggat tgaggtgaag gataccaagg aagccctgga aagattgag | 660 |
| gaagagcaga taagtccaa gaagaaagcc cagcaggccg ccgccgacac aggaaatagc | 720 |
| tcccaggtgt ctcagaacta ccccatcgtg cagaacctgc agggacagat ggtgcaccag | 780 |
| gccatcagcc ccggaccct gaacgcctgg gtgaaggtgg tggaagagaa agccttcagc | 840 |
| ccagaagtga tccccatgtt cagcgccctg agcgagggg ccaccccaca ggacctgaat | 900 |
| acaatgctga atacagtggg cggccaccag gccgccatgc agatgctgaa ggagaccatt | 960 |
| aacgaggagg ccgccgagtg ggataggctg cacccagtgc acgccgggcc catcgcccca | 1020 |
| ggcagatga gggagccacg gggctctgac atcgccggca ccacctctac cctgcaggag | 1080 |
| cagatcggct ggatgaccaa taccccacct attcccgtgg agaaatcta caaaaggtgg | 1140 |
| attatcctgg gctgaacaa gatcgtgaga atgtactccc caacatccat tctgacatc | 1200 |
| cggcagggcc caaaggaacc ctttagagac tacgtggata ggttctacaa aaccctgcgc | 1260 |
| gccgagcagg cctcccagga ggtgaagaac tggatgaccg agacactgct ggtgcagaat | 1320 |
| gccaacccag actgtaagac cattctgaag gccctggaca gccgccac cctggaggaa | 1380 |
| atgatgacag cctgccaggg ggtgggcgga cccggccaca aggcccgcgt gctgccgag | 1440 |
| gccatgtccc aggtgacaaa tccgccacc atcatgatgc agcgcggaaa ttttcggaat | 1500 |
| cagcgcaaaa cagtgaaatg cttcaattgc gggaaggagg ccacatcgc aagaattgc | 1560 |
| agagccccaa ggaagaaggg ctgctggaag tgcggaaagg agggccacca gatgaaggac | 1620 |
| tgcacagagc gccaggccaa tttcctgggc aagatctggc catcccacaa ggggcggcct | 1680 |
| ggaaacttcc tgcagagccg gcccgaaccc acagccccc ctgaagaatc cttccggttc | 1740 |
| ggagaggaaa caaccacacc cagccagaag caggagccta tcgacaagga actgtaccca | 1800 |
| ctggccagcc tgagaagcct gttcggcaac gatccaagca gccaggctgg gaaagaaggt | 1860 |
| ccctctggga gcagggggaa catagggcct caaggcaaac aggtcctaa aggagaggct | 1920 |
| gggcccaaag gagaagtagg tgctcctggc atgcaaggat ctacaggggc aaaaggctcc | 1980 |

```
acaggcccca agggagaaag aggtgcccct ggtgtgcaag gagccccagg gaatgctgga    2040
gcagcaggac ctgccggacc tgccggtcca cagggagctc caggttccag ggggccccca    2100
ggactcaagg gggacagagg tgttcctgga cagaggaa tcaaggtga aagcgggctt       2160 ccagacagtg ctgctctgag gcagcagatg gaggccttaa aaggaaaact acagcgtcta    2220
gaggttgcct tctcccacta tcagaaagct gcattgttcc ctgatggccg agcgcagatg    2280
gatcctaaca gaatatcaga agacagcact cactgctttt atagaatcct gagactccat    2340
gaaaacgcag atttgcagga ctcgactctg gagagtgaag acacactacc tgactcctgc    2400
aggaggatga aacaagcctt tcaggggggcc gtgcagaagg aactgcaaca cattgtgggg   2460
ccacagcgct tctcaggagc tccagctatg atggaaggct catggttgga tgtggcccag    2520
cgaggcaagc ctgaggccca gccatttgca caccttcacca tcaatgctgc cagcatccca   2580
tcgggttccc ataaagtcac tctgtcctct tggtaccacg atcgaggctg ggccaagatc    2640
tctaacatga cgttaagcaa cggaaaacta agggttaacc aagatggctt ctattacctg    2700
tacgccaaca tttgctttcg gcatcatgaa acatcgggaa gcgtacctac agactatctt    2760
cagctgatgg tgtatgtcgt taaaaccagc atcaaaatcc caagttctca taacctgatg    2820
aaaggaggga gcacgaaaaa ctggtcgggc aattctgaat tccactttta ttccataaat    2880
gttgggggat ttttcaagct ccgagctggt gaagaaatta gcattcaggt gtccaacccct   2940 tccctgctgg atccggatca agatgcgacg tactttgggg ctttcaaagt tcaggacata    3000
gactga                                                               3006
```

<210> SEQ ID NO 14
<211> LENGTH: 1001
<212> TYPE: PRT
<213> ORGANISM: Artificial Sequence
<220> FEATURE:
<223> OTHER INFORMATION: Fusion protein

<400> SEQUENCE: 14

```
Met Leu Pro Phe Leu Ser Met Leu Val Leu Val Gln Pro Leu Gly
1               5                  10                  15

Asn Leu Gly Ala Glu Met Lys Ser Leu Ser Gln Arg Ser Val Pro Asn
            20                  25                  30

Thr Cys Thr Leu Val Met Cys Ser Pro Thr Glu Asn Gly Leu Pro Gly
        35                  40                  45

Arg Asp Gly Arg Asp Gly Arg Glu Gly Pro Arg Gly Glu Lys Gly Asp
    50                  55                  60

Pro Gly Leu Pro Gly Pro Met Gly Leu Ser Gly Leu Gln Gly Pro Thr
65                  70                  75                  80

Gly Pro Val Gly Pro Lys Gly Glu Asn Gly Ser Ala Gly Glu Pro Gly
                85                  90                  95

Pro Lys Gly Glu Arg Gly Leu Ser Gly Pro Gly Leu Pro Gly Ile
            100                 105                 110

Pro Gly Pro Met Gly Ala Arg Ala Ser Val Leu Ser Gly Gly Glu Leu
        115                 120                 125

Asp Arg Trp Glu Lys Ile Arg Leu Arg Pro Gly Gly Lys Lys Lys Tyr
    130                 135                 140

Lys Leu Lys His Ile Val Trp Ala Ser Arg Glu Leu Glu Arg Phe Ala
145                 150                 155                 160

Val Asn Pro Gly Leu Leu Glu Thr Ser Glu Gly Cys Arg Gln Ile Leu
                165                 170                 175
```

```
Gly Gln Leu Gln Pro Ser Leu Gln Thr Gly Ser Glu Leu Arg Ser
            180                 185                 190

Leu Tyr Asn Thr Val Ala Thr Leu Tyr Cys Val His Gln Arg Ile Glu
            195                 200                 205

Val Lys Asp Thr Lys Glu Ala Leu Glu Lys Ile Glu Glu Glu Gln Asn
210                 215                 220

Lys Ser Lys Lys Ala Gln Gln Ala Ala Ala Asp Thr Gly Asn Ser
225                 230                 235                 240

Ser Gln Val Ser Gln Asn Tyr Pro Ile Val Gln Asn Leu Gln Gly Gln
            245                 250                 255

Met Val His Gln Ala Ile Ser Pro Arg Thr Leu Asn Ala Trp Val Lys
            260                 265                 270

Val Val Glu Glu Lys Ala Phe Ser Pro Glu Val Ile Pro Met Phe Ser
            275                 280                 285

Ala Leu Ser Glu Gly Ala Thr Pro Gln Asp Leu Asn Thr Met Leu Asn
            290                 295                 300

Thr Val Gly Gly His Gln Ala Ala Met Gln Met Leu Lys Glu Thr Ile
305                 310                 315                 320

Asn Glu Glu Ala Ala Glu Trp Asp Arg Leu His Pro Val His Ala Gly
                325                 330                 335

Pro Ile Ala Pro Gly Gln Met Arg Glu Pro Arg Gly Ser Asp Ile Ala
            340                 345                 350

Gly Thr Thr Ser Thr Leu Gln Glu Gln Ile Gly Trp Met Thr Asn Asn
            355                 360                 365

Pro Pro Ile Pro Val Gly Glu Ile Tyr Lys Arg Trp Ile Ile Leu Gly
            370                 375                 380

Leu Asn Lys Ile Val Arg Met Tyr Ser Pro Thr Ser Ile Leu Asp Ile
385                 390                 395                 400

Arg Gln Gly Pro Lys Glu Pro Phe Arg Asp Tyr Val Asp Arg Phe Tyr
                405                 410                 415

Lys Thr Leu Arg Ala Glu Gln Ala Ser Gln Glu Val Lys Asn Trp Met
            420                 425                 430

Thr Glu Thr Leu Leu Val Gln Asn Ala Asn Pro Asp Cys Lys Thr Ile
            435                 440                 445

Leu Lys Ala Leu Gly Pro Ala Ala Thr Leu Glu Glu Met Met Thr Ala
450                 455                 460

Cys Gln Gly Val Gly Gly Pro Gly His Lys Ala Arg Val Leu Ala Glu
465                 470                 475                 480

Ala Met Ser Gln Val Thr Asn Ser Ala Thr Ile Met Met Gln Arg Gly
                485                 490                 495

Asn Phe Arg Asn Gln Arg Lys Thr Val Lys Cys Phe Asn Cys Gly Lys
            500                 505                 510

Glu Gly His Ile Ala Lys Asn Cys Arg Ala Pro Arg Lys Lys Gly Cys
            515                 520                 525

Trp Lys Cys Gly Lys Glu Gly His Gln Met Lys Asp Cys Thr Glu Arg
            530                 535                 540

Gln Ala Asn Phe Leu Gly Lys Ile Trp Pro Ser His Lys Gly Arg Pro
545                 550                 555                 560

Gly Asn Phe Leu Gln Ser Arg Pro Glu Pro Thr Ala Pro Pro Glu Glu
                565                 570                 575

Ser Phe Arg Phe Gly Glu Glu Thr Thr Thr Pro Ser Gln Lys Gln Glu
            580                 585                 590
```

-continued

```
Pro Ile Asp Lys Glu Leu Tyr Pro Leu Ala Ser Leu Arg Ser Leu Phe
        595                 600                 605

Gly Asn Asp Pro Ser Ser Gln Ala Gly Lys Glu Gly Pro Ser Gly Lys
610                 615                 620

Gln Gly Asn Ile Gly Pro Gln Gly Lys Pro Gly Pro Lys Gly Glu Ala
625                 630                 635                 640

Gly Pro Lys Gly Glu Val Gly Ala Pro Gly Met Gln Gly Ser Thr Gly
                645                 650                 655

Ala Lys Gly Ser Thr Gly Pro Lys Gly Glu Arg Gly Ala Pro Gly Val
                660                 665                 670

Gln Gly Ala Pro Gly Asn Ala Gly Ala Gly Pro Ala Gly Pro Ala
                675                 680                 685

Gly Pro Gln Gly Ala Pro Gly Ser Arg Gly Pro Pro Gly Leu Lys Gly
        690                 695                 700

Asp Arg Gly Val Pro Gly Asp Arg Gly Ile Lys Gly Glu Ser Gly Leu
705                 710                 715                 720

Pro Asp Ser Ala Ala Leu Arg Gln Gln Met Glu Ala Leu Lys Gly Lys
                725                 730                 735

Leu Gln Arg Leu Glu Val Ala Phe Ser His Tyr Gln Lys Ala Ala Leu
            740                 745                 750

Phe Pro Asp Gly Arg Ala Gln Met Asp Pro Asn Arg Ile Ser Glu Asp
        755                 760                 765

Ser Thr His Cys Phe Tyr Arg Ile Leu Arg Leu His Glu Asn Ala Asp
        770                 775                 780

Leu Gln Asp Ser Thr Leu Glu Ser Glu Asp Thr Leu Pro Asp Ser Cys
785                 790                 795                 800

Arg Arg Met Lys Gln Ala Phe Gln Gly Ala Val Gln Lys Glu Leu Gln
                805                 810                 815

His Ile Val Gly Pro Gln Arg Phe Ser Gly Ala Pro Ala Met Met Glu
            820                 825                 830

Gly Ser Trp Leu Asp Val Ala Gln Arg Gly Lys Pro Glu Ala Gln Pro
        835                 840                 845

Phe Ala His Leu Thr Ile Asn Ala Ala Ser Ile Pro Ser Gly Ser His
    850                 855                 860

Lys Val Thr Leu Ser Ser Trp Tyr His Asp Arg Gly Trp Ala Lys Ile
865                 870                 875                 880

Ser Asn Met Thr Leu Ser Asn Gly Lys Leu Arg Val Asn Gln Asp Gly
                885                 890                 895

Phe Tyr Tyr Leu Tyr Ala Asn Ile Cys Phe Arg His His Glu Thr Ser
            900                 905                 910

Gly Ser Val Pro Thr Asp Tyr Leu Gln Leu Met Val Tyr Val Val Lys
        915                 920                 925

Thr Ser Ile Lys Ile Pro Ser Ser His Asn Leu Met Lys Gly Gly Ser
    930                 935                 940

Thr Lys Asn Trp Ser Gly Asn Ser Glu Phe His Phe Tyr Ser Ile Asn
945                 950                 955                 960

Val Gly Gly Phe Phe Lys Leu Arg Ala Gly Glu Glu Ile Ser Ile Gln
                965                 970                 975

Val Ser Asn Pro Ser Leu Leu Asp Pro Asp Gln Asp Ala Thr Tyr Phe
            980                 985                 990

Gly Ala Phe Lys Val Gln Asp Ile  Asp
        995                 1000
```

<210> SEQ ID NO 15
<211> LENGTH: 1986
<212> TYPE: DNA
<213> ORGANISM: Artificial Sequence
<220> FEATURE:
<223> OTHER INFORMATION: Fusion protein

<400> SEQUENCE: 15

| | | |
|---|---|---|
| atgctgctct tcctcctctc tgcactggtc ctactcacac agcccctggg ctacctggaa | 60 |
| gcagaaatga agacctactc ccacagaaca acgcccagtg cttgcaccct ggtcatgtgt | 120 |
| agctcagtgg agagtggcct gctggtcgc gatggacggg atgggagaga gggccctcgg | 180 |
| ggcgagaagg gggacccagg tttgccagga gctgcagggc aagcagggat gcctggacaa | 240 |
| gctggcccag ttgggcccaa aggggacaat ggctctgttg agaacctgg accaaaggga | 300 |
| gacactgggc caagtatggg ccatcatcat catcatcatc atcatcatca cagcagcggc | 360 |
| catatcgaag tcgtcatat gcgacgtgtg cctggagtag ccccgactct tgtacggtcg | 420 |
| gcatctgaga ccagtgagaa cgccccttc atgtgtgctt acccaggctg caataagaga | 480 |
| tattttaagc tgtcccactt acagatgcac agcaggaagc acactggtga aaaccatac | 540 |
| cagtgtgact tcaaggactg tgaacgaagg ttttttcgtt cagaccagct caaaagacac | 600 |
| caaaggagac atacaggtgt gaaccattc cagtgtaaaa cttgtcagcg aaagttctcc | 660 |
| cggtccgacc acctgaagac ccacaccagg actcatacag gtgaaaagcc cttcagctgt | 720 |
| cggtggccaa gttgtcagaa aaagtttgcc cggtcagatg aattagtccg ccatcacaac | 780 |
| atgcatcaga gaaacatgac caaactccag ctggcgcttg acctccagg acctcccggt | 840 |
| gtgcctggtc cagctggaag agaaggtccc ctggggaagc aggggaacat aggacctcag | 900 |
| ggcaagccag gcccaaaagg agaagctggg cccaaaggag aagtaggtgc cccaggcatg | 960 |
| cagggctcgg caggggcaag aggcctcgca ggccctaagg gagagcgagg tgtccctggt | 1020 |
| gagcgtggag tccctggaaa cacaggggca gcagggtctg ctggagccat gggtcccccag | 1080 |
| ggaagtccag gtgccagggg accccgggga ttgaaggggg acaaaggcat tcctggagac | 1140 |
| aaaggagcaa agggagaaag tgggcttcca gatgttgctt ctctgaggca gcaggttgag | 1200 |
| gccttacagg acaagtaca gcacctccag gctgcttct ctcagtataa gaaagttgag | 1260 |
| ctcttcccaa atggccaaag tgtcggggag aagattttca agacagcagg ctttgtaaaa | 1320 |
| ccatttacgg aggcacagca tagaaggttg acaagatag aagatgaaag gaatcttcat | 1380 |
| gaagattttg tattcatgaa acgatacag agatgcaaca caggagaaag atccttatcc | 1440 |
| ttactgaact gtgaggagat taaaagccag tttgaaggct ttgtgaagga tataatgtta | 1500 |
| aacaaagagg agacgaagaa agaaaacagc tttgaaatgc aaaaaggtga tcagaatcct | 1560 |
| caaattgcgg cacatgtcat aagtgaggcc agcagtaaaa caacatctgt gttacagtgg | 1620 |
| gctgaaaaag gatactacac catgagcaac aacttggtaa ccctggaaaa tgggaaacag | 1680 |
| ctgaccgtta aaagacaagg actctattat atctatgccc aagtcacctt ctgttccaat | 1740 |
| cgggaagctt cgagtcaagc tccatttata gccagcctct gcctaaagtc ccccggtaga | 1800 |
| ttcgagagaa tcttactcag agctgcaaat acccacagtt ccgccaaacc ttgcgggcaa | 1860 |
| caatccattc acttgggagg agtatttgaa ttgcaaccag gtgcttcggt gtttgtcaat | 1920 |
| gtgactgatc aagccaagt gagccatggc actggcttca cgtcctttgg cttactcaaa | 1980 |
| ctctga | 1986 |

<210> SEQ ID NO 16

```
<211> LENGTH: 661
<212> TYPE: PRT
<213> ORGANISM: Artificial Sequence
<220> FEATURE:
<223> OTHER INFORMATION: Fusion protein

<400> SEQUENCE: 16

Met Leu Leu Phe Leu Leu Ser Ala Leu Val Leu Leu Thr Gln Pro Leu
1               5                   10                  15

Gly Tyr Leu Glu Ala Glu Met Lys Thr Tyr Ser His Arg Thr Thr Pro
            20                  25                  30

Ser Ala Cys Thr Leu Val Met Cys Ser Ser Val Glu Ser Gly Leu Pro
        35                  40                  45

Gly Arg Asp Gly Arg Asp Gly Arg Glu Gly Pro Arg Gly Glu Lys Gly
    50                  55                  60

Asp Pro Gly Leu Pro Gly Ala Ala Gly Gln Ala Gly Met Pro Gly Gln
65                  70                  75                  80

Ala Gly Pro Val Gly Pro Lys Gly Asp Asn Gly Ser Val Gly Glu Pro
                85                  90                  95

Gly Pro Lys Gly Asp Thr Gly Pro Ser Met Gly His His His His His
            100                 105                 110

His His His His Ser Ser Gly His Ile Glu Gly Arg His Met Arg
            115                 120                 125

Arg Val Pro Gly Val Ala Pro Thr Leu Val Arg Ser Ala Ser Glu Thr
    130                 135                 140

Ser Glu Lys Arg Pro Phe Met Cys Ala Tyr Pro Gly Cys Asn Lys Arg
145                 150                 155                 160

Tyr Phe Lys Leu Ser His Leu Gln Met His Ser Arg Lys His Thr Gly
                165                 170                 175

Glu Lys Pro Tyr Gln Cys Asp Phe Lys Asp Cys Glu Arg Arg Phe Phe
            180                 185                 190

Arg Ser Asp Gln Leu Lys Arg His Gln Arg Arg His Thr Gly Val Lys
        195                 200                 205

Pro Phe Gln Cys Lys Thr Cys Gln Arg Lys Phe Ser Arg Ser Asp His
    210                 215                 220

Leu Lys Thr His Thr Arg Thr His Thr Gly Glu Lys Pro Phe Ser Cys
225                 230                 235                 240

Arg Trp Pro Ser Cys Gln Lys Lys Phe Ala Arg Ser Asp Glu Leu Val
                245                 250                 255

Arg His His Asn Met His Gln Arg Asn Met Thr Lys Leu Gln Leu Ala
            260                 265                 270

Leu Gly Pro Pro Gly Pro Pro Gly Val Pro Gly Pro Ala Gly Arg Glu
        275                 280                 285

Gly Pro Leu Gly Lys Gln Gly Asn Ile Gly Pro Gln Gly Lys Pro Gly
    290                 295                 300

Pro Lys Gly Glu Ala Gly Pro Lys Gly Glu Val Gly Ala Pro Gly Met
305                 310                 315                 320

Gln Gly Ser Ala Gly Ala Arg Gly Leu Ala Gly Pro Lys Gly Glu Arg
                325                 330                 335

Gly Val Pro Gly Glu Arg Gly Val Pro Gly Asn Thr Gly Ala Ala Gly
            340                 345                 350

Ser Ala Gly Ala Met Gly Pro Gln Gly Ser Pro Gly Ala Arg Gly Pro
        355                 360                 365

Pro Gly Leu Lys Gly Asp Lys Gly Ile Pro Gly Asp Lys Gly Ala Lys
    370                 375                 380
```

Gly Glu Ser Gly Leu Pro Asp Val Ala Ser Leu Arg Gln Gln Val Glu
385                 390                 395                 400

Ala Leu Gln Gly Gln Val Gln His Leu Gln Ala Ala Phe Ser Gln Tyr
            405                 410                 415

Lys Lys Val Glu Leu Phe Pro Asn Gly Gln Ser Val Gly Glu Lys Ile
        420                 425                 430

Phe Lys Thr Ala Gly Phe Val Lys Pro Phe Thr Glu Ala Gln His Arg
    435                 440                 445

Arg Leu Asp Lys Ile Glu Asp Glu Arg Asn Leu His Glu Asp Phe Val
450                 455                 460

Phe Met Lys Thr Ile Gln Arg Cys Asn Thr Gly Glu Arg Ser Leu Ser
465                 470                 475                 480

Leu Leu Asn Cys Glu Glu Ile Lys Ser Gln Phe Glu Gly Phe Val Lys
            485                 490                 495

Asp Ile Met Leu Asn Lys Glu Glu Thr Lys Lys Glu Asn Ser Phe Glu
        500                 505                 510

Met Gln Lys Gly Asp Gln Asn Pro Gln Ile Ala Ala His Val Ile Ser
    515                 520                 525

Glu Ala Ser Ser Lys Thr Thr Ser Val Leu Gln Trp Ala Glu Lys Gly
530                 535                 540

Tyr Tyr Thr Met Ser Asn Asn Leu Val Thr Leu Glu Asn Gly Lys Gln
545                 550                 555                 560

Leu Thr Val Lys Arg Gln Gly Leu Tyr Tyr Ile Tyr Ala Gln Val Thr
            565                 570                 575

Phe Cys Ser Asn Arg Glu Ala Ser Ser Gln Ala Pro Phe Ile Ala Ser
        580                 585                 590

Leu Cys Leu Lys Ser Pro Gly Arg Phe Glu Arg Ile Leu Leu Arg Ala
    595                 600                 605

Ala Asn Thr His Ser Ser Ala Lys Pro Cys Gly Gln Gln Ser Ile His
610                 615                 620

Leu Gly Gly Val Phe Glu Leu Gln Pro Gly Ala Ser Val Phe Val Asn
625                 630                 635                 640

Val Thr Asp Pro Ser Gln Val Ser His Gly Thr Gly Phe Thr Ser Phe
            645                 650                 655

Gly Leu Leu Lys Leu
            660

<210> SEQ ID NO 17
<211> LENGTH: 2394
<212> TYPE: DNA
<213> ORGANISM: Artificial Sequence
<220> FEATURE:
<223> OTHER INFORMATION: Fusion protein

<400> SEQUENCE: 17
atgctgccct ttctctccat gcttgtcttg cttgtacagc ccctgggaaa tctgggagca      60
gaaatgaaga gcctctcgca gagatcagta cccaacacct gcaccctagt catgtgtagc     120
ccaacagaga atggcctgcc tggtcgtgat ggacgggatg ggagagaagg tccacggggt     180
gagaagggtg atccaggttt gccaggacct atggggctct cagggttgca ggccctaca     240 ggtccagttg gacccaaagg agagaatggc tctgctggcg aacctggacc aaagggagaa     300
cgtggactaa gtggaatggc tgattcccat aacaccccaat actgcaacct cgaagagagt     360
gctcaggccc aacaggaatt agacaatgac caggagacca tggagacatc agaggaggag     420

-continued

| | |
|---|---|
| gaagatacca ccacctcaaa taaagtgtat ggcagtgcaa taccaagtcc tccccagagt | 480 |
| cctcagagag cctactctcc ctgtgtggca ctggcctcca tccctgatag cccatctgag | 540 |
| gaagcttcca tcaaaggatc agagggcctg gaagacccac ttcatttgtt gcacaatgca | 600 |
| cagaacacaa aggtgtatga cttggtggac tttctggttt taaactatca aatgaaggca | 660 |
| ttcactacca aagcagaaat gttggaaaat attggtagag agtatgagga gtactaccct | 720 |
| ctgatcttta gtgaggcctc tgagtgcttt aagatggtct ttggccttga catggtagaa | 780 |
| gtggactcct ctgtccacac ctatatgctt gtcactgccc tggggatcac ctatgatggc | 840 |
| atgatgactg atgtccaggg tatgcccaag acaggtatcc tcatagctgt actgagtgtc | 900 |
| attttcatga agggaaacta tgtcagtgag agattatct gggaaatgct gaataacata | 960 |
| gggttgtgtg gtgggaggga tccttacata cataaagacc ccaggaagct catctctgag | 1020 |
| gagtttgtgc aggaagggta cctggaatac aggcaggtgc ccaatagtga tccccctagc | 1080 |
| tatgggttcc tgtggggccc aagggctttt gcagaaacca gcaaatgaa agtcttacag | 1140 |
| ttctttgcca gcattaataa gactcatccc agagcctacc ctgaaaagta tgcagaggct | 1200 |
| ttacaagatg agatagacag gaccaagacc tggatcttga acagatgctc caactcctct | 1260 |
| gacctacaca cattcgggaa cataggacct caaggcaaac caggtcctaa aggagaggct | 1320 |
| gggcccaaag gagaagtagg tgctcctggc atgcaaggat ctacagggc aaaaggctcc | 1380 |
| acaggccca aggagaaag aggtgcccct ggtgtgcaag gagccccagg gaatgctgga | 1440 |
| gcagcaggac ctgccggacc tgccggtcca cagggagctc caggttccag gggcccccca | 1500 |
| ggactcaagg gggacagagg tgttcctgga gacagaggaa tcaaaggtga agcgggcttt | 1560 |
| ccagacagtg ctgctctgag gcagcagatg gaggccttaa aggaaaaact acagcgtcta | 1620 |
| gaggttgcct tctcccacta tcagaaagct gcattgttcc ctgatggcca gttggctgcc | 1680 |
| ttgcaagcag acctgatgaa cctgcgcatg gagctgcaga gctaccgagg ttcagcaaca | 1740 |
| ccagccgccg cgggtgctcc agagttgacc gctggagtca aactcctgac accggcagct | 1800 |
| cctcgacccc acaactccag ccgcggccac aggaacagac gcgctttcca gggaccagag | 1860 |
| gaaacagaac aagatgtaga cctctcagct cctcctgcac catgcctgcc tggatgccgc | 1920 |
| cattctcaac atgatgataa tggaatgaac ctcagaaaca tcattcaaga ctgtctgcag | 1980 |
| ctgattgcag acagcgacac gccgactata cgaaaaggaa cttacacatt tgttccatgg | 2040 |
| cttctcagct ttaaaagagg aaatgccttg gaggagaaag agaacaaaat agtggtgagg | 2100 |
| caaacaggct atttcttcat ctacagccag gttctataca cggaccccat cttttgctatg | 2160 |
| ggtcatgtca tccagaggaa gaaagtacac gtctttgggg acgagctgag cctggtgacc | 2220 |
| ctgttccgat gtattcagaa tatgcccaaa acactgccca caattcctg ctactcggct | 2280 |
| ggcatcgcga ggctggaaga aggagatgag attcagcttg caattcctcg ggagaatgca | 2340 |
| cagatttcac gcaacggaga cgacaccttc tttggtgccc taaaactgct gtaa | 2394 |

<210> SEQ ID NO 18
<211> LENGTH: 797
<212> TYPE: PRT
<213> ORGANISM: Artificial Sequence
<220> FEATURE:
<223> OTHER INFORMATION: Fusion protein

<400> SEQUENCE: 18

Met Leu Pro Phe Leu Ser Met Leu Val Leu Val Gln Pro Leu Gly
1               5                   10                  15

-continued

Asn Leu Gly Ala Glu Met Lys Ser Leu Ser Gln Arg Ser Val Pro Asn
            20                  25                  30
Thr Cys Thr Leu Val Met Cys Ser Pro Thr Glu Asn Gly Leu Pro Gly
        35                  40                  45
Arg Asp Gly Arg Asp Gly Arg Glu Gly Pro Arg Gly Glu Lys Gly Asp
    50                  55                  60
Pro Gly Leu Pro Gly Pro Met Gly Leu Ser Gly Leu Gln Gly Pro Thr
65                  70                  75                  80
Gly Pro Val Gly Pro Lys Gly Glu Asn Gly Ser Ala Gly Glu Pro Gly
                85                  90                  95
Pro Lys Gly Glu Arg Gly Leu Ser Gly Met Ala Asp Ser His Asn Thr
            100                 105                 110
Gln Tyr Cys Asn Leu Glu Glu Ser Ala Gln Ala Gln Gln Glu Leu Asp
        115                 120                 125
Asn Asp Gln Glu Thr Met Glu Thr Ser Glu Glu Glu Asp Thr Thr
    130                 135                 140
Thr Ser Asn Lys Val Tyr Gly Ser Ala Ile Pro Ser Pro Gln Ser
145                 150                 155                 160
Pro Gln Arg Ala Tyr Ser Pro Cys Val Ala Leu Ala Ser Ile Pro Asp
                165                 170                 175
Ser Pro Ser Glu Glu Ala Ser Ile Lys Gly Ser Glu Gly Leu Glu Asp
            180                 185                 190
Pro Leu His Leu Leu His Asn Ala Gln Asn Thr Lys Val Tyr Asp Leu
        195                 200                 205
Val Asp Phe Leu Val Leu Asn Tyr Gln Met Lys Ala Phe Thr Thr Lys
    210                 215                 220
Ala Glu Met Leu Glu Asn Ile Gly Arg Glu Tyr Glu Glu Tyr Tyr Pro
225                 230                 235                 240
Leu Ile Phe Ser Glu Ala Ser Glu Cys Leu Lys Met Val Phe Gly Leu
                245                 250                 255
Asp Met Val Glu Val Asp Ser Ser Val His Thr Tyr Met Leu Val Thr
            260                 265                 270
Ala Leu Gly Ile Thr Tyr Asp Gly Met Met Thr Asp Val Gln Gly Met
        275                 280                 285
Pro Lys Thr Gly Ile Leu Ile Ala Val Leu Ser Val Ile Phe Met Lys
    290                 295                 300
Gly Asn Tyr Val Ser Glu Glu Ile Ile Trp Glu Met Leu Asn Asn Ile
305                 310                 315                 320
Gly Leu Cys Gly Gly Arg Asp Pro Tyr Ile His Lys Asp Pro Arg Lys
                325                 330                 335
Leu Ile Ser Glu Glu Phe Val Gln Glu Gly Tyr Leu Glu Tyr Arg Gln
            340                 345                 350
Val Pro Asn Ser Asp Pro Pro Ser Tyr Gly Phe Leu Trp Gly Pro Arg
        355                 360                 365
Ala Phe Ala Glu Thr Ser Lys Met Lys Val Leu Gln Phe Phe Ala Ser
    370                 375                 380
Ile Asn Lys Thr His Pro Arg Ala Tyr Pro Glu Lys Tyr Ala Glu Ala
385                 390                 395                 400
Leu Gln Asp Glu Ile Asp Arg Thr Lys Thr Trp Ile Leu Asn Arg Cys
                405                 410                 415
Ser Asn Ser Ser Asp Leu His Thr Phe Gly Asn Ile Gly Pro Gln Gly
            420                 425                 430
Lys Pro Gly Pro Lys Gly Glu Ala Gly Pro Lys Gly Glu Val Gly Ala

-continued

```
            435                 440                 445
Pro Gly Met Gln Gly Ser Thr Gly Ala Lys Gly Ser Thr Gly Pro Lys
            450                 455                 460
Gly Glu Arg Gly Ala Pro Gly Val Gln Gly Ala Pro Gly Asn Ala Gly
465                 470                 475                 480
Ala Ala Gly Pro Ala Gly Pro Ala Gly Pro Gln Gly Ala Pro Gly Ser
                485                 490                 495
Arg Gly Pro Pro Gly Leu Lys Gly Asp Arg Gly Val Pro Gly Asp Arg
            500                 505                 510
Gly Ile Lys Gly Glu Ser Gly Leu Pro Asp Ser Ala Ala Leu Arg Gln
            515                 520                 525
Gln Met Glu Ala Leu Lys Gly Lys Leu Gln Arg Leu Glu Val Ala Phe
            530                 535                 540
Ser His Tyr Gln Lys Ala Ala Leu Phe Pro Asp Gly Gln Leu Ala Ala
545                 550                 555                 560
Leu Gln Ala Asp Leu Met Asn Leu Arg Met Glu Leu Gln Ser Tyr Arg
                565                 570                 575
Gly Ser Ala Thr Pro Ala Ala Gly Ala Pro Glu Leu Thr Ala Gly
                580                 585                 590
Val Lys Leu Leu Thr Pro Ala Ala Pro Arg Pro His Asn Ser Ser Arg
            595                 600                 605
Gly His Arg Asn Arg Ala Phe Gln Gly Pro Glu Glu Thr Glu Gln
            610                 615                 620
Asp Val Asp Leu Ser Ala Pro Pro Ala Pro Cys Leu Pro Gly Cys Arg
625                 630                 635                 640
His Ser Gln His Asp Asp Asn Gly Met Asn Leu Arg Asn Ile Ile Gln
                645                 650                 655
Asp Cys Leu Gln Leu Ile Ala Asp Ser Asp Thr Pro Thr Ile Arg Lys
            660                 665                 670
Gly Thr Tyr Thr Phe Val Pro Trp Leu Leu Ser Phe Lys Arg Gly Asn
            675                 680                 685
Ala Leu Glu Glu Lys Glu Asn Lys Ile Val Val Arg Gln Thr Gly Tyr
690                 695                 700
Phe Phe Ile Tyr Ser Gln Val Leu Tyr Thr Asp Pro Ile Phe Ala Met
705                 710                 715                 720
Gly His Val Ile Gln Arg Lys Lys Val His Val Phe Gly Asp Glu Leu
                725                 730                 735
Ser Leu Val Thr Leu Phe Arg Cys Ile Gln Asn Met Pro Lys Thr Leu
                740                 745                 750
Pro Asn Asn Ser Cys Tyr Ser Ala Gly Ile Ala Arg Leu Glu Glu Gly
            755                 760                 765
Asp Glu Ile Gln Leu Ala Ile Pro Arg Glu Asn Ala Gln Ile Ser Arg
            770                 775                 780
Asn Gly Asp Asp Thr Phe Phe Gly Ala Leu Lys Leu Leu
785                 790                 795
```

What is claimed is:

1. A composition comprised of a plurality of individual polypeptide chains that self-assemble into a two-trimer quaternary structure, the quaternary structure comprising:
    (a) a dimerizing multimerization scaffold, operatively linked to
    (b) two or more complete Tumor Necrosis Factor Super-Family (TNFSF) receptor binders, wherein the two or more complete TNFSF receptor binders bind a complete TNFSF receptor to activate a responding cell, operatively linked to (c) one or more immunogenic antigens, wherein each respective polypeptide chain comprises, in a N-terminus to C-terminus orientation, (i) a dimerizing component of the multimerization scaffold, wherein the dimerizing component is the Fc portion of an immunoglobulin molecule comprising a hub region allowing for the self-assembly of the polypeptide chains, which is operatively linked to (ii) an antigen of the one or more immunogenic antigens, which is operatively linked to (iii) a trimerizing component of the multimerization scaffold, which is operatively linked to (iv) a TNFSF receptor binder, wherein the TNFSF binder is not OX40L, wherein the composition is free of avidin or streptavidin portions.

2. The composition of claim 1, wherein the composition is capable of inducing, enhancing or sustaining a T cell response to an antigen presenting cell (APC).

3. The composition of claim 1, wherein the dimerizing component (i) of the multimerization scaffold is the Fc portion of an immunoglobulin.

4. The composition of claim 1, wherein the trimerizing component (iii) of the multimerization scaffold is selected from the group comprising coiled-coil region of yeast GCN4 isoleucine variant, TRAF2, thrombospondin 1, Matrilin-4, cubilin, or the neck region of surfactant protein D.

5. The composition of claim 1, wherein the TNFSF receptor binder (iv) is comprised of an extracellular domain of a TNFSF protein or of a TNFSF receptor binding portion of an antibody that binds to a TNFSF receptor.

6. The composition of claim 5, wherein the TNFSF receptor binding portion of the antibody is a single-chain antibody construct.

7. The composition of claim 1, wherein each respective polypeptide chain comprises an N-terminal t-PA signal for protein secretion.

8. The composition of claim 1 for administering to a subject as a vaccine or immunotherapy to elicit an immune response against the antigen (ii) in a subject in need thereof.

9. The composition of claim 8, wherein the antigen is from an infectious disease agent selected from the group of viruses, bacteria, fungi, protozoa, parasites, malignant cells or cancer-causing viruses.

10. A nucleic acid sequence encoding the plurality of polypeptide chains of claim 1.

11. The nucleic acid sequence of claim 10, comprising nucleic acid sequence SEQ ID NO: 7.

12. A vaccine or immunogenic composition for immunotherapy comprising the nucleic acid sequence of claim 10.

13. The vaccine or immunotherapy of claim 12, wherein the antigen is from an infectious disease agent selected from the group of viruses, bacteria, fungi, protozoa, or parasites.

14. The vaccine or immunotherapy of claim 12, wherein the antigen is from a malignant cell or cancer-causing virus.

15. The vaccine or immunotherapy of claim 12, wherein the nucleic acid sequence is delivered to a subject as DNA or RNA either alone or mixed with polymers to enhance the expression of protein from the nucleic acid sequence in vivo.

16. The vaccine or immunotherapy of claim 8, wherein the nucleic acid sequence is delivered to a subject using a viral vector selected from but not limited to adenoviruses, poxviruses, alphaviruses, arenaviruses, flaviruses, rhabdoviruses, retroviruses, lentiviruses, herpesviruses, paramyxoviruses, and picornaviruses.

17. The composition of claim 8, wherein the antigen (ii) is from an infectious disease agent that is a virus.

18. The vaccine or immunogenic composition according to claim 12, wherein the antigen (ii) is from an infectious disease agent that is a virus.

19. The vaccine or immunogenic composition according to claim 12, wherein the nucleic acid sequence is delivered to a subject as a DNA or RNA either alone or mixed with polymers to enhance the expression of protein from the nucleic acid sequence in vivo using an adenoviruses viral vector.

* * * * *